(12) United States Patent
Bramucci et al.

(10) Patent No.: US 8,795,992 B2
(45) Date of Patent: Aug. 5, 2014

(54) YEAST WITH INCREASED BUTANOL TOLERANCE INVOLVING CELL WALL INTEGRITY PATHWAY

(75) Inventors: Michael G. Bramucci, Boothwyn, PA (US); Robert A. Larossa, Chadds Ford, PA (US); Dana R. Smulski, Wilmington, DE (US)

(73) Assignee: Butamax Advanced Biofuels LLC, Wilmington, DE (US)

( * ) Notice: Subject to any disclaimer, the term of this patent is extended or adjusted under 35 U.S.C. 154(b) by 199 days.

(21) Appl. No.: 12/643,030

(22) Filed: Dec. 21, 2009

(65) Prior Publication Data
US 2010/0167364 A1    Jul. 1, 2010

Related U.S. Application Data

(60) Provisional application No. 61/141,009, filed on Dec. 29, 2008.

(51) Int. Cl.
*C12P 7/16* (2006.01)
*C12N 1/00* (2006.01)
*C12N 15/74* (2006.01)

(52) U.S. Cl.
USPC ............ 435/160; 435/254.2; 435/254.21; 435/254.22; 435/254.23; 435/471

(58) Field of Classification Search
USPC ............ 435/160, 254.2, 254.21, 254.22, 435/254.23, 471
See application file for complete search history.

(56) References Cited

U.S. PATENT DOCUMENTS

| | | | |
|---|---|---|---|
| 4,683,202 | A | 7/1987 | Mullis et al. |
| 2007/0092957 | A1 | 4/2007 | Donaldson et al. |
| 2007/0259410 | A1 | 11/2007 | Donaldson et al. |
| 2007/0292927 | A1 | 12/2007 | Donaldson et al. |
| 2008/0182308 | A1 | 7/2008 | Donaldson et al. |
| 2008/0261230 | A1 | 10/2008 | Liao et al. |
| 2009/0163376 | A1 | 6/2009 | Li et al. |
| 2009/0269823 | A1 | 10/2009 | Bramucci et al. |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Kisselev L., Polypeptide release factors in prokaryotes and eukaryotes: same function, different structure. Structure, 2002, vol. 10: 8-9.*
Seffernick et al., Melamine deaminase and Atrazine chlorohydrolase: 98 percent identical but functionally different. J. Bacteriol., 2001, vol. 183 (8): 2405-2410.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
Dickinson Jr., 'Fusel' alcohols induce hyphal-like extensions and pseudohyphal formation. Microbiology, 1996, vol. 142: 1391-1397.*
Martin-Yken et al., The interaction of Slt2 MAP kinase with Knr4 is necessary for signalling through the cell wall integrity pathway in Saccharomyces cerevisiae. Mol Microbiol., 2003, vol. 49 (1): 23-35.*
U.S. Appl. No. 12/569,636, filed Sep. 29, 2009, Flint et al.
Altschul, S. F., et al., J. Mol. Biol., 215:403 410 (1990).
Altschul et al. (1997) Nucleic Acids Research 25: 3389-3402.
Ashe et al. The EMBO Journal (2001) 20:6464-6474.
Botstein et al. (1979) Gene 8(1): 17-240.
Brachmann et al. (Yeast (1998) 14:115-132.
Chen and Thorner (2007) Biochimica et Biophysica Acta 1773:1311-1340.
Deshpande, Mukund V., Appl. Biochem. Biotechnol., 36:227, (1992).
Fuijta et al. (2006) FENMS Yeast Res 6:744-750.
Frohman et al., PNAS USA 85:8998 (1988).
Gelperin, White et al. (2005) Genes Dev. 19(23):2816-2826).
Gietz et al. (1995) Yeast 11:355-360.
Guo et al., J. Membr. Sci. 245, 199-210 (2004).
Higgins and Sharp, CABIOS. 5:151 153 (1989).
Jimenez-Sanchez and Molina (J. Biol. Chem. (2007) 282: 31174-85).
Johnston and Davis (1984) Mol. Cell. Biol. 4(8):1440-1448.
Kim et al. Mol. Cell. Biol. (2008) 281:2579-89.
Kim et al. Yeast (2007) 241: 335-42.
Levin, D. E. (2005) Microbiol. Mol. Biol. Rev.: 262-291.
Loh et al., Science 243:217 (1989).
Lorenz et al. Molec. Biol. Of the Cell (2000) 11:183-199.
Martinez-Anaya et al. (2003) Journal of Cell Science 116,3423-3431.
Ohara et al., PNAS USA 86:5673 (1989).
Reid et al. (2002) Yeast 19(4):319-328.
Reed et al. (1989) J. Cell Sci. Suppl. 12:29-37.
Smirnova et al. Molecular and Cellular Bioloty (2005) 25:9340-9340.
Sulter et al., Arch. Microbiol. 153:485 489 (1990).

(Continued)

*Primary Examiner* — Ganapathirama Raghu
(74) *Attorney, Agent, or Firm* — Andrew P. Baraniak

(57) ABSTRACT

Increasing tolerance to butanol in yeast has been accomplished by increasing activity of the cell wall integrity pathway. Yeast with increased expression of SLT2p, a mitogen activated protein kinase of the MAPK module of the cell wall integrity pathway had increased tolerance to isobutanol. These yeast may be used for improved butanol production.

8 Claims, 4 Drawing Sheets

(56) References Cited

OTHER PUBLICATIONS

Figure 1:
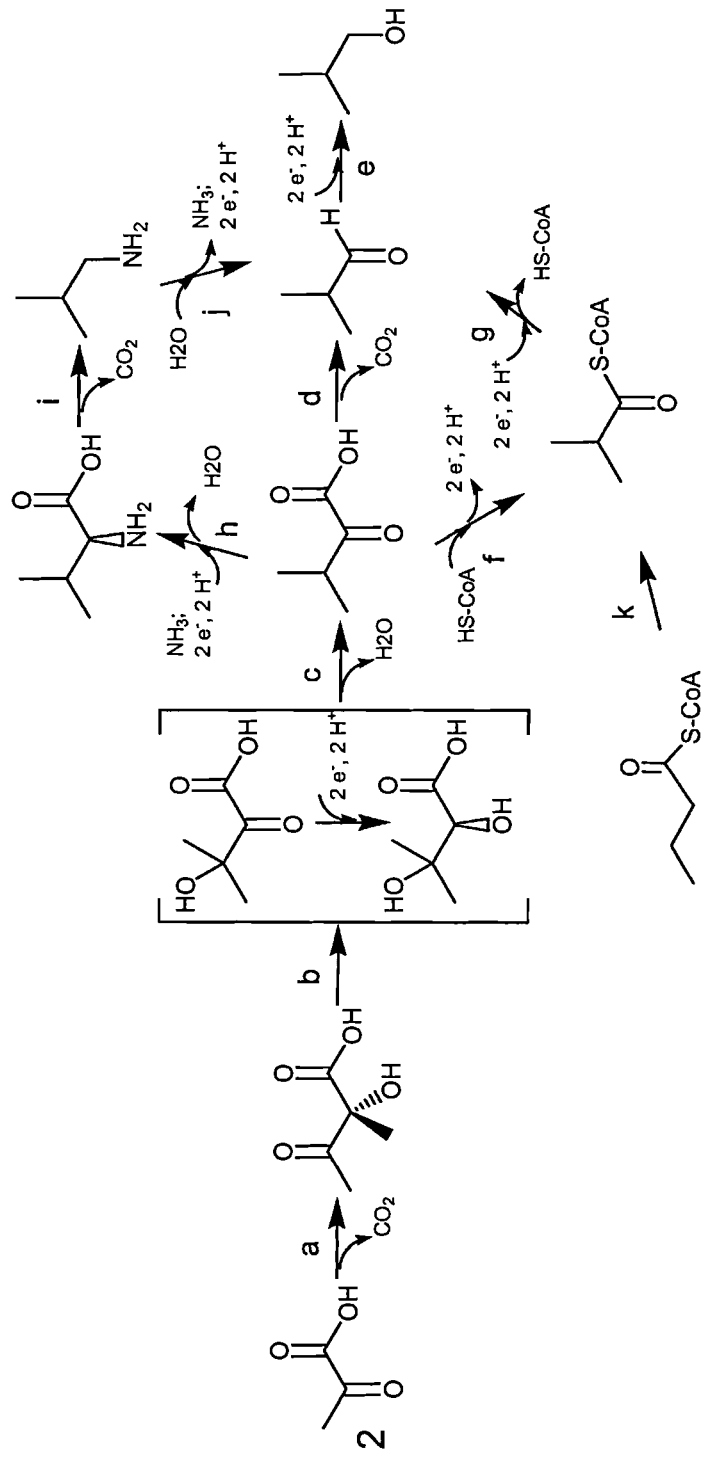

Tabor, S. et al., Proc. Acad. Sci. USA 82:1074 (1985).
Van Ness and Chen, Nucl. Acids Res. 19:5143 5151 (1991).
Van Voorst et al. (2006) Yeast 25(5):351-359.
Walker, et al., Proc. Natl. Acad. Sci. U.S.A., 89:392 (1992).
Aden et al. Lignocellulosic Biomass to Ethanol Process Design and Economics Utilizing Co-Current Dilute Acid Prehydrolysis and Enzymatic Hydrolysis for Corn Stover, Report NREL/TP-510-32438, National Renewable Energy Laboratory, Jun. 2002.
Ausubel, F. M. et al., in Current Protocols in Molecular Biology, published by Greene Publishing and Wiley-Interscience, 1987.
Amberg, Burke and Strathern, 2005, Methods in Yeast Genetics, Cold Spring Harbor Laboratory Press, Cold Spring Harbor, NY.
Bellion et al., Microb. Growth C1 Compd., [Int. Symp.], 7th (1993), 415 32. Editor(s): Murrell, J. Collin; Kelly, Don P. Publisher: Intercept, Andover, UK.
Biocomputing: Informatics and Genome Projects (Smith, D. W., Ed.) Academic: NY (1993).
Computational Molecular Biology (Lesk, A. M., Ed.) Oxford University: NY (1988).
Computer Analysis of Sequence Data, Part I (Griffin, A. M., and Griffin, H. G., Eds.) Humania: NJ (1994).
Doherty and Malone, Conceptual Design of Distillation Systems, McGraw Hill, New York, 2001.
Manual of Methods for General Bacteriology (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, DC (1994).
Methods in Enzymology, vol. 194, Guide to Yeast Genetics and Molecular and Cell Biology Part A, 2004, Christine Guthrie and Gerald R. Fink (Eds.), Elsevier Academic Press, San Diego, CA.
Methods in Yeast Genetics, 2005, Cold Spring Harbor Laboratory Press, Cold Spring Harbor, NY.
Rychlik, W., in Methods in Molecular Biology, White, B. A. Ed., (1993) vol. 15, pp. 31-39, PCR Protocols: Current Methods and Applications. Humania: Totowa, NJ.
Sambrook, J., Fritsch, E. F. And Maniatis, T. Molecular Cloning: A Laboratory Manual, 3rd ed., Cold Spring Harbor Laboratory: Cold Spring Harbor, NY (2001), particularly Chapter 11 and Table 11.1.
Sequence Analysis in Molecular Biology (von Heinje, G., Ed.) Academic (1987).
Sequence Analysis Primer (Gribskov, M. and Devereux, J., Eds.) Stockton: NY (1991).
Silhavy, T. J., Bennan, M. L. And Enquist, L. W. Experiments with Gene Fusions; Cold Spring Harbor Laboratory: Cold Spring Harbor, New York, 1984.
Thein and Wallace, "The use of oligonucleotides as specific hybridization probes in the Diagnosis of Genetic Disorders", in Human Genetic Diseases: A Practical Approach, K. E. Davis Ed., (1986) pp. 33-50, IRL: Herndon, VA.
Thomas D. Brock in Biotechnology: A Textbook of Industrial Microbiology, Second Edition (1989) Sinauer Associates, Inc., Sunderland, MA.
W. R. Pearson, Comput. Methods Genome Res., [Proc. Int. Symp.] (1994), Meeting Date 1992, 111-20. Editor(s): Suhai, Sandor. Plenum: New York, NY.
Yeast Protocols, Second Edition (Wei Xiao, ed; Humana Press, Totowa, NJ (2006).
Auesukaree et al., Genome-wide identification of genes involved in tolerance to various environmental stresses in *Saccharomyces cerevisae*, J. Appl. Genet. 50(3):301-10 2009.
Fujita et al., The genome-wide screening of yeast deletion mutatnts to identify the genes required for tolerance to ethanol and other alcohols, FEMS Yeast Res. 6:744-50, 2006.

\* cited by examiner

SEQUENCE LISTING

```
<160> NUMBER OF SEQ ID NOS: 91

<210> SEQ ID NO 1
<211> LENGTH: 1179
<212> TYPE: DNA
<213> ORGANISM: Clostridium acetobutylicum

<400> SEQUENCE: 1
atgaaagaag ttgtaatagc tagtgcagta agaacagcga ttggatctta tggaaagtct        60
cttaaggatg taccagcagt agatttagga gctacagcta taaaggaagc agttaaaaaa       120
gcaggaataa aaccagagga tgttaatgaa gtcattttag gaaatgttct tcaagcaggt       180
ttaggacaga atccagcaag acaggcatct tttaaagcag gattaccagt tgaaattcca       240
gctatgacta ttaataaggt ttgtggttca ggacttagaa cagttagctt agcagcacaa       300
attataaaag caggagatgc tgacgtaata atagcaggtg gtatggaaaa tatgtctaga       360
```

```
gctccttact tagcgaataa cgctagatgg ggatatagaa tgggaaacgc taaatttgtt    420
gatgaaatga tcactgacgg attgtgggat gcatttaatg attaccacat gggaataaca    480
gcagaaaaca tagctgagag atggaacatt tcaagagaag aacaagatga gtttgctctt    540
gcatcacaaa aaaagctga agaagctata aaatcaggtc aatttaaaga tgaaatagtt    600
cctgtagtaa ttaaaggcag aaagggagaa actgtagttg atacagatga gcaccctaga    660
tttggatcaa ctatagaagg acttgcaaaa ttaaaacctg ccttcaaaaa agatggaaca    720
gttacagctg gtaatgcatc aggattaaat gactgtgcag cagtacttgt aatcatgagt    780
gcagaaaaag ctaaagagct tggagtaaaa ccacttgcta agatagtttc ttatggttca    840
gcaggagttg acccagcaat aatgggatat ggaccttttct atgcaacaaa agcagctatt    900
gaaaaagcag gttggacagt tgatgaatta gatttaatag aatcaaatga agcttttgca    960
gctcaaagtt tagcagtagc aaaagattta aaatttgata tgaataaagt aaatgtaaat   1020
ggaggagcta ttgcccttgg tcatccaatt ggagcatcag gtgcaagaat actcgttact   1080
cttgtacacg caatgcaaaa aagagatgca aaaaaggct tagcaacttt atgtataggt   1140
ggcggacaag gaacagcaat attgctagaa aagtgctag                         1179

<210> SEQ ID NO 2
<211> LENGTH: 392
<212> TYPE: PRT
<213> ORGANISM: Clostridium acetobutylicum

<400> SEQUENCE: 2

Met Lys Glu Val Val Ile Ala Ser Ala Val Arg Thr Ala Ile Gly Ser
1               5                   10                  15

Tyr Gly Lys Ser Leu Lys Asp Val Pro Ala Val Asp Leu Gly Ala Thr
            20                  25                  30

Ala Ile Lys Glu Ala Val Lys Lys Ala Gly Ile Lys Pro Glu Asp Val
        35                  40                  45

Asn Glu Val Ile Leu Gly Asn Val Leu Gln Ala Gly Leu Gly Gln Asn
    50                  55                  60

Pro Ala Arg Gln Ala Ser Phe Lys Ala Gly Leu Pro Val Glu Ile Pro
65                  70                  75                  80

Ala Met Thr Ile Asn Lys Val Cys Gly Ser Gly Leu Arg Thr Val Ser
                85                  90                  95

Leu Ala Ala Gln Ile Ile Lys Ala Gly Asp Ala Asp Val Ile Ile Ala
            100                 105                 110

Gly Gly Met Glu Asn Met Ser Arg Ala Pro Tyr Leu Ala Asn Asn Ala
        115                 120                 125

Arg Trp Gly Tyr Arg Met Gly Asn Ala Lys Phe Val Asp Glu Met Ile
    130                 135                 140

Thr Asp Gly Leu Trp Asp Ala Phe Asn Asp Tyr His Met Gly Ile Thr
145                 150                 155                 160

Ala Glu Asn Ile Ala Glu Arg Trp Asn Ile Ser Arg Glu Glu Gln Asp
                165                 170                 175

Glu Phe Ala Leu Ala Ser Gln Lys Lys Ala Glu Glu Ala Ile Lys Ser
            180                 185                 190

Gly Gln Phe Lys Asp Glu Ile Val Pro Val Val Ile Lys Gly Arg Lys
        195                 200                 205

Gly Glu Thr Val Val Asp Thr Asp Glu His Pro Arg Phe Gly Ser Thr
    210                 215                 220
```

```
Ile Glu Gly Leu Ala Lys Leu Lys Pro Ala Phe Lys Lys Asp Gly Thr
225                 230                 235                 240

Val Thr Ala Gly Asn Ala Ser Gly Leu Asn Asp Cys Ala Ala Val Leu
                245                 250                 255

Val Ile Met Ser Ala Glu Lys Ala Lys Glu Leu Gly Val Lys Pro Leu
            260                 265                 270

Ala Lys Ile Val Ser Tyr Gly Ser Ala Gly Val Asp Pro Ala Ile Met
        275                 280                 285

Gly Tyr Gly Pro Phe Tyr Ala Thr Lys Ala Ala Ile Glu Lys Ala Gly
    290                 295                 300

Trp Thr Val Asp Glu Leu Asp Leu Ile Glu Ser Asn Glu Ala Phe Ala
305                 310                 315                 320

Ala Gln Ser Leu Ala Val Ala Lys Asp Leu Lys Phe Asp Met Asn Lys
                325                 330                 335

Val Asn Val Asn Gly Gly Ala Ile Ala Leu Gly His Pro Ile Gly Ala
                340                 345                 350

Ser Gly Ala Arg Ile Leu Val Thr Leu Val His Ala Met Gln Lys Arg
            355                 360                 365

Asp Ala Lys Lys Gly Leu Ala Thr Leu Cys Ile Gly Gly Gly Gln Gly
        370                 375                 380

Thr Ala Ile Leu Leu Glu Lys Cys
385                 390

<210> SEQ ID NO 3
<211> LENGTH: 1179
<212> TYPE: DNA
<213> ORGANISM: Clostridium acetobutylicum

<400> SEQUENCE: 3
atgagagatg tagtaatagt aagtgctgta agaactgcaa taggagcata tggaaaaaca      60
ttaaaggatg tacctgcaac agagttagga gctatagtaa taaggaagc tgtaagaaga     120 gctaatataa atccaaatga gattaatgaa gttatttttg gaaatgtact tcaagctgga     180
ttaggccaaa acccagcaag acaagcagca gtaaaagcag gattaccttt agaaacacct     240
gcgtttacaa tcaataaggt ttgtggttca ggtttaagat ctataagttt agcagctcaa     300
attataaaag ctggagatgc tgataccatt gtagtaggtg gtatggaaaa tatgtctaga     360
tcaccatatt tgattaacaa tcagagatgg ggtcaaagaa tgggagatag tgaattagtt     420
gatgaaatga taaggatgg tttgtgggat gcatttaatg gatatcatat gggagtaact     480
gcagaaaata ttgcagaaca atggaatata acaagagaag agcaagatga attttcactt     540
atgtcacaac aaaaagctga aaaagccatt aaaaatggag aatttaagga tgaaatagtt     600
cctgtattaa taaagactaa aaaaggtgaa atagtctttg atcaagatga atttcctaga     660
ttcggaaaca ctattgaagc attaagaaaa cttaaaccta ttttcaagga aaatggtact     720
gttacagcag gtaatgcatc cggattaaat gatggagctg cagcactagt aataatgagc     780
gctgataaag ctaacgctct cggaataaaa ccacttgcta agattacttc ttacggatca     840 tatgggggtag atccatcaat aatgggatat ggagcttttt atgcaactaa agctgcctta     900
gataaaatta atttaaaacc tgaagactta gatttaattg aagctaacga ggcatatgct     960
tctcaaagta tagcagtaac tagagattta aatttagata tgagtaaagt taatgttaat    1020
ggtggagcta tagcacttgg acatccaata ggtgcatctg gtgcacgtat tttagtaaca    1080
ttactatacg ctatgcaaaa aagagattca aaaaaaggtc ttgctactct atgtattggt    1140
```
ggaggtcagg gaacagctct cgtagttgaa agagactaa 1179

<210> SEQ ID NO 4
<211> LENGTH: 392
<212> TYPE: PRT
<213> ORGANISM: Clostridium acetobutylicum

<400> SEQUENCE: 4

Met Arg Asp Val Val Ile Val Ser Ala Val Arg Thr Ala Ile Gly Ala
1               5                   10                  15

Tyr Gly Lys Thr Leu Lys Asp Val Pro Ala Thr Glu Leu Gly Ala Ile
                20                  25                  30

Val Ile Lys Glu Ala Val Arg Arg Ala Asn Ile Asn Pro Asn Glu Ile
            35                  40                  45

Asn Glu Val Ile Phe Gly Asn Val Leu Gln Ala Gly Leu Gly Gln Asn
        50                  55                  60

Pro Ala Arg Gln Ala Ala Val Lys Ala Gly Leu Pro Leu Glu Thr Pro
65                  70                  75                  80

Ala Phe Thr Ile Asn Lys Val Cys Gly Ser Gly Leu Arg Ser Ile Ser
                85                  90                  95

Leu Ala Ala Gln Ile Ile Lys Ala Gly Asp Ala Asp Thr Ile Val Val
            100                 105                 110

Gly Gly Met Glu Asn Met Ser Arg Ser Pro Tyr Leu Ile Asn Asn Gln
        115                 120                 125

Arg Trp Gly Gln Arg Met Gly Asp Ser Glu Leu Val Asp Glu Met Ile
130                 135                 140

Lys Asp Gly Leu Trp Asp Ala Phe Asn Gly Tyr His Met Gly Val Thr
145                 150                 155                 160

Ala Glu Asn Ile Ala Glu Gln Trp Asn Ile Thr Arg Glu Glu Gln Asp
                165                 170                 175

Glu Phe Ser Leu Met Ser Gln Gln Lys Ala Glu Lys Ala Ile Lys Asn
            180                 185                 190

Gly Glu Phe Lys Asp Glu Ile Val Pro Val Leu Ile Lys Thr Lys Lys
        195                 200                 205

Gly Glu Ile Val Phe Asp Gln Asp Glu Phe Pro Arg Phe Gly Asn Thr
    210                 215                 220

Ile Glu Ala Leu Arg Lys Leu Lys Pro Ile Phe Lys Glu Asn Gly Thr
225                 230                 235                 240

Val Thr Ala Gly Asn Ala Ser Gly Leu Asn Asp Gly Ala Ala Ala Leu
                245                 250                 255

Val Ile Met Ser Ala Asp Lys Ala Asn Ala Leu Gly Ile Lys Pro Leu
            260                 265                 270

Ala Lys Ile Thr Ser Tyr Gly Ser Tyr Gly Val Asp Pro Ser Ile Met
        275                 280                 285

Gly Tyr Gly Ala Phe Tyr Ala Thr Lys Ala Ala Leu Asp Lys Ile Asn
    290                 295                 300

Leu Lys Pro Glu Asp Leu Asp Leu Ile Glu Ala Asn Glu Ala Tyr Ala
305                 310                 315                 320

Ser Gln Ser Ile Ala Val Thr Arg Asp Leu Asn Leu Asp Met Ser Lys
                325                 330                 335

Val Asn Val Asn Gly Gly Ala Ile Ala Leu Gly His Pro Ile Gly Ala
            340                 345                 350

Ser Gly Ala Arg Ile Leu Val Thr Leu Leu Tyr Ala Met Gln Lys Arg
        355                 360                 365

```
Asp Ser Lys Lys Gly Leu Ala Thr Leu Cys Ile Gly Gly Gln Gly
    370                 375                 380

Thr Ala Leu Val Val Glu Arg Asp
385                 390
```

<210> SEQ ID NO 5
<211> LENGTH: 849
<212> TYPE: DNA
<213> ORGANISM: Clostridium acetobutylicum

<400> SEQUENCE: 5

```
atgaaaaagg tatgtgttat aggtgcaggt actatgggtt caggaattgc tcaggcattt      60
gcagctaaag gatttgaagt agtattaaga gatattaaag atgaatttgt tgatagagga     120
ttagatttta tcaataaaaa tctttctaaa ttagttaaaa aaggaaagat agaagaagct     180
actaaagttg aaatcttaac tagaatttcc ggaacagttg accttaatat ggcagctgat     240
tgcgatttag ttatagaagc agctgttgaa agaatggata ttaaaaagca gattttttgct    300 gacttagaca atatatgcaa gccagaaaca attcttgcat caaatacatc atcactttca     360
ataacagaag tggcatcagc aactaaaaga cctgataagg ttataggtat gcatttcttt     420
aatccagctc ctgttatgaa gcttgtagag gtaataagag aatagctac atcacaagaa      480 actttttgatg cagttaaaga gacatctata gcaataggaa aagatcctgt agaagtagca    540
gaagcaccag gatttgttgt aaatagaata ttaataccaa tgattaatga agcagttggt     600
atattagcag aaggaatagc ttcagtagaa gacatagata aagctatgaa acttggagct     660
aatcacccaa tgggaccatt agaattaggt gattttatag gtcttgatat atgtcttgct     720
ataatggatg ttttatactc agaaactgga gattctaagt atagaccaca tacattactt     780
aagaagtatg taagagcagg atggcttgga agaaaatcag gaaaaggttt ctacgattat     840
tcaaaataa                                                            849
```

<210> SEQ ID NO 6
<211> LENGTH: 282
<212> TYPE: PRT
<213> ORGANISM: Clostridium acetobutylicum

<400> SEQUENCE: 6

```
Met Lys Lys Val Cys Val Ile Gly Ala Gly Thr Met Gly Ser Gly Ile
1               5                   10                  15

Ala Gln Ala Phe Ala Ala Lys Gly Phe Glu Val Val Leu Arg Asp Ile
            20                  25                  30

Lys Asp Glu Phe Val Asp Arg Gly Leu Asp Phe Ile Asn Lys Asn Leu
        35                  40                  45

Ser Lys Leu Val Lys Lys Gly Lys Ile Glu Glu Ala Thr Lys Val Glu
    50                  55                  60

Ile Leu Thr Arg Ile Ser Gly Thr Val Asp Leu Asn Met Ala Ala Asp
65                  70                  75                  80

Cys Asp Leu Val Ile Glu Ala Ala Val Glu Arg Met Asp Ile Lys Lys
                85                  90                  95

Gln Ile Phe Ala Asp Leu Asp Asn Ile Cys Lys Pro Glu Thr Ile Leu
            100                 105                 110

Ala Ser Asn Thr Ser Ser Leu Ser Ile Thr Glu Val Ala Ser Ala Thr
        115                 120                 125

Lys Arg Pro Asp Lys Val Ile Gly Met His Phe Phe Asn Pro Ala Pro
    130                 135                 140
```

```
Val Met Lys Leu Val Glu Val Ile Arg Gly Ile Ala Thr Ser Gln Glu
145                 150                 155                 160

Thr Phe Asp Ala Val Lys Glu Thr Ser Ile Ala Ile Gly Lys Asp Pro
                165                 170                 175

Val Glu Val Ala Glu Ala Pro Gly Phe Val Val Asn Arg Ile Leu Ile
            180                 185                 190

Pro Met Ile Asn Glu Ala Val Gly Ile Leu Ala Glu Gly Ile Ala Ser
            195                 200                 205

Val Glu Asp Ile Asp Lys Ala Met Lys Leu Gly Ala Asn His Pro Met
            210                 215                 220

Gly Pro Leu Glu Leu Gly Asp Phe Ile Gly Leu Asp Ile Cys Leu Ala
225                 230                 235                 240

Ile Met Asp Val Leu Tyr Ser Glu Thr Gly Asp Ser Lys Tyr Arg Pro
                245                 250                 255

His Thr Leu Leu Lys Lys Tyr Val Arg Ala Gly Trp Leu Gly Arg Lys
                260                 265                 270

Ser Gly Lys Gly Phe Tyr Asp Tyr Ser Lys
            275                 280

<210> SEQ ID NO 7
<211> LENGTH: 786
<212> TYPE: DNA
<213> ORGANISM: Clostridium acetobutylicum

<400> SEQUENCE: 7
atggaactaa acaatgtcat ccttgaaaag gaaggtaaag ttgctgtagt taccattaac      60
agacctaaag cattaaatgc gttaaatagt gatacactaa agaaatgga ttatgttata     120 ggtgaaattg aaaatgatag cgaagtactt gcagtaattt taactggagc aggagaaaaa     180
tcatttgtag caggagcaga tatttctgag atgaaggaaa tgaataccat tgaaggtaga     240
aaattcggga tacttggaaa taaagtgttt agaagattag aacttcttga aaagcctgta     300
atagcagctg ttaatggttt tgcttttagga ggcggatgcg aaatagctat gtcttgtgat     360
ataagaatag cttcaagcaa cgcaagattt ggtcaaccag aagtaggtct cggaataaca     420
cctggttttg gtggtacaca aagactttca agattagttg gaatgggcat ggcaaagcag     480
cttatattta ctgcacaaaa tataaaggca gatgaagcat taagaatcgg acttgtaaat     540
aaggtagtag aacctagtga attaatgaat acagcaaaag aaattgcaaa caaaattgtg     600
agcaatgctc cagtagctgt taagttaagc aaacaggcta ttaatagagg aatgcagtgt     660
gatattgata ctgctttagc atttgaatca gaagcatttg gagaatgctt ttcaacagag     720
gatcaaaagg atgcaatgac agctttcata gagaaaagaa aaattgaagg cttcaaaaat     780
agatag                                                                786

<210> SEQ ID NO 8
<211> LENGTH: 261
<212> TYPE: PRT
<213> ORGANISM: Clostridium acetobutylicum

<400> SEQUENCE: 8

Met Glu Leu Asn Asn Val Ile Leu Glu Lys Glu Gly Lys Val Ala Val
1               5                   10                  15

Val Thr Ile Asn Arg Pro Lys Ala Leu Asn Ala Leu Asn Ser Asp Thr
            20                  25                  30

Leu Lys Glu Met Asp Tyr Val Ile Gly Glu Ile Glu Asn Asp Ser Glu
        35                  40                  45
```

Val Leu Ala Val Ile Leu Thr Gly Ala Gly Glu Lys Ser Phe Val Ala
            50                  55                  60

Gly Ala Asp Ile Ser Glu Met Lys Glu Met Asn Thr Ile Glu Gly Arg
 65                  70                  75                  80

Lys Phe Gly Ile Leu Gly Asn Lys Val Phe Arg Arg Leu Glu Leu Leu
                85                  90                  95

Glu Lys Pro Val Ile Ala Ala Val Asn Gly Phe Ala Leu Gly Gly Gly
            100                 105                 110

Cys Glu Ile Ala Met Ser Cys Asp Ile Arg Ile Ala Ser Ser Asn Ala
            115                 120                 125

Arg Phe Gly Gln Pro Glu Val Gly Leu Gly Ile Thr Pro Gly Phe Gly
            130                 135                 140

Gly Thr Gln Arg Leu Ser Arg Leu Val Gly Met Gly Met Ala Lys Gln
145                 150                 155                 160

Leu Ile Phe Thr Ala Gln Asn Ile Lys Ala Asp Glu Ala Leu Arg Ile
                165                 170                 175

Gly Leu Val Asn Lys Val Val Glu Pro Ser Glu Leu Met Asn Thr Ala
            180                 185                 190

Lys Glu Ile Ala Asn Lys Ile Val Ser Asn Ala Pro Val Ala Val Lys
            195                 200                 205

Leu Ser Lys Gln Ala Ile Asn Arg Gly Met Gln Cys Asp Ile Asp Thr
210                 215                 220

Ala Leu Ala Phe Glu Ser Glu Ala Phe Gly Glu Cys Phe Ser Thr Glu
225                 230                 235                 240

Asp Gln Lys Asp Ala Met Thr Ala Phe Ile Glu Lys Arg Lys Ile Glu
                245                 250                 255

Gly Phe Lys Asn Arg
            260

<210> SEQ ID NO 9
<211> LENGTH: 1197
<212> TYPE: DNA
<213> ORGANISM: Clostridium acetobutylicum

<400> SEQUENCE: 9
atgatagtaa aagcaaagtt tgtaaaagga tttatcagag atgtacatcc ttatggttgc      60
agaagggaag tactaaatca atagattat tgtaagaagg ctattgggtt taggggacca     120
aagaaggttt taattgttgg agcctcatct gggtttggtc ttgctactag aatttcagtt     180
gcatttggag tccagaaagc tcacacaatt ggagtatcct atgaaacagg agctacagat     240
agaagaatag aacagcggg atggtataat aacatatttt ttaaagaatt tgctaaaaaa     300
aaaggattag ttgcaaaaaa cttcattgag gatgcctttt ctaatgaaac caaagataaa     360
gttattaagt atataaagga tgaatttggt aaaatagatt tatttgttta gtttagct      420 gcgcctagga gaaaggacta taaaactgga atgttttata cttcaagaat aaaaacaatt     480
ttaggagatt ttgagggacc gactattgat gttgaaagag acgagattac tttaaaaaag     540
gttagtagtg ctagcattga agaaattgaa gaaactagaa aggtaatggg tggagaggat     600
tggcaagagt ggtgtgaaga gctgctttat gaagattgtt tttcggataa agcaactacc     660
atagcatact cgtatatagg atccccaaga acctacaaga tatatagaga aggtactata     720
ggaatagcta aaaggatct tgaagataag gctaagctta taaatgaaaa acttaacaga     780
gttataggtg gtagagcctt tgtgtctgtg aataaagcat tagttacaaa agcaagtgca     840

| | | | |
|---|---|---|---|
| tatattccaa cttttcctct ttatgcagct attttatata aggtcatgaa agaaaaaaat | | | 900 |
| attcatgaaa attgtattat gcaaattgag agaatgtttt ctgaaaaaat atattcaaat | | | 960 |
| gaaaaatac aatttgatga caagggaaga ttaaggatgg acgatttaga gcttagaaaa | | | 1020 |
| gacgttcaag acgaagttga tagaatatgg agtaatatta ctcctgaaaa ttttaaggaa | | | 1080 |
| ttatctgatt ataagggata caaaaaagaa ttcatgaact taaacggttt tgatctagat | | | 1140 |
| ggggttgatt atagtaaaga cctggatata gaattattaa gaaaattaga accttaa | | | 1197 |

<210> SEQ ID NO 10
<211> LENGTH: 398
<212> TYPE: PRT
<213> ORGANISM: Clostridium acetobutylicum

<400> SEQUENCE: 10

```
Met Ile Val Lys Ala Lys Phe Val Lys Gly Phe Ile Arg Asp Val His
1               5                   10                  15

Pro Tyr Gly Cys Arg Arg Glu Val Leu Asn Gln Ile Asp Tyr Cys Lys
            20                  25                  30

Lys Ala Ile Gly Phe Arg Gly Pro Lys Lys Val Leu Ile Val Gly Ala
        35                  40                  45

Ser Ser Gly Phe Gly Leu Ala Thr Arg Ile Ser Val Ala Phe Gly Gly
    50                  55                  60

Pro Glu Ala His Thr Ile Gly Val Ser Tyr Glu Thr Gly Ala Thr Asp
65                  70                  75                  80

Arg Arg Ile Gly Thr Ala Gly Trp Tyr Asn Asn Ile Phe Phe Lys Glu
                85                  90                  95

Phe Ala Lys Lys Lys Gly Leu Val Ala Lys Asn Phe Ile Glu Asp Ala
            100                 105                 110

Phe Ser Asn Glu Thr Lys Asp Lys Val Ile Lys Tyr Ile Lys Asp Glu
        115                 120                 125

Phe Gly Lys Ile Asp Leu Phe Val Tyr Ser Leu Ala Ala Pro Arg Arg
    130                 135                 140

Lys Asp Tyr Lys Thr Gly Asn Val Tyr Thr Ser Arg Ile Lys Thr Ile
145                 150                 155                 160

Leu Gly Asp Phe Glu Gly Pro Thr Ile Asp Val Glu Arg Asp Glu Ile
                165                 170                 175

Thr Leu Lys Lys Val Ser Ser Ala Ser Ile Glu Glu Ile Glu Glu Thr
            180                 185                 190

Arg Lys Val Met Gly Gly Glu Asp Trp Gln Glu Trp Cys Glu Glu Leu
        195                 200                 205

Leu Tyr Glu Asp Cys Phe Ser Asp Lys Ala Thr Thr Ile Ala Tyr Ser
    210                 215                 220

Tyr Ile Gly Ser Pro Arg Thr Tyr Lys Ile Tyr Arg Glu Gly Thr Ile
225                 230                 235                 240

Gly Ile Ala Lys Lys Asp Leu Glu Asp Lys Ala Lys Leu Ile Asn Glu
                245                 250                 255

Lys Leu Asn Arg Val Ile Gly Gly Arg Ala Phe Val Ser Val Asn Lys
            260                 265                 270

Ala Leu Val Thr Lys Ala Ser Ala Tyr Ile Pro Thr Phe Pro Leu Tyr
        275                 280                 285

Ala Ala Ile Leu Tyr Lys Val Met Lys Glu Lys Asn Ile His Glu Asn
    290                 295                 300

Cys Ile Met Gln Ile Glu Arg Met Phe Ser Glu Lys Ile Tyr Ser Asn
305                 310                 315                 320
```

Glu Lys Ile Gln Phe Asp Asp Lys Gly Arg Leu Arg Met Asp Asp Leu
            325                 330                 335

Glu Leu Arg Lys Asp Val Gln Asp Glu Val Asp Arg Ile Trp Ser Asn
        340                 345                 350

Ile Thr Pro Glu Asn Phe Lys Glu Leu Ser Asp Tyr Lys Gly Tyr Lys
        355                 360                 365

Lys Glu Phe Met Asn Leu Asn Gly Phe Asp Leu Asp Gly Val Asp Tyr
    370                 375                 380

Ser Lys Asp Leu Asp Ile Glu Leu Leu Arg Lys Leu Glu Pro
385                 390                 395

<210> SEQ ID NO 11
<211> LENGTH: 1407
<212> TYPE: DNA
<213> ORGANISM: Clostridium beijerinckii

<400> SEQUENCE: 11
atgaataaag acacactaat acctacaact aaagatttaa aagtaaaaac aaatggtgaa      60
aacattaatt taaagaacta caaggataat tcttcatgtt tcggagtatt cgaaaatgtt     120
gaaaatgcta aagcagcgc tgtacacgca caaaagatat tatcccttca ttatacaaaa     180
gagcaaagag aaaaaatcat aactgagata agaaaggccg cattacaaaa taagagggtc     240
ttggctacaa tgattctaga gaaaacacat atgggaagat atgaggataa atattaaaa     300 catgaattgg tagctaaata tactcctggt acagaagatt taactactac tgcttggtca     360
ggtgataatg gtcttacagt gtagaaatg tctccatatg gtgttatagg tgcaataact     420
ccttctacga atccaactga actgtaata tgtaatagca taggcatgat agctgctgga     480
aatgctgtag tatttaacgg acacccatgc gctaaaaaat gtgttgcctt tgctgttgaa     540
atgataaata aggcaattat ttcatgtggc ggtcctgaaa atctagtaac aactataaaa     600
aatccaacta tggagtctct agatgcaatt attaagcatc cttcaataaa acttctttgc     660
ggaactgggg gtccaggaat ggtaaaaacc ctcttaaatt ctggtaagaa agctataggt     720
gctggtgctg gaaatccacc agttattgta gatgatactg ctgatataga aaaggctggt     780
aggagcatca ttgaaggctg ttcttttgat aataatttac cttgtattgc agaaaaagaa     840
gtatttgttt ttgagaatgt tgcagatgat ttaatatcta acatgctaaa aaataatgct     900
gtaattataa atgaagatca agtatcaaaa ttaatagatt tagtattaca aaaaaataat     960
gaaactcaag aatactttat aaacaaaaaa tgggtaggaa aagatgcaaa attattctta    1020
gatgaaatag atgttgagtc tccttcaaat gttaaatgca taatctgcga agtaaatgca    1080
aatcatccat tgttatgac agaactcatg atgccaatat tgccaattgt aagagttaaa    1140
gatatagatg aagctattaa atatgcaaag atagcagaac aaaatagaaa acatagtgcc    1200
tatatttatt ctaaaaatat agacaaccta aatagatttg aaagagaaat agatactact    1260 attttttgtaa agaatgctaa atcttttgct ggtgttggtt atgaagcaga aggatttaca    1320
actttcacta ttgctggatc tactggtgag ggaataacct ctgcaaggaa ttttacaaga    1380
caaagaagat gtgtacttgc cggctaa                                        1407

<210> SEQ ID NO 12
<211> LENGTH: 468
<212> TYPE: PRT
<213> ORGANISM: Clostridium beijerinckii

<400> SEQUENCE: 12

-continued

```
Met Asn Lys Asp Thr Leu Ile Pro Thr Thr Lys Asp Leu Lys Val Lys
1               5                   10                  15

Thr Asn Gly Glu Asn Ile Asn Leu Lys Asn Tyr Lys Asp Asn Ser Ser
            20                  25                  30

Cys Phe Gly Val Phe Glu Asn Val Glu Asn Ala Ile Ser Ser Ala Val
        35                  40                  45

His Ala Gln Lys Ile Leu Ser Leu His Tyr Thr Lys Glu Gln Arg Glu
    50                  55                  60

Lys Ile Ile Thr Glu Ile Arg Lys Ala Ala Leu Gln Asn Lys Glu Val
65                  70                  75                  80

Leu Ala Thr Met Ile Leu Glu Glu Thr His Met Gly Arg Tyr Glu Asp
                85                  90                  95

Lys Ile Leu Lys His Glu Leu Val Ala Lys Tyr Thr Pro Gly Thr Glu
                100                 105                 110

Asp Leu Thr Thr Thr Ala Trp Ser Gly Asp Asn Gly Leu Thr Val Val
            115                 120                 125

Glu Met Ser Pro Tyr Gly Val Ile Gly Ala Ile Thr Pro Ser Thr Asn
130                 135                 140

Pro Thr Glu Thr Val Ile Cys Asn Ser Ile Gly Met Ile Ala Ala Gly
145                 150                 155                 160

Asn Ala Val Val Phe Asn Gly His Pro Cys Ala Lys Lys Cys Val Ala
                165                 170                 175

Phe Ala Val Glu Met Ile Asn Lys Ala Ile Ile Ser Cys Gly Gly Pro
            180                 185                 190

Glu Asn Leu Val Thr Thr Ile Lys Asn Pro Thr Met Glu Ser Leu Asp
            195                 200                 205

Ala Ile Ile Lys His Pro Ser Ile Lys Leu Leu Cys Gly Thr Gly Gly
210                 215                 220

Pro Gly Met Val Lys Thr Leu Leu Asn Ser Gly Lys Lys Ala Ile Gly
225                 230                 235                 240

Ala Gly Ala Gly Asn Pro Pro Val Ile Val Asp Asp Thr Ala Asp Ile
                245                 250                 255

Glu Lys Ala Gly Arg Ser Ile Ile Glu Gly Cys Ser Phe Asp Asn Asn
            260                 265                 270

Leu Pro Cys Ile Ala Glu Lys Glu Val Phe Val Phe Glu Asn Val Ala
        275                 280                 285

Asp Asp Leu Ile Ser Asn Met Leu Lys Asn Asn Ala Val Ile Ile Asn
    290                 295                 300

Glu Asp Gln Val Ser Lys Leu Ile Asp Leu Val Leu Gln Lys Asn Asn
305                 310                 315                 320

Glu Thr Gln Glu Tyr Phe Ile Asn Lys Lys Trp Val Gly Lys Asp Ala
                325                 330                 335

Lys Leu Phe Leu Asp Glu Ile Asp Val Glu Ser Pro Ser Asn Val Lys
                340                 345                 350

Cys Ile Ile Cys Glu Val Asn Ala Asn His Pro Phe Val Met Thr Glu
            355                 360                 365

Leu Met Met Pro Ile Leu Pro Ile Val Arg Val Lys Asp Ile Asp Glu
        370                 375                 380

Ala Ile Lys Tyr Ala Lys Ile Ala Glu Gln Asn Arg Lys His Ser Ala
385                 390                 395                 400

Tyr Ile Tyr Ser Lys Asn Ile Asp Asn Leu Asn Arg Phe Glu Arg Glu
                405                 410                 415
```

```
Ile Asp Thr Thr Ile Phe Val Lys Asn Ala Lys Ser Phe Ala Gly Val
            420                 425                 430

Gly Tyr Glu Ala Glu Gly Phe Thr Thr Phe Thr Ile Ala Gly Ser Thr
        435                 440                 445

Gly Glu Gly Ile Thr Ser Ala Arg Asn Phe Thr Arg Gln Arg Arg Cys
    450                 455                 460

Val Leu Ala Gly
465

<210> SEQ ID NO 13
<211> LENGTH: 1215
<212> TYPE: DNA
<213> ORGANISM: Clostridium acetobutylicum

<400> SEQUENCE: 13
atggttgatt tcgaatattc aataccaact agaatttttt tcggtaaaga taagataaat      60
gtacttggaa gagagcttaa aaaatatggt tctaaagtgc ttatagttta tggtggagga     120
agtataaaga gaaatggaat atgatcaaa gctgtaagta cacttgaaaa aaacagtatt     180
aaattttatg aacttgcagg agtagagcca atccaagag taactacagt tgaaaaagga     240
gttaaaatat gtagagaaaa tggagttgaa gtagtactag ctataggtgg aggaagtgca     300
atagattgcg caaaggttat agcagcagca tgtgaatatg atggaaatcc atgggatatt     360
gtgttagatg gctcaaaaat aaaaagggtg cttcctatag ctgtatatt aaccattgct     420 gcaacaggat cagaaatgga tacgtgggca gtaataaata atatggatac aaacgaaaaa     480
ctaattgcgg cacatccaga tatggctcct aagtttcta tattagatcc aacgtatacg     540
tataccgtac ctaccaatca aacagcagca ggaacagctg atattatgag tcatatattt     600
gaggtgtatt ttagtaatac aaaaacagca tatttgcagg atagaatggc agaagcgtta     660
ttaagaactt gtattaaata tggaggaata gctcttgaga agccggatga ttatgaggca     720
agagccaatc taatgtgggc ttcaagtctt gcgataaatg acttttaac atatggtaaa     780 gacactaatt ggagtgtaca cttaatggaa catgaattaa gtgcttatta cgacataaca     840
cacggcgtag gcttgcaat tttaacacct aattggatgg agtatatttt aaataatgat     900
acagtgtaca gtttgttga atatggtgta atgtttggg aatagacaa agaaaaaaat     960 cactatgaca tagcacatca agcaatacaa aaaacaagag attactttgt aaatgtacta    1020
ggtttaccat ctagactgag agatgttgga attgaagaag aaaaattgga cataatggca    1080
aaggaatcag taaagcttac aggaggaacc ataggaaacc taagaccagt aaacgcctcc    1140
gaagtcctac aaatattcaa aaatctgtg taaaacgcct ccgaagtcct acaaatattc    1200
aaaaaatctg tgtaa                                                    1215

<210> SEQ ID NO 14
<211> LENGTH: 390
<212> TYPE: PRT
<213> ORGANISM: Clostridium acetobutylicum

<400> SEQUENCE: 14

Met Val Asp Phe Glu Tyr Ser Ile Pro Thr Arg Ile Phe Phe Gly Lys
1               5                   10                  15

Asp Lys Ile Asn Val Leu Gly Arg Glu Leu Lys Lys Tyr Gly Ser Lys
            20                  25                  30

Val Leu Ile Val Tyr Gly Gly Gly Ser Ile Lys Arg Asn Gly Ile Tyr
        35                  40                  45
```

```
Asp Lys Ala Val Ser Ile Leu Glu Lys Asn Ser Ile Lys Phe Tyr Glu
    50                  55                  60

Leu Ala Gly Val Glu Pro Asn Pro Arg Val Thr Thr Val Glu Lys Gly
65                  70                  75                  80

Val Lys Ile Cys Arg Glu Asn Gly Val Glu Val Val Leu Ala Ile Gly
                85                  90                  95

Gly Gly Ser Ala Ile Asp Cys Ala Lys Val Ile Ala Ala Ala Cys Glu
            100                 105                 110

Tyr Asp Gly Asn Pro Trp Asp Ile Val Leu Asp Gly Ser Lys Ile Lys
        115                 120                 125

Arg Val Leu Pro Ile Ala Ser Ile Leu Thr Ile Ala Ala Thr Gly Ser
    130                 135                 140

Glu Met Asp Thr Trp Ala Val Ile Asn Asn Met Asp Thr Asn Glu Lys
145                 150                 155                 160
Leu Ile Ala Ala His Pro Asp Met Ala Pro Lys Phe Ser Ile Leu Asp
                165                 170                 175
Pro Thr Tyr Thr Tyr Thr Val Pro Thr Asn Gln Thr Ala Ala Gly Thr
            180                 185                 190
Ala Asp Ile Met Ser His Ile Phe Glu Val Tyr Phe Ser Asn Thr Lys
        195                 200                 205

Thr Ala Tyr Leu Gln Asp Arg Met Ala Glu Ala Leu Leu Arg Thr Cys
    210                 215                 220

Ile Lys Tyr Gly Gly Ile Ala Leu Glu Lys Pro Asp Asp Tyr Glu Ala
225                 230                 235                 240
Arg Ala Asn Leu Met Trp Ala Ser Ser Leu Ala Ile Asn Gly Leu Leu
                245                 250                 255
Thr Tyr Gly Lys Asp Thr Asn Trp Ser Val His Leu Met Glu His Glu
            260                 265                 270
Leu Ser Ala Tyr Tyr Asp Ile Thr His Gly Val Gly Leu Ala Ile Leu
        275                 280                 285
Thr Pro Asn Trp Met Glu Tyr Ile Leu Asn Asn Asp Thr Val Tyr Lys
    290                 295                 300
Phe Val Glu Tyr Gly Val Asn Val Trp Gly Ile Asp Lys Glu Lys Asn
305                 310                 315                 320
His Tyr Asp Ile Ala His Gln Ala Ile Gln Lys Thr Arg Asp Tyr Phe
                325                 330                 335
Val Asn Val Leu Gly Leu Pro Ser Arg Leu Arg Asp Val Gly Ile Glu
            340                 345                 350
Glu Glu Lys Leu Asp Ile Met Ala Lys Glu Ser Val Lys Leu Thr Gly
        355                 360                 365
Gly Thr Ile Gly Asn Leu Arg Pro Val Asn Ala Ser Glu Val Leu Gln
    370                 375                 380

Ile Phe Lys Lys Ser Val
385                 390

<210> SEQ ID NO 15
<211> LENGTH: 1170
<212> TYPE: DNA
<213> ORGANISM: Clostridium acetobutylicum

<400> SEQUENCE: 15
atgctaagtt ttgattattc aataccaact aaagtttttt ttggaaaagg aaaaatagac      60
gtaattggag aagaaattaa gaaatatggc tcaagagtgc ttatagttta tggcggagga     120
agtataaaaa ggaacggtat atatgataga gcaacagcta tattaaaaga aaacaatata     180
```

```
gctttctatg aactttcagg agtagagcca atcctagga taacaacagt aaaaaaaggc      240
atagaaatat gtagagaaaa taatgtggat ttagtattag caataggggg aggaagtgca      300
atagactgtt ctaaggtaat tgcagctgga gtttattatg atggcgatac atgggacatg      360
gttaaagatc catctaaaat aactaaagtt cttccaattg caagtatact tactctttca      420
gcaacagggt ctgaaatgga tcaaattgca gtaatttcaa atatggagac taatgaaaag      480
cttggagtag acatgatga tatgagacct aaattttcag tgttagatcc tacatatact      540
tttacagtac ctaaaaatca aacagcagcg ggaacagctg acattatgag tcacaccttt      600
gaatcttact ttagtggtgt tgaaggtgct tatgtgcagg acggtatagc agaagcaatc      660
ttaagaacat gtataaagta tggaaaaata gcaatggaga agactgatga ttacgaggct      720
agagctaatt tgatgtgggc ttcaagttta gctataaatg gtctattatc acttggtaag      780
gatagaaaat ggagttgtca tcctatggaa cacgagttaa gtgcatatta tgatataaca      840
catggtgtag gacttgcaat tttaacacct aattggatgg aatatattct aaatgacgat      900
acacttcata aatttgtttc ttatggaata aatgtttggg aatagacaa gaacaaagat      960 aactatgaaa tagcacgaga ggctattaaa aatacgagag aatactttaa ttcattgggt     1020
attccttcaa agcttagaga agttggaata ggaaaagata actagaact aatggcaaag     1080 caagctgtta gaaattctgg aggaacaata ggaagtttaa gaccaataaa tgcagaggat     1140
gttcttgaga tatttaaaaa atcttattaa                                     1170

<210> SEQ ID NO 16
<211> LENGTH: 389
<212> TYPE: PRT
<213> ORGANISM: Clostridium acetobutylicum

<400> SEQUENCE: 16

Met Leu Ser Phe Asp Tyr Ser Ile Pro Thr Lys Val Phe Gly Lys
1               5                   10                  15

Gly Lys Ile Asp Val Ile Gly Glu Glu Ile Lys Lys Tyr Gly Ser Arg
            20                  25                  30

Val Leu Ile Val Tyr Gly Gly Gly Ser Ile Lys Arg Asn Gly Ile Tyr
        35                  40                  45

Asp Arg Ala Thr Ala Ile Leu Lys Glu Asn Asn Ile Ala Phe Tyr Glu
    50                  55                  60

Leu Ser Gly Val Glu Pro Asn Pro Arg Ile Thr Thr Val Lys Lys Gly
65                  70                  75                  80

Ile Glu Ile Cys Arg Glu Asn Asn Val Asp Leu Val Leu Ala Ile Gly
                85                  90                  95

Gly Gly Ser Ala Ile Asp Cys Ser Lys Val Ile Ala Ala Gly Val Tyr
            100                 105                 110

Tyr Asp Gly Asp Thr Trp Asp Met Val Lys Asp Pro Ser Lys Ile Thr
        115                 120                 125

Lys Val Leu Pro Ile Ala Ser Ile Leu Thr Leu Ser Ala Thr Gly Ser
    130                 135                 140

Glu Met Asp Gln Ile Ala Val Ile Ser Asn Met Glu Thr Asn Glu Lys
145                 150                 155                 160

Leu Gly Val Gly His Asp Asp Met Arg Pro Lys Phe Ser Val Leu Asp
                165                 170                 175

Pro Thr Tyr Thr Phe Thr Val Pro Lys Asn Gln Thr Ala Ala Gly Thr
            180                 185                 190
```

```
Ala Asp Ile Met Ser His Thr Phe Glu Ser Tyr Phe Ser Gly Val Glu
            195                 200                 205

Gly Ala Tyr Val Gln Asp Gly Ile Ala Glu Ala Ile Leu Arg Thr Cys
        210                 215                 220

Ile Lys Tyr Gly Lys Ile Ala Met Glu Lys Thr Asp Asp Tyr Glu Ala
225                 230                 235                 240

Arg Ala Asn Leu Met Trp Ala Ser Ser Leu Ala Ile Asn Gly Leu Leu
                245                 250                 255

Ser Leu Gly Lys Asp Arg Lys Trp Ser Cys His Pro Met Glu His Glu
            260                 265                 270

Leu Ser Ala Tyr Tyr Asp Ile Thr His Gly Val Gly Leu Ala Ile Leu
        275                 280                 285

Thr Pro Asn Trp Met Glu Tyr Ile Leu Asn Asp Asp Thr Leu His Lys
        290                 295                 300

Phe Val Ser Tyr Gly Ile Asn Val Trp Gly Ile Asp Lys Asn Lys Asp
305                 310                 315                 320

Asn Tyr Glu Ile Ala Arg Glu Ala Ile Lys Asn Thr Arg Glu Tyr Phe
                325                 330                 335

Asn Ser Leu Gly Ile Pro Ser Lys Leu Arg Glu Val Gly Ile Gly Lys
            340                 345                 350

Asp Lys Leu Glu Leu Met Ala Lys Gln Ala Val Arg Asn Ser Gly Gly
        355                 360                 365

Thr Ile Gly Ser Leu Arg Pro Ile Asn Ala Glu Asp Val Leu Glu Ile
        370                 375                 380

Phe Lys Lys Ser Tyr
385

<210> SEQ ID NO 17
<211> LENGTH: 780
<212> TYPE: DNA
<213> ORGANISM: Klebsiella pneumoniae

<400> SEQUENCE: 17
atgaatcatt ctgctgaatg cacctgcgaa gagagtctat gcgaaaccct gcgggcgttt      60
tccgcgcagc atcccgagag cgtgctctat cagacatcgc tcatgagcgc cctgctgagc     120
ggggtttacg aaggcagcac caccatcgcg gacctgctga acacggcga tttcggcctc     180 ggcacctta tgagctgga cggggagctg atcgccttca gcagtcaggt ctatcagctg      240
cgcgccgacg gcagcgcgcg caaagcccag ccggagcaga aaacgccgtt cgcggtgatg     300
acctggttcc agccgcagta ccggaaaacc tttgaccatc cggtgagccg ccagcagctg     360
cacgaggtga tcgaccagca aatcccctct gacaacctgt tctgcgccct gcgcatcgac     420
ggccatttcc gccatgccca tacccgcacc gtgccgcgcc agacgccgcc gtaccgggcg     480
atgaccgacg tcctcgacga tcagccggtg ttccgcttta accagcgcga aggggtgctg     540
gtcggcttcc ggaccccgca gcatatgcag gggatcaacg tcgccgggta tcacgagcac     600
tttattaccg atgaccgcaa aggcggcggt cacctgctgg attaccagct cgaccatggg     660
gtgctgacct tcggcgaaat tcacaagctg atgatcgacc tgcccgccga cagcgcgttc     720
ctgcaggcta atctgcatcc cgataatctc gatgccgcca tccgttccgt agaaagttaa     780

<210> SEQ ID NO 18
<211> LENGTH: 259
<212> TYPE: PRT
<213> ORGANISM: Klebsiella pneumoniae
```

<400> SEQUENCE: 18

```
Met Asn His Ser Ala Glu Cys Thr Cys Glu Glu Ser Leu Cys Glu Thr
1               5                   10                  15

Leu Arg Ala Phe Ser Ala Gln His Pro Glu Ser Val Leu Tyr Gln Thr
            20                  25                  30

Ser Leu Met Ser Ala Leu Leu Ser Gly Val Tyr Glu Gly Ser Thr Thr
        35                  40                  45

Ile Ala Asp Leu Leu Lys His Gly Asp Phe Gly Leu Gly Thr Phe Asn
50                  55                  60

Glu Leu Asp Gly Glu Leu Ile Ala Phe Ser Ser Gln Val Tyr Gln Leu
65                  70                  75                  80

Arg Ala Asp Gly Ser Ala Arg Lys Ala Gln Pro Glu Gln Lys Thr Pro
                85                  90                  95

Phe Ala Val Met Thr Trp Phe Gln Pro Gln Tyr Arg Lys Thr Phe Asp
            100                 105                 110

His Pro Val Ser Arg Gln Gln Leu His Glu Val Ile Asp Gln Gln Ile
        115                 120                 125

Pro Ser Asp Asn Leu Phe Cys Ala Leu Arg Ile Asp Gly His Phe Arg
130                 135                 140

His Ala His Thr Arg Thr Val Pro Arg Gln Thr Pro Pro Tyr Arg Ala
145                 150                 155                 160

Met Thr Asp Val Leu Asp Asp Gln Pro Val Phe Arg Phe Asn Gln Arg
                165                 170                 175

Glu Gly Val Leu Val Gly Phe Arg Thr Pro Gln His Met Gln Gly Ile
            180                 185                 190

Asn Val Ala Gly Tyr His Glu His Phe Ile Thr Asp Arg Lys Gly
        195                 200                 205

Gly Gly His Leu Leu Asp Tyr Gln Leu Asp His Gly Val Leu Thr Phe
210                 215                 220

Gly Glu Ile His Lys Leu Met Ile Asp Leu Pro Ala Asp Ser Ala Phe
225                 230                 235                 240

Leu Gln Ala Asn Leu His Pro Asp Asn Leu Asp Ala Ala Ile Arg Ser
                245                 250                 255

Val Glu Ser
```

<210> SEQ ID NO 19
<211> LENGTH: 1680
<212> TYPE: DNA
<213> ORGANISM: Klebsiella pneumoniae

<400> SEQUENCE: 19

```
atggacaaac agtatccggt acgccagtgg gcgcacggcg ccgatctcgt cgtcagtcag    60
ctggaagctc agggagtacg ccaggtgttc ggcatccccg cgccaaaat tgacaaggtc   120
ttcgactcac tgctggattc ctcgattcgc attattccgg tacgcacgca agccaacgcc   180
gcgtttatgg ccgccgccgt cggacgcatt accggcaaag cgggcgtggc gctggtcacc   240
tccggtccgg gctgttccaa cctgatcacc ggcatggcca ccgcgaacag cgaaggcgac   300
ccggtggtgg ccctgggcgg cgcggtaaaa cgcgccgata agcgaagca ggtccaccag   360
agtatggata cggtggcgat gttcagcccg gtcaccaaat acgccgtcga ggtgacggcg   420
ccggatgcgc tggcggaagt ggtctccaac gccttccgcg ccgccgagca gggccggccg   480
ggcagcgcgt tcgttagcct gccgcaggat gtggtcgatg cccggtcag cggcaaagtg   540
ctgccggcca gcggggcccc gcagatgggc gccgcgccgg atgatgccat cgaccaggtg   600
```

```
gcgaagctta tcgcccaggc gaagaacccg atcttcctgc tcggcctgat ggccagccag    660
ccggaaaaca gcaaggcgct gcgccgtttg ctggagacca gccatattcc agtcaccagc    720
acctatcagg ccgccggagc ggtgaatcag gataacttct ctcgcttcgc cggccgggtt    780
gggctgttta caaccaggc cggggaccgt ctgctgcagc tcgccgacct ggtgatctgc     840
atcggctaca gcccggtgga atacgaaccg gcgatgtgga acagcggcaa cgcgacgctg    900
gtgcacatcg acgtgctgcc cgcctatgaa gagcgcaact acaccccgga tgtcgagctg    960
gtgggcgata tcgccggcac tctcaacaag ctggcgcaaa atatcgatca tcggctggtg   1020
ctctccccgc aggcggcgga gatcctccgc gaccgccagc accagcgcga gctgctggac   1080
cgccgcggcg cgcagctgaa ccagtttgcc ctgcatccgc tgcgcatcgt tcgcgccatg   1140
caggacatcg tcaacagcga cgtcacgttg accgtggaca tgggcagctt ccatatctgg   1200
attgcccgct acctgtacag cttccgcgcc cgtcaggtga tgatctccaa cggccagcag   1260
accatgggcg tcgccctgcc ctgggctatc ggcgcctggc tggtcaatcc tgagcgaaaa   1320
gtggtctccg tctccggcga cggcggcttc ctgcagtcga gcatggagct ggagaccgcc   1380
gtccgcctga agccaacgt actgcacctg atctgggtcg ataacggcta caacatggtg    1440
gccattcagg aagagaaaaa ataccagcgc ctgtccggcg tcgagttcgg gccgatggat   1500
tttaaagcct atgccgaatc cttcggcgcg aaagggtttg ccgtggaaag cgccgaggcg   1560
ctggagccga ccctgcacgc ggcgatggac gtcgacggcc cggcggtggt ggccattccg   1620
gtggattatc gcgataaccc gctgctgatg ggccagctgc atctgagtca gattctgtaa   1680
```

<210> SEQ ID NO 20
<211> LENGTH: 559
<212> TYPE: PRT
<213> ORGANISM: Klebsiella pneumoniae

<400> SEQUENCE: 20

```
Met Asp Lys Gln Tyr Pro Val Arg Gln Trp Ala His Gly Ala Asp Leu
1               5                   10                  15

Val Val Ser Gln Leu Glu Ala Gln Gly Val Arg Gln Val Phe Gly Ile
                20                  25                  30

Pro Gly Ala Lys Ile Asp Lys Val Phe Asp Ser Leu Leu Asp Ser Ser
            35                  40                  45

Ile Arg Ile Ile Pro Val Arg His Glu Ala Asn Ala Ala Phe Met Ala
        50                  55                  60

Ala Ala Val Gly Arg Ile Thr Gly Lys Ala Gly Val Ala Leu Val Thr
65                  70                  75                  80

Ser Gly Pro Gly Cys Ser Asn Leu Ile Thr Gly Met Ala Thr Ala Asn
                85                  90                  95

Ser Glu Gly Asp Pro Val Val Ala Leu Gly Gly Ala Val Lys Arg Ala
            100                 105                 110

Asp Lys Ala Lys Gln Val His Gln Ser Met Asp Thr Val Ala Met Phe
        115                 120                 125

Ser Pro Val Thr Lys Tyr Ala Val Glu Val Thr Ala Pro Asp Ala Leu
    130                 135                 140

Ala Glu Val Val Ser Asn Ala Phe Arg Ala Glu Gln Gly Arg Pro
145                 150                 155                 160

Gly Ser Ala Phe Val Ser Leu Pro Gln Asp Val Val Asp Gly Pro Val
                165                 170                 175

Ser Gly Lys Val Leu Pro Ala Ser Gly Ala Pro Gln Met Gly Ala Ala
```

```
            180                 185                 190
Pro Asp Asp Ala Ile Asp Gln Val Ala Lys Leu Ile Ala Gln Ala Lys
            195                 200                 205

Asn Pro Ile Phe Leu Leu Gly Leu Met Ala Ser Gln Pro Glu Asn Ser
        210                 215                 220

Lys Ala Leu Arg Arg Leu Leu Glu Thr Ser His Ile Pro Val Thr Ser
225                 230                 235                 240

Thr Tyr Gln Ala Ala Gly Ala Val Asn Gln Asp Asn Phe Ser Arg Phe
                245                 250                 255

Ala Gly Arg Val Gly Leu Phe Asn Asn Gln Ala Gly Asp Arg Leu Leu
            260                 265                 270

Gln Leu Ala Asp Leu Val Ile Cys Ile Gly Tyr Ser Pro Val Glu Tyr
        275                 280                 285

Glu Pro Ala Met Trp Asn Ser Gly Asn Ala Thr Leu Val His Ile Asp
    290                 295                 300

Val Leu Pro Ala Tyr Glu Glu Arg Asn Tyr Thr Pro Asp Val Glu Leu
305                 310                 315                 320

Val Gly Asp Ile Ala Gly Thr Leu Asn Lys Leu Ala Gln Asn Ile Asp
                325                 330                 335

His Arg Leu Val Leu Ser Pro Gln Ala Ala Glu Ile Leu Arg Asp Arg
            340                 345                 350

Gln His Gln Arg Glu Leu Leu Asp Arg Arg Gly Ala Gln Leu Asn Gln
        355                 360                 365

Phe Ala Leu His Pro Leu Arg Ile Val Arg Ala Met Gln Asp Ile Val
    370                 375                 380

Asn Ser Asp Val Thr Leu Thr Val Asp Met Gly Ser Phe His Ile Trp
385                 390                 395                 400

Ile Ala Arg Tyr Leu Tyr Ser Phe Arg Ala Arg Gln Val Met Ile Ser
                405                 410                 415

Asn Gly Gln Gln Thr Met Gly Val Ala Leu Pro Trp Ala Ile Gly Ala
            420                 425                 430

Trp Leu Val Asn Pro Glu Arg Lys Val Val Ser Val Ser Gly Asp Gly
        435                 440                 445

Gly Phe Leu Gln Ser Ser Met Glu Leu Glu Thr Ala Val Arg Leu Lys
    450                 455                 460

Ala Asn Val Leu His Leu Ile Trp Val Asp Asn Gly Tyr Asn Met Val
465                 470                 475                 480

Ala Ile Gln Glu Glu Lys Lys Tyr Gln Arg Leu Ser Gly Val Glu Phe
                485                 490                 495

Gly Pro Met Asp Phe Lys Ala Tyr Ala Glu Ser Phe Gly Ala Lys Gly
            500                 505                 510

Phe Ala Val Glu Ser Ala Glu Leu Glu Pro Thr Leu His Ala Ala
        515                 520                 525

Met Asp Val Asp Gly Pro Ala Val Val Ala Ile Pro Val Asp Tyr Arg
    530                 535                 540

Asp Asn Pro Leu Leu Met Gly Gln Leu His Leu Ser Gln Ile Leu
545                 550                 555

<210> SEQ ID NO 21
<211> LENGTH: 771
<212> TYPE: DNA
<213> ORGANISM: Klebsiella pneumoniae

<400> SEQUENCE: 21
```

```
atgaaaaaag tcgcacttgt taccggcgcc ggccagggga ttggtaaagc tatcgccctt    60
cgtctggtga aggatggatt tgccgtggcc attgccgatt ataacgacgc caccgccaaa   120
gcggtcgcct cggaaatcaa ccaggccggc ggacacgccg tggcggtgaa agtggatgtc   180
tccgaccgcg atcaggtatt tgccgccgtt gaacaggcgc gcaaaacgct gggcggcttc   240
gacgtcatcg tcaataacgc cggtgtggca ccgtctacgc cgatcgagtc cattaccccg   300
gagattgtcg acaaagtcta caacatcaac gtcaaagggg tgatctgggg tattcaggcg   360
gcggtcgagg cctttaagaa agaggggcac ggcgggaaaa tcatcaacgc tgttcccag    420
gccggccacg tcggcaaccc ggagctggcg gtgtatagct ccagtaaatt cgcggtacgc   480
ggcttaaccc agaccgccgc tcgcgacctc gcgccgctgg gcatcaccgt caacggctac   540
tgcccgggga ttgtcaaaac gccaatgtgg gccgaaattg accgccaggt gtccgaagcc   600
gccggtaaac cgctgggcta cggtaccgcc gagttcgcca aacgcatcac tctcggtcgt   660
ctgtccgagc cggaagatgt cgccgcctgc gtctcctatc ttgccagccc ggattctgat   720
tacatgaccg tcagtcgtt gctgatcgac ggcgggatgg tatttaacta a             771
```

<210> SEQ ID NO 22
<211> LENGTH: 256
<212> TYPE: PRT
<213> ORGANISM: Klebsiella pneumoniae

<400> SEQUENCE: 22

```
Met Lys Lys Val Ala Leu Val Thr Gly Ala Gly Gln Gly Ile Gly Lys
1               5                   10                  15

Ala Ile Ala Leu Arg Leu Val Lys Asp Gly Phe Ala Val Ala Ile Ala
            20                  25                  30

Asp Tyr Asn Asp Ala Thr Ala Lys Ala Val Ala Ser Glu Ile Asn Gln
        35                  40                  45

Ala Gly Gly His Ala Val Ala Val Lys Val Asp Val Ser Asp Arg Asp
    50                  55                  60

Gln Val Phe Ala Ala Val Glu Gln Ala Arg Lys Thr Leu Gly Gly Phe
65                  70                  75                  80

Asp Val Ile Val Asn Asn Ala Gly Val Ala Pro Ser Thr Pro Ile Glu
                85                  90                  95

Ser Ile Thr Pro Glu Ile Val Asp Lys Val Tyr Asn Ile Asn Val Lys
            100                 105                 110

Gly Val Ile Trp Gly Ile Gln Ala Ala Val Glu Ala Phe Lys Lys Glu
        115                 120                 125

Gly His Gly Gly Lys Ile Ile Asn Ala Cys Ser Gln Ala Gly His Val
    130                 135                 140

Gly Asn Pro Glu Leu Ala Val Tyr Ser Ser Ser Lys Phe Ala Val Arg
145                 150                 155                 160

Gly Leu Thr Gln Thr Ala Ala Arg Asp Leu Ala Pro Leu Gly Ile Thr
                165                 170                 175

Val Asn Gly Tyr Cys Pro Gly Ile Val Lys Thr Pro Met Trp Ala Glu
            180                 185                 190

Ile Asp Arg Gln Val Ser Glu Ala Ala Gly Lys Pro Leu Gly Tyr Gly
        195                 200                 205

Thr Ala Glu Phe Ala Lys Arg Ile Thr Leu Gly Arg Leu Ser Glu Pro
    210                 215                 220

Glu Asp Val Ala Ala Cys Val Ser Tyr Leu Ala Ser Pro Asp Ser Asp
225                 230                 235                 240
```

Tyr Met Thr Gly Gln Ser Leu Leu Ile Asp Gly Gly Met Val Phe Asn
        245                 250                 255

<210> SEQ ID NO 23
<211> LENGTH: 1665
<212> TYPE: DNA
<213> ORGANISM: Klebsiella oxytoca

<400> SEQUENCE: 23

```
atgagatcga aagatttga agcactggcg aaacgccctg tgaatcagga cggcttcgtt      60
aaggagtgga tcgaagaagg ctttatcgcg atggaaagcc cgaacgaccc aaaaccgtcg     120
attaaaatcg ttaacggcgc ggtgaccgag ctggacggga accggtaag cgattttgac     180
ctgatcgacc actttatcgc cgctacggt atcaacctga accgcgccga agaagtgatg     240
gcgatggatt cggtcaagct ggccaacatg ctgtgcgatc cgaacgttaa acgcagcgaa     300
atcgtcccgc tgaccaccgc gatgacgccg gcgaaaattg tcgaagtggt ttcgcatatg     360
aacgtcgtcg agatgatgat ggcgatgcag aaaatgcgcg cccgccgcac cccgtcccag     420
caggcgcacg tcaccaacgt caaagataac ccggtacaga ttgccgccga cgccgccgaa     480
ggggcatggc gcggatttga cgaacaggaa accaccgttg cggtagcgcg ctatgcgccg     540
ttcaacgcca tcgcgctgct ggtgggctcg caggtaggcc gtccgggcgt gctgacgcag     600
tgctcgctgg aagaagccac cgagctgaag ctcggcatgc tgggccacac ctgctacgcc     660
gaaaccatct ccgtctacgg caccgagccg gtctttaccg acggcgacga cacgccgtgg     720
tcgaagggct cctcgcctc gtcctacgcc tctcgcgggc tgaaaatgcg ctttacctcc     780
ggctccggct cggaagtgca gatgggctac gccgaaggca atccatgct ttatctggaa     840
gcgcgctgca tctacatcac caaagccgcg ggcgtacagg gtctgcaaaa cggttccgta     900
agctgcatcg gcgtgccgtc tgcggtgcct tccggcattc gcgcggtgct ggcggaaaac     960
ctgatctgtt cgtcgctgga tctggagtgc gcctccagca acgaccagac cttcacccac    1020
tccgatatgc gtcgtaccgc gcgcctgctg atgcagttcc tgccgggcac cgactttatc    1080
tcctccggtt attccgcggt gccgaactac gacaacatgt cgccggctc caacgaagat    1140
gccgaagact ttgacgacta caacgtcatc cagcgcgacc tgaaggtgga cggcggtttg    1200
cgtccggttc gcgaagagga cgtcatcgcg atccgtaaca aagccgcccg cgcgctgcag    1260
gccgtgtttg ccggaatggg gctgccgccg attaccgatg aagaagttga agccgcgacc    1320
tacgcccacg gttcgaaaga tatgccggag cgcaacatcg tcgaagacat caagttcgcc    1380
caggaaatca tcaataaaaa ccgcaacggt ctggaagtgg tgaaagcgct ggcgcagggc    1440
ggattcaccg acgtggccca ggacatgctc aacatccaga aagctaagct gaccggggac    1500
tacctgcata cctccgcgat tatcgtcggc gacgggcagg tgctgtcagc cgtcaacgac    1560
gtcaacgact atgccggtcc ggcaacgggc tatcgcctgc agggcgaacg ctgggaagag    1620
attaaaaaca tccctggcgc tcttgatccc aacgagattg attaa                    1665
```

<210> SEQ ID NO 24
<211> LENGTH: 554
<212> TYPE: PRT
<213> ORGANISM: Klebsiella oxytoca

<400> SEQUENCE: 24

Met Arg Ser Lys Arg Phe Glu Ala Leu Ala Lys Arg Pro Val Asn Gln
1               5                   10                  15

Asp Gly Phe Val Lys Glu Trp Ile Glu Glu Gly Phe Ile Ala Met Glu

```
            20                  25                  30
Ser Pro Asn Asp Pro Lys Pro Ser Ile Lys Ile Val Asn Gly Ala Val
            35                  40                  45
Thr Glu Leu Asp Gly Lys Pro Val Ser Asp Phe Asp Leu Ile Asp His
50                  55                  60
Phe Ile Ala Arg Tyr Gly Ile Asn Leu Asn Arg Ala Glu Glu Val Met
65                  70                  75                  80
Ala Met Asp Ser Val Lys Leu Ala Asn Met Leu Cys Asp Pro Asn Val
                85                  90                  95
Lys Arg Ser Glu Ile Val Pro Leu Thr Thr Ala Met Thr Pro Ala Lys
                100                 105                 110
Ile Val Glu Val Val Ser His Met Asn Val Val Glu Met Met Met Ala
                115                 120                 125
Met Gln Lys Met Arg Ala Arg Arg Thr Pro Ser Gln Gln Ala His Val
        130                 135                 140
Thr Asn Val Lys Asp Asn Pro Val Gln Ile Ala Ala Asp Ala Ala Glu
145                 150                 155                 160
Gly Ala Trp Arg Gly Phe Asp Glu Gln Glu Thr Thr Val Ala Val Ala
                165                 170                 175
Arg Tyr Ala Pro Phe Asn Ala Ile Ala Leu Leu Val Gly Ser Gln Val
                180                 185                 190
Gly Arg Pro Gly Val Leu Thr Gln Cys Ser Leu Glu Glu Ala Thr Glu
        195                 200                 205
Leu Lys Leu Gly Met Leu Gly His Thr Cys Tyr Ala Glu Thr Ile Ser
        210                 215                 220
Val Tyr Gly Thr Glu Pro Val Phe Thr Asp Gly Asp Asp Thr Pro Trp
225                 230                 235                 240
Ser Lys Gly Phe Leu Ala Ser Ser Tyr Ala Ser Arg Gly Leu Lys Met
                245                 250                 255
Arg Phe Thr Ser Gly Ser Gly Ser Glu Val Gln Met Gly Tyr Ala Glu
                260                 265                 270
Gly Lys Ser Met Leu Tyr Leu Glu Ala Arg Cys Ile Tyr Ile Thr Lys
                275                 280                 285
Ala Ala Gly Val Gln Gly Leu Gln Asn Gly Ser Val Ser Cys Ile Gly
        290                 295                 300
Val Pro Ser Ala Val Pro Ser Gly Ile Arg Ala Val Leu Ala Glu Asn
305                 310                 315                 320
Leu Ile Cys Ser Ser Leu Asp Leu Glu Cys Ala Ser Ser Asn Asp Gln
                325                 330                 335
Thr Phe Thr His Ser Asp Met Arg Arg Thr Ala Arg Leu Leu Met Gln
                340                 345                 350
Phe Leu Pro Gly Thr Asp Phe Ile Ser Ser Gly Tyr Ser Ala Val Pro
        355                 360                 365
Asn Tyr Asp Asn Met Phe Ala Gly Ser Asn Glu Asp Ala Glu Asp Phe
        370                 375                 380
Asp Asp Tyr Asn Val Ile Gln Arg Asp Leu Lys Val Asp Gly Gly Leu
385                 390                 395                 400
Arg Pro Val Arg Glu Glu Asp Val Ile Ala Ile Arg Asn Lys Ala Ala
                405                 410                 415
Arg Ala Leu Gln Ala Val Phe Ala Gly Met Gly Leu Pro Pro Ile Thr
                420                 425                 430
Asp Glu Glu Val Glu Ala Ala Thr Tyr Ala His Gly Ser Lys Asp Met
        435                 440                 445
```

Pro Glu Arg Asn Ile Val Glu Asp Ile Lys Phe Ala Gln Glu Ile Ile
    450                 455                 460

Asn Lys Asn Arg Asn Gly Leu Glu Val Val Lys Ala Leu Ala Gln Gly
465                 470                 475                 480

Gly Phe Thr Asp Val Ala Gln Asp Met Leu Asn Ile Gln Lys Ala Lys
                485                 490                 495

Leu Thr Gly Asp Tyr Leu His Thr Ser Ala Ile Ile Val Gly Asp Gly
            500                 505                 510

Gln Val Leu Ser Ala Val Asn Asp Val Asn Asp Tyr Ala Gly Pro Ala
        515                 520                 525

Thr Gly Tyr Arg Leu Gln Gly Glu Arg Trp Glu Glu Ile Lys Asn Ile
    530                 535                 540

Pro Gly Ala Leu Asp Pro Asn Glu Ile Asp
545                 550

<210> SEQ ID NO 25
<211> LENGTH: 675
<212> TYPE: DNA
<213> ORGANISM: Klebsiella oxytoca

<400> SEQUENCE: 25
atggaaatta atgaaaaatt gctgcgccag ataattgaag acgtgctcag cgagatgaag    60
ggcagcgata aaccggtctc gtttaatgcg ccggcggcct ccgcggcgcc ccaggccacg   120
ccgcccgccg cgacggcttc cctgacggaa gtgggcgaag cgcgtcaggg aacccagcag   180
gacgaagtga ttatcgccgt cggcccggct ttcggcctgg cgcagaccgt caatatcgtc   240
ggcatcccgc ataagagcat tttgcgcgaa gtcattgccg gtattgaaga agaaggcatt   300
aaggcgcgcg tgattcgctg ctttaaatcc tccgacgtgg ccttcgtcgc cgttgaaggt   360
aatcgcctga gcggctccgg catctctatc ggcatccagt cgaaaggcac cacggtgatc   420
caccagcagg gctgccgcc gctctctaac ctggagctgt ccccgcaggc gccgctgctg   480
accctggaaa cctatcgcca gatcggcaaa aacgccgccc gctatgcgaa acgcgaatcg   540
ccgcagccgg tcccgacgct gaatgaccag atggcgcggc cgaagtacca ggcgaaatcg   600
gccattttgc acattaaaga gaccaagtac gtggtgacgg gcaaaaaccc gcaggaactg   660
cgcgtggcgc tttga                                                   675

<210> SEQ ID NO 26
<211> LENGTH: 224
<212> TYPE: PRT
<213> ORGANISM: Klebsiella oxytoca

<400> SEQUENCE: 26

Met Glu Ile Asn Glu Lys Leu Leu Arg Gln Ile Ile Glu Asp Val Leu
1               5                   10                  15

Ser Glu Met Lys Gly Ser Asp Lys Pro Val Ser Phe Asn Ala Pro Ala
            20                  25                  30

Ala Ser Ala Ala Pro Gln Ala Thr Pro Pro Ala Gly Asp Gly Phe Leu
        35                  40                  45

Thr Glu Val Gly Glu Ala Arg Gln Gly Thr Gln Asp Glu Val Ile
    50                  55                  60

Ile Ala Val Gly Pro Ala Phe Gly Leu Ala Gln Thr Val Asn Ile Val
65                  70                  75                  80

Gly Ile Pro His Lys Ser Ile Leu Arg Glu Val Ile Ala Gly Ile Glu
            85                  90                  95

Glu Glu Gly Ile Lys Ala Arg Val Ile Arg Cys Phe Lys Ser Ser Asp
                100                 105                 110

Val Ala Phe Val Ala Val Glu Gly Asn Arg Leu Ser Gly Ser Gly Ile
            115                 120                 125

Ser Ile Gly Ile Gln Ser Lys Gly Thr Thr Val Ile His Gln Gln Gly
130                 135                 140

Leu Pro Pro Leu Ser Asn Leu Glu Leu Phe Pro Gln Ala Pro Leu Leu
145                 150                 155                 160

Thr Leu Glu Thr Tyr Arg Gln Ile Gly Lys Asn Ala Ala Arg Tyr Ala
                165                 170                 175

Lys Arg Glu Ser Pro Gln Pro Val Pro Thr Leu Asn Asp Gln Met Ala
            180                 185                 190

Arg Pro Lys Tyr Gln Ala Lys Ser Ala Ile Leu His Ile Lys Glu Thr
        195                 200                 205

Lys Tyr Val Val Thr Gly Lys Asn Pro Gln Glu Leu Arg Val Ala Leu
210                 215                 220

<210> SEQ ID NO 27
<211> LENGTH: 522
<212> TYPE: DNA
        <213> ORGANISM: Klebsiella oxytoca

<400> SEQUENCE: 27
atgaataccg acgcaattga atcgatggta cgcgacgtat tgagccgcat gaacagcctg        60
cagggcgagg cgcctgcggc ggctccggcg gctggcggcg cgtcccgtag cgccagggtc       120
agcgactacc cgctggcgaa caagcacccg gaatgggtga aaccgccac caataaaacg        180 ctggacgact ttacgctgga aaacgtgctg agcaataaag tcaccgccca ggatatgcgt       240
attaccccgg aaaccctgcg cttacaggct tctattgcca agacgcgggg ccgcgaccgg       300
ctggcgatga acttcgagcg cgccgccgag ctgaccgcgg taccgacga tcgcattctt        360 gaaatctaca cgccctccg ccctatcgc tcgacgaaag aggagctgct ggcgatcgcc        420
gacgatctcg aaagccgcta tcaggcgaag atttgcgccg ctttcgttcg cgaagcggcc       480
acgctgtacg tcgagcgtaa aaaactcaaa ggcgacgatt aa                          522

<210> SEQ ID NO 28
<211> LENGTH: 173
<212> TYPE: PRT
<213> ORGANISM: Klebsiella oxytoca

<400> SEQUENCE: 28

Met Asn Thr Asp Ala Ile Glu Ser Met Val Arg Asp Val Leu Ser Arg
1               5                   10                  15

Met Asn Ser Leu Gln Gly Glu Ala Pro Ala Ala Pro Ala Ala Gly
            20                  25                  30

Gly Ala Ser Arg Ser Ala Arg Val Ser Asp Tyr Pro Leu Ala Asn Lys
        35                  40                  45

His Pro Glu Trp Val Lys Thr Ala Thr Asn Lys Thr Leu Asp Asp Phe
    50                  55                  60

Thr Leu Glu Asn Val Leu Ser Asn Lys Val Thr Ala Gln Asp Met Arg
65                  70                  75                  80

Ile Thr Pro Glu Thr Leu Arg Leu Gln Ala Ser Ile Ala Lys Asp Ala
                85                  90                  95

Gly Arg Asp Arg Leu Ala Met Asn Phe Glu Arg Ala Ala Glu Leu Thr
            100                 105                 110

Ala Val Pro Asp Asp Arg Ile Leu Glu Ile Tyr Asn Ala Leu Arg Pro
         115                 120                 125

Tyr Arg Ser Thr Lys Glu Glu Leu Leu Ala Ile Ala Asp Asp Leu Glu
        130                 135                 140

Ser Arg Tyr Gln Ala Lys Ile Cys Ala Ala Phe Val Arg Glu Ala Ala
145                 150                 155                 160

Thr Leu Tyr Val Glu Arg Lys Lys Leu Lys Gly Asp Asp
                165                 170

<210> SEQ ID NO 29
<211> LENGTH: 1041
<212> TYPE: DNA
<213> ORGANISM: Rhodococcus ruber

<400> SEQUENCE: 29

```
atgaaagccc tccagtacac cgagatcggc tccgagccgg tcgtcgtcga cgtccccacc      60
ccggcgcccg ggccgggtga gatcctgctg aaggtcaccg cggccggctt gtgccactcg     120
gacatcttcg tgatggacat gccggcagag cagtacatct acggtcttcc cctcacccte     180
ggccacgagg gcgtcggcac cgtcgccgaa ctcggcgccg cgtcaccgg attcgagacg      240
ggggacgccg tcgccgtgta cgggccgtgg gggtgcggtg cgtgccacgc gtgcgcgcgc     300
ggccgggaga actactgcac ccgcgccgcc gagctgggca tcaccccgcc cggtctcggc     360
tcgcccgggt cgatggccga gtacatgatc gtcgactcgg cgcgccacct cgtcccgatc     420
ggggacctcg accccgtcgc ggcggttccg ctcaccgacg cgggcctgac gccgtaccac     480
gcgatctcgc gggtcctgcc cctgctggga cccggctcga ccgcggtcgt catcggggtc     540
ggcggactcg gcacgtcgg catccagatc ctgcgcgccg tcagcgcggc ccgcgtgatc     600
gccgtcgatc tcgacgacga ccgactcgcg ctcgcccgcg aggtcggcgc cgacgcggcg     660
gtgaagtcgg cgccggggc ggcggacgcg atccgggagc tgaccggcgg tgagggcgcg     720
acggcggtgt cgacttcgt cggcgcccag tcgacgatcg acacggcgca gcaggtggtc     780
gcgatcgacg ggcacatctc ggtggtcggc atccatgccg cgcccacgc caaggtcggc     840
ttcttcatga tcccgttcgg cgcgtccgtc gtgacgccgt actggggcac gcggtccgag     900
ctgatggacg tcgtggacct ggcccgtgcc ggccggctcg acatccacac cgagacgttc     960
accctcgacg agggacccac ggcctaccgg cggctacgcg agggcagcat ccgcggccgc    1020
ggggtggtcg tcccgggctg a                                              1041
```

<210> SEQ ID NO 30
<211> LENGTH: 346
<212> TYPE: PRT
<213> ORGANISM: Rhodococcus ruber

<400> SEQUENCE: 30

Met Lys Ala Leu Gln Tyr Thr Glu Ile Gly Ser Glu Pro Val Val Val
1               5                   10                  15

Asp Val Pro Thr Pro Ala Pro Gly Pro Gly Glu Ile Leu Leu Lys Val
            20                  25                  30

Thr Ala Ala Gly Leu Cys His Ser Asp Ile Phe Val Met Asp Met Pro
        35                  40                  45

Ala Glu Gln Tyr Ile Tyr Gly Leu Pro Leu Thr Leu Gly His Glu Gly
    50                  55                  60

Val Gly Thr Val Ala Glu Leu Gly Ala Gly Val Thr Gly Phe Glu Thr
65                  70                  75                  80

Gly Asp Ala Val Ala Val Tyr Gly Pro Trp Gly Cys Gly Ala Cys His
                85                  90                  95

Ala Cys Ala Arg Gly Arg Glu Asn Tyr Cys Thr Arg Ala Ala Glu Leu
            100                 105                 110

Gly Ile Thr Pro Pro Gly Leu Gly Ser Pro Gly Ser Met Ala Glu Tyr
        115                 120                 125

Met Ile Val Asp Ser Ala Arg His Leu Val Pro Ile Gly Asp Leu Asp
    130                 135                 140

Pro Val Ala Ala Val Pro Leu Thr Asp Ala Gly Leu Thr Pro Tyr His
145                 150                 155                 160

Ala Ile Ser Arg Val Leu Pro Leu Leu Gly Pro Gly Ser Thr Ala Val
                165                 170                 175

Val Ile Gly Val Gly Gly Leu Gly His Val Gly Ile Gln Ile Leu Arg
            180                 185                 190

Ala Val Ser Ala Ala Arg Val Ile Ala Val Asp Leu Asp Asp Asp Arg
        195                 200                 205

Leu Ala Leu Ala Arg Glu Val Gly Ala Asp Ala Ala Val Lys Ser Gly
    210                 215                 220

Ala Gly Ala Ala Asp Ala Ile Arg Glu Leu Thr Gly Gly Glu Gly Ala
225                 230                 235                 240

Thr Ala Val Phe Asp Phe Val Gly Ala Gln Ser Thr Ile Asp Thr Ala
                245                 250                 255

Gln Gln Val Val Ala Ile Asp Gly His Ile Ser Val Val Gly Ile His
            260                 265                 270

Ala Gly Ala His Ala Lys Val Gly Phe Phe Met Ile Pro Phe Gly Ala
        275                 280                 285

Ser Val Val Thr Pro Tyr Trp Gly Thr Arg Ser Glu Leu Met Asp Val
    290                 295                 300

Val Asp Leu Ala Arg Ala Gly Arg Leu Asp Ile His Thr Glu Thr Phe
305                 310                 315                 320

Thr Leu Asp Glu Gly Pro Thr Ala Tyr Arg Arg Leu Arg Glu Gly Ser
                325                 330                 335

Ile Arg Gly Arg Gly Val Val Val Pro Gly
            340                 345

<210> SEQ ID NO 31
<211> LENGTH: 1476
<212> TYPE: DNA
<213> ORGANISM: Escherichia coli

<400> SEQUENCE: 31
atggctaact acttcaatac actgaatctg cgccagcagc tggcacagct gggcaaatgt      60
cgctttatgg ccgcgatga attcgccgat ggcgcgagct accttcaggg taaaaaagta     120
gtcatcgtcg gctgtggcgc acagggtctg aaccagggcc tgaacatgcg tgattctggt     180
ctcgatatct cctacgctct gcgtaaagaa gcgattgccg agaagcgcgc gtcctggcgt     240
aaagcgaccg aaaatggttt taaagtgggt acttacgaag aactgatccc acaggcggat     300
ctggtgatta acctgacgcc ggacaagcag cactctgatg tagtgcgcac cgtacagcca     360
ctgatgaaag acggcgcggc gctgggctac tcgcacggtt tcaacatcgt cgaagtgggc     420
gagcagatcc gtaaagatat caccgtagtg atggttgcgc cgaaatgccc aggcaccgaa     480
gtgcgtgaaa gtacaaacg tgggttcggc gtaccgacgc tgattgccgt tcacccggaa     540
aacgatccga aggcgaagg catggcgatt gccaaagcct gggcggctgc aaccggtggt     600

```
caccgtgcgg gtgtgctgga atcgtccttc gttgcggaag tgaaatctga cctgatgggc    660
gagcaaacca tcctgtgcgg tatgttgcag gctggctctc tgctgtgctt cgacaagctg    720
gtggaagaag gtaccgatcc agcatacgca gaaaaactga ttcagttcgg ttgggaaacc    780
atcaccgaaa cactgaaaca gggcggcatc accctgatga tggaccgtct ctctaacccg    840
gcgaaactgc gtgcttatgc gctttctgaa cagctgaaag agatcatggc accctgttc    900 cagaaacata tggacgacat catctccggc gaattctctt ccggtatgat ggcggactgg    960
gccaacgatg ataagaaact gctgacctgg cgtgaagaga ccggcaaaac cgcgtttgaa   1020
accgcgccgc agtatgaagg caaaatcggc gagcaggagt acttcgataa aggcgtactg   1080
atgattgcga tggtgaaagc gggcgttgaa ctggcgttcg aaaccatggt cgattccggc   1140
atcattgaag agtctgcata ttatgaatca ctgcacgagc tgccgctgat tgccaacacc   1200
atcgcccgta agcgtctgta cgaaatgaac gtggttatct ctgataccgc tgagtacggt   1260
aactatctgt tctcttacgc ttgtgtgccg ttgctgaaac cgtttatggc agagctgcaa   1320
ccgggcgacc tgggtaaagc tattccggaa ggcgcggtag ataacgggca actgcgtgat   1380
gtgaacgaag cgattcgcag ccatgcgatt gagcaggtag gtaagaaact gcgcggctat   1440
atgacagata tgaaacgtat tgctgttgcg ggttaa                              1476
```

<210> SEQ ID NO 32
<211> LENGTH: 491
<212> TYPE: PRT
<213> ORGANISM: Escherichia coli

<400> SEQUENCE: 32

```
Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
                20                  25                  30

Ser Tyr Leu Gln Gly Lys Val Val Ile Val Gly Cys Gly Ala Gln
            35                  40                  45

Gly Leu Asn Gln Gly Leu Asn Met Arg Asp Ser Gly Leu Asp Ile Ser
        50                  55                  60

Tyr Ala Leu Arg Lys Glu Ala Ile Ala Glu Lys Arg Ala Ser Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Gln His Ser
                100                 105                 110

Asp Val Val Arg Thr Val Gln Pro Leu Met Lys Asp Gly Ala Ala Leu
            115                 120                 125

Gly Tyr Ser His Gly Phe Asn Ile Val Glu Val Gly Glu Gln Ile Arg
        130                 135                 140

Lys Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
            180                 185                 190

Ala Trp Ala Ala Ala Thr Gly Gly His Arg Ala Gly Val Leu Glu Ser
        195                 200                 205

Ser Phe Val Ala Glu Val Lys Ser Asp Leu Met Gly Glu Gln Thr Ile
```

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
            245                 250                 255

Gly Trp Glu Thr Ile Thr Glu Ala Leu Lys Gln Gly Gly Ile Thr Leu
                260                 265                 270

Met Met Asp Arg Leu Ser Asn Pro Ala Lys Leu Arg Ala Tyr Ala Leu
            275                 280                 285

Ser Glu Gln Leu Lys Glu Ile Met Ala Pro Leu Phe Gln Lys His Met
290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
                325                 330                 335

Thr Ala Phe Glu Thr Ala Pro Gln Tyr Glu Gly Lys Ile Gly Glu Gln
            340                 345                 350

Glu Tyr Phe Asp Lys Gly Val Leu Met Ile Ala Met Val Lys Ala Gly
            355                 360                 365

Val Glu Leu Ala Phe Glu Thr Met Val Asp Ser Gly Ile Ile Glu Glu
            370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
                405                 410                 415

Ala Glu Tyr Gly Asn Tyr Leu Phe Ser Tyr Ala Cys Val Pro Leu Leu
            420                 425                 430

Lys Pro Phe Met Ala Glu Leu Gln Pro Gly Asp Leu Gly Lys Ala Ile
            435                 440                 445

Pro Glu Gly Ala Val Asp Asn Gly Gln Leu Arg Asp Val Asn Glu Ala
450                 455                 460

Ile Arg Ser His Ala Ile Glu Gln Val Gly Lys Lys Leu Arg Gly Tyr
465                 470                 475                 480

Met Thr Asp Met Lys Arg Ile Ala Val Ala Gly
                485                 490

<210> SEQ ID NO 33
<211> LENGTH: 1851
<212> TYPE: DNA
<213> ORGANISM: Escherichia coli

<400> SEQUENCE: 33
atgcctaagt accgttccgc caccaccact catggtcgta atatggcggg tgctcgtgcg    60
ctgtggcgcg ccaccggaat gaccgacgcc gatttcggta agccgattat cgcggttgtg   120
aactcgttca cccaatttgt accgggtcac gtccatctgc gcgatctcgg taaactggtc   180
gccgaacaaa ttgaagcggc tggcggcgtt gccaaagagt tcaacaccat gcggtggat   240 gatgggattg ccatgggcca cggggggatg ctttattcac tgccatctcg cgaactgatc   300
gctgattccg ttgagtatat ggtcaacgcc cactgcgccg acgccatggt ctgcatctct   360
aactgcgaca aaatcacccc gggatgctg atggcttccc tgcgcctgaa tattccggtg   420
atctttgttt ccggcggccc gatggaggcc gggaaaacca acttccga tcagatcatc   480 aagctcgatc tggttgatgc gatgatccag ggcgcagacc cgaaagtatc tgactcccag   540

```
agcgatcagg ttgaacgttc cgcgtgtccg acctgcggtt cctgctccgg gatgtttacc    600
gctaactcaa tgaactgcct gaccgaagcg ctgggcctgt cgcagccggg caacggctcg    660
ctgctggcaa cccacgccga ccgtaagcag ctgttcctta atgctggtaa acgcattgtt    720
gaattgacca aacgttatta cgagcaaaac gacgaaagtg cactgccgcg taatatcgcc    780
agtaaggcgg cgtttgaaaa cgccatgacg ctggatatcg cgatgggtgg atcgactaac    840
accgtacttc acctgctggc ggcggcgcag gaagcggaaa tcgacttcac catgagtgat    900
atcgataagc tttcccgcaa ggttccacag ctgtgtaaag ttgcgccgag cacccagaaa    960
taccatatgg aagatgttca ccgtgctggt ggtgttatcg gtattctcgg cgaactggat   1020
cgcgcggggt tactgaaccg tgatgtgaaa aacgtacttg gcctgacgtt gccgcaaacg   1080
ctggaacaat acgacgttat gctgacccag gatgacgcgg taaaaaatat gttccgcgca   1140
ggtcctgcag gcattcgtac cacacaggca ttctcgcaag attgccgttg ggatacgctg   1200
gacgacgatc gcgccaatgg ctgtatccgc tcgctggaac acgcctacag caaagacggc   1260
ggcctggcgg tgctctacgg taactttgcg gaaaacggct gcatcgtgaa aacggcaggc   1320
gtcgatgaca gcatcctcaa attcaccggc ccggcgaaag tgtacgaaag ccaggacgat   1380
gcggtagaag cgattctcgg cggtaaagtt gtcgccggag atgtggtagt aattcgctat   1440
gaaggcccga aggcggtcc ggggatgcag gaaatgctct acccaaccag cttcctgaaa   1500
tcaatgggtc tcggcaaagc ctgtgcgctg atcaccgacg tcgtttctc tggtggcacc   1560
tctggtcttt ccatcggcca cgtctcaccg gaagcggcaa gcggcggcag cattggcctg   1620
attgaagatg gtgacctgat cgctatcgac atcccgaacc gtggcattca gttacaggta   1680
agcgatgccg aactggcggc gcgtcgtgaa gcgcaggacg ctcgaggtga caaagcctgg   1740
acgccgaaaa atcgtgaacg tcaggtctcc tttgccctgc gtgcttatgc cagcctggca   1800
accagcgccg acaaaggcgc ggtgcgcgat aaatcgaaac tgggggggtta a           1851
```

<210> SEQ ID NO 34  
<211> LENGTH: 616  
<212> TYPE: PRT  
<213> ORGANISM: Escherichia coli

<400> SEQUENCE: 34

```
Met Pro Lys Tyr Arg Ser Ala Thr Thr Thr His Gly Arg Asn Met Ala
1               5                   10                  15

Gly Ala Arg Ala Leu Trp Arg Ala Thr Gly Met Thr Asp Ala Asp Phe
            20                  25                  30

Gly Lys Pro Ile Ile Ala Val Val Asn Ser Phe Thr Gln Phe Val Pro
        35                  40                  45

Gly His Val His Leu Arg Asp Leu Gly Lys Leu Val Ala Glu Gln Ile
    50                  55                  60

Glu Ala Ala Gly Gly Val Ala Lys Glu Phe Asn Thr Ile Ala Val Asp
65                  70                  75                  80

Asp Gly Ile Ala Met Gly His Gly Gly Met Leu Tyr Ser Leu Pro Ser
                85                  90                  95

Arg Glu Leu Ile Ala Asp Ser Val Glu Tyr Met Val Asn Ala His Cys
            100                 105                 110

Ala Asp Ala Met Val Cys Ile Ser Asn Cys Asp Lys Ile Thr Pro Gly
        115                 120                 125

Met Leu Met Ala Ser Leu Arg Leu Asn Ile Pro Val Ile Phe Val Ser
    130                 135                 140
```

```
Gly Gly Pro Met Glu Ala Gly Lys Thr Lys Leu Ser Asp Gln Ile Ile
145                 150                 155                 160

Lys Leu Asp Leu Val Asp Ala Met Ile Gln Gly Ala Asp Pro Lys Val
                165                 170                 175

Ser Asp Ser Gln Ser Asp Gln Val Glu Arg Ser Ala Cys Pro Thr Cys
                180                 185                 190

Gly Ser Cys Ser Gly Met Phe Thr Ala Asn Ser Met Asn Cys Leu Thr
                195                 200                 205

Glu Ala Leu Gly Leu Ser Gln Pro Gly Asn Gly Ser Leu Leu Ala Thr
210                 215                 220

His Ala Asp Arg Lys Gln Leu Phe Leu Asn Ala Gly Lys Arg Ile Val
225                 230                 235                 240

Glu Leu Thr Lys Arg Tyr Tyr Glu Gln Asn Asp Glu Ser Ala Leu Pro
                245                 250                 255

Arg Asn Ile Ala Ser Lys Ala Ala Phe Glu Asn Ala Met Thr Leu Asp
                260                 265                 270

Ile Ala Met Gly Gly Ser Thr Asn Thr Val Leu His Leu Leu Ala Ala
                275                 280                 285

Ala Gln Glu Ala Glu Ile Asp Phe Thr Met Ser Asp Ile Asp Lys Leu
290                 295                 300

Ser Arg Lys Val Pro Gln Leu Cys Lys Val Ala Pro Ser Thr Gln Lys
305                 310                 315                 320

Tyr His Met Glu Asp Val His Arg Ala Gly Gly Val Ile Gly Ile Leu
                325                 330                 335

Gly Glu Leu Asp Arg Ala Gly Leu Leu Asn Arg Asp Val Lys Asn Val
                340                 345                 350

Leu Gly Leu Thr Leu Pro Gln Thr Leu Glu Gln Tyr Asp Val Met Leu
                355                 360                 365

Thr Gln Asp Asp Ala Val Lys Asn Met Phe Arg Ala Gly Pro Ala Gly
                370                 375                 380

Ile Arg Thr Thr Gln Ala Phe Ser Gln Asp Cys Arg Trp Asp Thr Leu
385                 390                 395                 400

Asp Asp Asp Arg Ala Asn Gly Cys Ile Arg Ser Leu Glu His Ala Tyr
                405                 410                 415

Ser Lys Asp Gly Gly Leu Ala Val Leu Tyr Gly Asn Phe Ala Glu Asn
                420                 425                 430

Gly Cys Ile Val Lys Thr Ala Gly Val Asp Asp Ser Ile Leu Lys Phe
                435                 440                 445

Thr Gly Pro Ala Lys Val Tyr Glu Ser Gln Asp Asp Ala Val Glu Ala
                450                 455                 460

Ile Leu Gly Gly Lys Val Val Ala Gly Asp Val Val Val Ile Arg Tyr
465                 470                 475                 480

Glu Gly Pro Lys Gly Gly Pro Gly Met Gln Glu Met Leu Tyr Pro Thr
                485                 490                 495

Ser Phe Leu Lys Ser Met Gly Leu Gly Lys Ala Cys Ala Leu Ile Thr
                500                 505                 510

Asp Gly Arg Phe Ser Gly Gly Thr Ser Gly Leu Ser Ile Gly His Val
                515                 520                 525

Ser Pro Glu Ala Ala Ser Gly Ser Ile Gly Leu Ile Glu Asp Gly
                530                 535                 540

Asp Leu Ile Ala Ile Asp Ile Pro Asn Arg Gly Ile Gln Leu Gln Val
545                 550                 555                 560

Ser Asp Ala Glu Leu Ala Ala Arg Arg Glu Ala Gln Asp Ala Arg Gly
```

565                 570                 575
Asp Lys Ala Trp Thr Pro Lys Asn Arg Glu Arg Gln Val Ser Phe Ala
        580                 585                 590
Leu Arg Ala Tyr Ala Ser Leu Ala Thr Ser Ala Asp Lys Gly Ala Val
        595                 600                 605
Arg Asp Lys Ser Lys Leu Gly Gly
        610             615

<210> SEQ ID NO 35
<211> LENGTH: 1647
<212> TYPE: DNA
<213> ORGANISM: Lactococcus lactis

<400> SEQUENCE: 35

| | | | | | |
|---|---|---|---|---|---|
| atgtatactg | tgggggatta | cctgctggat | cgcctgcacg | aactgggdat | tgaagaaatt | 60 |
| ttcggtgtgc | aggcgattta | aacctgcag | ttcctggacc | agattatctc | gcacaaagat | 120 |
| atgaagtggg | tcgtaacgc | caacgaactg | aacgcgagct | atatggcaga | tggttatgcc | 180 |
| cgtaccaaaa | aagctgctgc | gtttctgacg | acctttggcg | ttggcgaact | gagcgccgtc | 240 |
| aacggactgg | caggaagcta | cgccgagaac | ctgccagttg | tcgaaattgt | tgggtcgcct | 300 |
| acttctaagg | ttcagaatga | aggcaaattt | gtgcaccata | ctctggctga | tggggatttt | 360 |
| aaacatttta | tgaaaatgca | tgaaccggtt | actgcggccc | gcacgctgct | gacagcagag | 420 |
| aatgctacgg | ttgagatcga | ccgcgtcctg | tctgcgctgc | tgaaagagcg | caagccggta | 480 |
| tatatcaatc | tgcctgtcga | tgttgccgca | gcgaaagccg | aaaagccgtc | gctgccactg | 540 |
| aaaaaagaaa | acagcacctc | caatacatcg | gaccaggaaa | ttctgaataa | aatccaggaa | 600 |
| tcactgaaga | atgcgaagaa | accgatcgtc | atcaccggac | atgagatcat | ctcttttggc | 660 |
| ctggaaaaaa | cggtcacgca | gttcatttct | aagaccaaac | tgcctatcac | caccctgaac | 720 |
| ttcggcaaat | ctagcgtcga | tgaagcgctg | ccgagttttc | tgggtatcta | taatggtacc | 780 |
| ctgtccgaac | cgaacctgaa | agaattcgtc | gaaagcgcgg | actttatcct | gatgctgggc | 840 |
| gtgaaactga | cggatagctc | cacaggcgca | tttacccacc | atctgaacga | aataaaatg | 900 |
| atttccctga | atatcgacga | aggcaaaatc | tttaacgagc | gcatccagaa | cttcgatttt | 960 |
| gaatctctga | ttagttcgct | gctggatctg | tccgaaattg | agtataaagg | taaatatatt | 1020 |
| gataaaaaac | aggaggattt | tgtgccgtct | aatgcgctgc | tgagtcagga | tcgtctgtgg | 1080 |
| caagccgtag | aaaacctgac | acagtctaat | gaaacgattg | ttgcggaaca | gggaacttca | 1140 |
| ttttcggcg | cctcatccat | ttttctgaaa | tccaaaagcc | atttcattgg | ccaaccgctg | 1200 |
| tgggggagta | ttggttatac | ctttccggcg | gcgctgggtt | cacagattgc | agataaggaa | 1260 |
| tcacgccatc | tgctgtttat | tggtgacggc | agcctgcagc | tgactgtcca | ggaactgggg | 1320 |
| ctggcgatcc | gtgaaaaaat | caatccgatt | tgctttatca | tcaataacga | cggctacacc | 1380 |
| gtcgaacgcg | aaattcatgg | accgaatcaa | agttacaatg | catcccgat | gtggaactat | 1440 |
| agcaaactgc | cggaatcctt | tggcgcgaca | gaggatcgcg | tggtgagtaa | aattgtgcgt | 1500 |
| acggaaaacg | aatttgtgtc | ggttatgaaa | gaagcgcagg | ctgacccgaa | tcgcatgtat | 1560 |
| tggattgaac | tgatcctggc | aaaagaaggc | gcaccgaaag | ttctgaaaaa | gatggggaaa | 1620 |
| ctgtttgcgg | agcaaaataa | aagctaa | | | | 1647 |

<210> SEQ ID NO 36
<211> LENGTH: 548
<212> TYPE: PRT

<213> ORGANISM: Lactococcus lactis

<400> SEQUENCE: 36

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Lys Thr
    210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Thr Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asn Glu Asn Lys Met Ile Ser Leu Asn
    290                 295                 300

Ile Asp Glu Gly Lys Ile Phe Asn Glu Arg Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
        355                 360                 365

Ser Asn Glu Thr Ile Val Ala Glu Gln Gly Thr Ser Phe Phe Gly Ala
    370                 375                 380

Ser Ser Ile Phe Leu Lys Ser Lys Ser His Phe Ile Gly Gln Pro Leu
385                 390                 395                 400

Trp Gly Ser Ile Gly Tyr Thr Phe Pro Ala Ala Leu Gly Ser Gln Ile
            405                 410                 415

Ala Asp Lys Glu Ser Arg His Leu Leu Phe Ile Gly Asp Gly Ser Leu
        420                 425                 430

Gln Leu Thr Val Gln Glu Leu Gly Leu Ala Ile Arg Glu Lys Ile Asn
    435                 440                 445

Pro Ile Cys Phe Ile Ile Asn Asn Asp Gly Tyr Thr Val Glu Arg Glu
450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
                485                 490                 495

Lys Ile Val Arg Thr Glu Asn Glu Phe Val Ser Val Met Lys Glu Ala
                500                 505                 510

Gln Ala Asp Pro Asn Arg Met Tyr Trp Ile Glu Leu Ile Leu Ala Lys
            515                 520                 525

Glu Gly Ala Pro Lys Val Leu Lys Lys Met Gly Lys Leu Phe Ala Glu
        530                 535                 540

Gln Asn Lys Ser
545

<210> SEQ ID NO 37
<211> LENGTH: 1164
<212> TYPE: DNA
<213> ORGANISM: Escherichia coli

<400> SEQUENCE: 37

| | | | | |
|---|---|---|---|---|
| atgaacaact | ttaatctgca | caccccaacc | cgcattctgt | ttggtaaagg cgcaatcgct | 60 |
| ggtttacgcg | aacaaattcc | tcacgatgct | cgcgtattga | ttacctacgg cggcggcagc | 120 |
| gtgaaaaaaa | ccggcgttct | cgatcaagtt | ctggatgccc | tgaaaggcat ggacgtgctg | 180 |
| gaatttggcg | gtattgagcc | aaacccggct | tatgaaacgc | tgatgaacgc cgtgaaactg | 240 |
| gttcgcgaac | agaaagtgac | tttcctgctg | gcggttggcg | gcggttctgt actggacggc | 300 |
| accaaattta | tcgccgcagc | ggctaactat | ccggaaaata | tcgatccgtg cacattctg | 360 |
| caaacgggcg | gtaaagagat | taaaagcgcc | atcccgatgg | gctgtgtgct gacgctgcca | 420 |
| gcaaccggtt | cagaatccaa | cgcaggcgcg | gtgatctccc | gtaaaaccac aggcgacaag | 480 |
| caggcgttcc | attctgccca | tgttcagccg | gtatttgccg | tgctcgatcc ggtttatacc | 540 |
| tacaccctgc | cgccgcgtca | ggtggctaac | ggcgtagtgg | acgcctttgt acacaccgtg | 600 |
| gaacagtatg | ttaccaaacc | ggttgatgcc | aaaattcagg | accgtttcgc agaaggcatt | 660 |
| ttgctgacgc | taatcgaaga | tggtccgaaa | gccctgaaag | agccagaaaa ctacgatgtg | 720 |
| cgcgccaacg | tcatgtgggc | ggcgactcag | gcgctgaacg | gtttgattgg cgctggcgta | 780 |
| ccgcaggact | gggcaacgca | tatgctgggc | acgaactga | ctgcgatgca cggtctggat | 840 |
| cacgcgcaaa | cactggctat | cgtcctgcct | gcactgtgga | atgaaaaacg cgataccaag | 900 |
| cgcgctaagc | tgctgcaata | tgctgaacgc | gtctggaaca | tcactgaagg ttccgatgat | 960 |
| gagcgtattg | acgccgcgat | tgccgcaacc | cgcaatttct | ttgagcaatt aggcgtgccg | 1020 |
| acccacctct | ccgactacgg | tctggacggc | agctccatcc | cggctttgct gaaaaaactg | 1080 |
| gaagagcacg | gcatgaccca | actgggcgaa | aatcatgaca | ttacgttgga tgtcagccgc | 1140 |
| cgtatatacg | aagccgcccg | ctaa | | | 1164 |

```
<210> SEQ ID NO 38
<211> LENGTH: 387
<212> TYPE: PRT
<213> ORGANISM: Escherichia coli

<400> SEQUENCE: 38
```

| | | | | | | | | | | | | | | |
|---|---|---|---|---|---|---|---|---|---|---|---|---|---|---|
| Met | Asn | Asn | Phe | Asn | Leu | His | Thr | Pro | Thr | Arg | Ile | Leu | Phe | Gly | Lys |
| 1 | | | | 5 | | | | | 10 | | | | | 15 | |
| Gly | Ala | Ile | Ala | Gly | Leu | Arg | Glu | Gln | Ile | Pro | His | Asp | Ala | Arg | Val |
| | | | 20 | | | | | 25 | | | | | 30 | | |
| Leu | Ile | Thr | Tyr | Gly | Gly | Ser | Val | Lys | Thr | Gly | Val | Leu | Asp |
| | | | 35 | | | | 40 | | | | | 45 | |
| Gln | Val | Leu | Asp | Ala | Leu | Lys | Gly | Met | Asp | Val | Leu | Glu | Phe | Gly | Gly |
| | 50 | | | | | 55 | | | | | 60 | | | | |
| Ile | Glu | Pro | Asn | Pro | Ala | Tyr | Glu | Thr | Leu | Met | Asn | Ala | Val | Lys | Leu |
| 65 | | | | | 70 | | | | | 75 | | | | | 80 |
| Val | Arg | Glu | Gln | Lys | Val | Thr | Phe | Leu | Leu | Ala | Val | Gly | Gly | Gly | Ser |
| | | | | 85 | | | | | 90 | | | | | 95 | |
| Val | Leu | Asp | Gly | Thr | Lys | Phe | Ile | Ala | Ala | Ala | Asn | Tyr | Pro | Glu |
| | | | 100 | | | | | 105 | | | | | 110 | |
| Asn | Ile | Asp | Pro | Trp | His | Ile | Leu | Gln | Thr | Gly | Gly | Lys | Glu | Ile | Lys |
| | | | 115 | | | | | 120 | | | | | 125 | | |
| Ser | Ala | Ile | Pro | Met | Gly | Cys | Val | Leu | Thr | Leu | Pro | Ala | Thr | Gly | Ser |
| 130 | | | | | 135 | | | | | 140 | | | | | |
| Glu | Ser | Asn | Ala | Gly | Ala | Val | Ile | Ser | Arg | Lys | Thr | Thr | Gly | Asp | Lys |
| 145 | | | | | 150 | | | | | 155 | | | | | 160 |
| Gln | Ala | Phe | His | Ser | Ala | His | Val | Gln | Pro | Val | Phe | Ala | Val | Leu | Asp |
| | | | | 165 | | | | | 170 | | | | | 175 | |
| Pro | Val | Tyr | Thr | Tyr | Thr | Leu | Pro | Pro | Arg | Gln | Val | Ala | Asn | Gly | Val |
| | | | 180 | | | | | 185 | | | | | 190 | | |
| Val | Asp | Ala | Phe | Val | His | Thr | Val | Glu | Gln | Tyr | Val | Thr | Lys | Pro | Val |
| | | | 195 | | | | | 200 | | | | | 205 | | |
| Asp | Ala | Lys | Ile | Gln | Asp | Arg | Phe | Ala | Glu | Gly | Ile | Leu | Leu | Thr | Leu |
| | 210 | | | | | 215 | | | | | 220 | | | | |
| Ile | Glu | Asp | Gly | Pro | Lys | Ala | Leu | Lys | Glu | Pro | Glu | Asn | Tyr | Asp | Val |
| 225 | | | | | 230 | | | | | 235 | | | | | 240 |
| Arg | Ala | Asn | Val | Met | Trp | Ala | Ala | Thr | Gln | Ala | Leu | Asn | Gly | Leu | Ile |
| | | | | 245 | | | | | 250 | | | | | 255 | |
| Gly | Ala | Gly | Val | Pro | Gln | Asp | Trp | Ala | Thr | His | Met | Leu | Gly | His | Glu |
| | | | 260 | | | | | 265 | | | | | 270 | | |
| Leu | Thr | Ala | Met | His | Gly | Leu | Asp | His | Ala | Gln | Thr | Leu | Ala | Ile | Val |
| | | | 275 | | | | | 280 | | | | | 285 | | |
| Leu | Pro | Ala | Leu | Trp | Asn | Glu | Lys | Arg | Asp | Thr | Lys | Arg | Ala | Lys | Leu |
| | 290 | | | | | 295 | | | | | 300 | | | | |
| Leu | Gln | Tyr | Ala | Glu | Arg | Val | Trp | Asn | Ile | Thr | Glu | Gly | Ser | Asp | Asp |
| 305 | | | | | 310 | | | | | 315 | | | | | 320 |
| Glu | Arg | Ile | Asp | Ala | Ala | Ile | Ala | Ala | Thr | Arg | Asn | Phe | Phe | Glu | Gln |
| | | | | 325 | | | | | 330 | | | | | 335 | |
| Leu | Gly | Val | Pro | Thr | His | Leu | Ser | Asp | Tyr | Gly | Leu | Asp | Gly | Ser | Ser |
| | | | 340 | | | | | 345 | | | | | 350 | | |
| Ile | Pro | Ala | Leu | Leu | Lys | Lys | Leu | Glu | Glu | His | Gly | Met | Thr | Gln | Leu |
| | | | 355 | | | | | 360 | | | | | 365 | | |
| Gly | Glu | Asn | His | Asp | Ile | Thr | Leu | Asp | Val | Ser | Arg | Arg | Ile | Tyr | Glu |
| | 370 | | | | | 375 | | | | | 380 | | | | |

Ala Ala Arg
385

<210> SEQ ID NO 39
<211> LENGTH: 1197
<212> TYPE: DNA
<213> ORGANISM: Saccharomyces cerevisiae

<400> SEQUENCE: 39

```
atgtctcaga acgtttacat tgtatcgact gccagaaccc caattggttc attccagggt      60
tctctatcct ccaagacagc agtggaattg ggtgctgttg ctttaaaagg cgccttggct     120
aaggttccag aattggatgc atccaaggat tttgacgaaa ttattttggg taacgttctt     180
tctgccaatt tgggccaagc tccggccaga caagttgctt ggctgccgg tttgagtaat      240
catatcgttg caagcacagt taacaaggtc tgtgcatccg ctatgaaggc aatcattttg     300
ggtgctcaat ccatcaaatg tggtaatgct gatgttgtcg tagctggtgg ttgtgaatct     360
atgactaacg caccatacta catgccagca gcccgtgcgg gtgccaaatt tggccaaact     420
gttcttgttg atggtgtcga agagatgggt ttgaacgatg cgtacgatgg tctagccatg     480
ggtgtacacg cagaaaagtg tgcccgtgat tgggatatta ctagagaaca acaagacaat     540
tttgccatcg aatcctacca aaaatctcaa aaatctcaaa aggaaggtaa attcgacaat     600
gaaattgtac tgttaccat taagggattt agaggtaagc ctgatactca agtcacgaag      660
gacgaggaac ctgctagatt acacgttgaa aaattgagat ctgcaaggac tgttttccaa     720
aaagaaaacg gtactgttac tgccgctaac gcttctccaa tcaacgatgg tgctgcagcc     780
gtcatcttgg tttccgaaaa agttttgaag gaaaagaatt gaagcctttt ggctattatc     840
aaaggttggg gtgaggccgc tcatcaacca gctgatttta catgggctcc atctcttgca     900
gttccaaagg ctttgaaaca tgctggcatc gaagacatca attctgttga ttactttgaa     960
ttcaatgaag cctttttcggt tgtcggtttg gtgaacacta agattttgaa gctagaccca    1020
tctaaggtta atgtatatgg tggtgctgtt gctctaggtc acccattggg ttgttctggt    1080
gctagagtgg ttgttacact gctatccatc ttacagcaag aaggaggtaa gatcggtgtt    1140
gccgccattt gtaatggtgg tggtggtgct cctctattg tcattgaaaa gatatga      1197
```

<210> SEQ ID NO 40
<211> LENGTH: 398
<212> TYPE: PRT
<213> ORGANISM: Saccharomyces cerevisiae

<400> SEQUENCE: 40

```
Met Ser Gln Asn Val Tyr Ile Val Ser Thr Ala Arg Thr Pro Ile Gly
1               5                   10                  15

Ser Phe Gln Gly Ser Leu Ser Ser Lys Thr Ala Val Glu Leu Gly Ala
            20                  25                  30

Val Ala Leu Lys Gly Ala Leu Ala Lys Val Pro Glu Leu Asp Ala Ser
        35                  40                  45

Lys Asp Phe Asp Glu Ile Ile Phe Gly Asn Val Leu Ser Ala Asn Leu
    50                  55                  60

Gly Gln Ala Pro Ala Arg Gln Val Ala Leu Ala Gly Leu Ser Asn
65                  70                  75                  80

His Ile Val Ala Ser Thr Val Asn Lys Val Cys Ala Ser Ala Met Lys
            85                  90                  95

Ala Ile Ile Leu Gly Ala Gln Ser Ile Lys Cys Gly Asn Ala Asp Val
        100                 105                 110
```

Val Val Ala Gly Gly Cys Glu Ser Met Thr Asn Ala Pro Tyr Tyr Met
            115                 120                 125

Pro Ala Ala Arg Ala Gly Ala Lys Phe Gly Gln Thr Val Leu Val Asp
        130                 135                 140

Gly Val Glu Arg Asp Gly Leu Asn Asp Ala Tyr Asp Gly Leu Ala Met
145                 150                 155                 160

Gly Val His Ala Glu Lys Cys Ala Arg Asp Trp Asp Ile Thr Arg Glu
                165                 170                 175

Gln Gln Asp Asn Phe Ala Ile Glu Ser Tyr Gln Lys Ser Gln Lys Ser
            180                 185                 190

Gln Lys Glu Gly Lys Phe Asp Asn Glu Ile Val Pro Val Thr Ile Lys
        195                 200                 205

Gly Phe Arg Gly Lys Pro Asp Thr Gln Val Thr Lys Asp Glu Glu Pro
    210                 215                 220

Ala Arg Leu His Val Glu Lys Leu Arg Ser Ala Arg Thr Val Phe Gln
225                 230                 235                 240

Lys Glu Asn Gly Thr Val Thr Ala Ala Asn Ala Ser Pro Ile Asn Asp
                245                 250                 255

Gly Ala Ala Ala Val Ile Leu Val Ser Glu Lys Val Leu Lys Glu Lys
            260                 265                 270

Asn Leu Lys Pro Leu Ala Ile Ile Lys Gly Trp Gly Glu Ala Ala His
        275                 280                 285

Gln Pro Ala Asp Phe Thr Trp Ala Pro Ser Leu Ala Val Pro Lys Ala
    290                 295                 300

Leu Lys His Ala Gly Ile Glu Asp Ile Asn Ser Val Asp Tyr Phe Glu
305                 310                 315                 320

Phe Asn Glu Ala Phe Ser Val Val Gly Leu Val Asn Thr Lys Ile Leu
                325                 330                 335

Lys Leu Asp Pro Ser Lys Val Asn Val Tyr Gly Gly Ala Val Ala Leu
            340                 345                 350

Gly His Pro Leu Gly Cys Ser Gly Ala Arg Val Val Thr Leu Leu
        355                 360                 365

Ser Ile Leu Gln Gln Glu Gly Lys Ile Gly Val Ala Ala Ile Cys
    370                 375                 380

Asn Gly Gly Gly Gly Ala Ser Ser Ile Val Ile Glu Lys Ile
385                 390                 395

<210> SEQ ID NO 41
<211> LENGTH: 1713
<212> TYPE: DNA
<213> ORGANISM: Bacillus subtilis

<400> SEQUENCE: 41
ttgacaaaag caacaaaaga acaaaaatcc cttgtgaaaa acagaggggc ggagcttgtt      60
gttgattgct tagtggagca aggtgtcaca catgtatttg cattccagg tgcaaaaatt     120 gatgcggtat ttgacgcttt acaagataaa ggacctgaaa ttatcgttgc ccggcacgaa     180
caaaacgcag cattcatggc ccaagcagtc ggccgtttaa ctggaaaacc gggagtcgtg     240
ttagtcacat caggaccggg tgcctctaac ttggcaacag gcctgctgac agcgaacact     300
gaaggagacc ctgtcgttgc gcttgctgga aacgtgatcc gtgcagatcg tttaaaacgg     360
acacatcaat ctttggataa tgcggcgcta ttccagccga ttacaaaata cagtgtagaa     420
gttcaagatg taaaaatat accggaagct gttacaaatg catttaggat agcgtcagca     480

```
gggcaggctg gggccgcttt tgtgagcttt ccgcaagatg ttgtgaatga agtcacaaat     540
acgaaaaacg tgcgtgctgt tgcagcgcca aaactcggtc ctgcagcaga tgatgcaatc     600
agtgcggcca tagcaaaaat ccaaacagca aaacttcctg tcgttttggt cggcatgaaa     660
ggcgaaagac cggaagcaat taaagcggtt cgcaagcttt tgaaaaaggt tcagcttcca     720
tttgttgaaa catatcaagc tgccggtacc ctttctagag atttagagga tcaatatttt     780
ggccgtatcg gtttgttccg caaccagcct ggcgatttac tgctagagca ggcagatgtt     840
gttctgacga tcggctatga cccgattgaa tatgatccga attctggaa tatcaatgga     900 gaccggacaa ttatccattt agacgagatt atcgctgaca ttgatcatgc ttaccagcct     960
gatcttgaat tgatcggtga cattccgtcc acgatcaatc atatcgaaca cgatgctgtg    1020
aaagtggaat tgcagagcg tgagcagaaa atcctttctg atttaaaaca atatatgcat    1080
gaaggtgagc aggtgcctgc agattggaaa tcagacagag cgcaccctct tgaaatcgtt    1140
aaagagttgc gtaatgcagt cgatgatcat gttacagtaa cttgcgatat cggttcgcac    1200
gccatttgga tgtcacgtta tttccgcagc tacgagccgt taacattaat gatcagtaac    1260
ggtatgcaaa cactcggcgt tgcgcttcct tgggcaatcg gcgcttcatt ggtgaaaccg    1320
ggagaaaaag tggtttctgt ctctggtgac ggcggtttct tattctcagc aatgaattta    1380
gagacagcag ttcgactaaa agcaccaatt gtacacattg tatggaacga cagcacatat    1440
gacatggttg cattccagca attgaaaaaa tataaccgta catctgcggt cgatttcgga    1500
aatatcgata tcgtgaaata tgcggaaagc ttcggagcaa ctggcttgcg cgtagaatca    1560
ccagaccagc tggcagatgt tctgcgtcaa ggcatgaacg ctgaaggtcc tgtcatcatc    1620
gatgtcccgg ttgactacag tgataacatt aatttagcaa gtgacaagct tccgaaagaa    1680
ttcggggaac tcatgaaaac gaaagctctc tag                                 1713
```

<210> SEQ ID NO 42
<211> LENGTH: 570
<212> TYPE: PRT
<213> ORGANISM: Bacillus subtilis

<400> SEQUENCE: 42

```
Met Thr Lys Ala Thr Lys Glu Gln Lys Ser Leu Val Lys Asn Arg Gly
1               5                   10                  15

Ala Glu Leu Val Val Asp Cys Leu Val Glu Gln Gly Val Thr His Val
            20                  25                  30

Phe Gly Ile Pro Gly Ala Lys Ile Asp Ala Val Phe Asp Ala Leu Gln
        35                  40                  45

Asp Lys Gly Pro Glu Ile Ile Val Ala Arg His Glu Gln Asn Ala Ala
    50                  55                  60

Phe Met Ala Gln Ala Val Gly Arg Leu Thr Gly Lys Pro Gly Val Val
65                  70                  75                  80

Leu Val Thr Ser Gly Pro Gly Ala Ser Asn Leu Ala Thr Gly Leu Leu
                85                  90                  95

Thr Ala Asn Thr Glu Gly Asp Pro Val Val Ala Leu Ala Gly Asn Val
            100                 105                 110

Ile Arg Ala Asp Arg Leu Lys Arg Thr His Gln Ser Leu Asp Asn Ala
        115                 120                 125

Ala Leu Phe Gln Pro Ile Thr Lys Tyr Ser Val Glu Val Gln Asp Val
    130                 135                 140

Lys Asn Ile Pro Glu Ala Val Thr Asn Ala Phe Arg Ile Ala Ser Ala
145                 150                 155                 160
```

```
Gly Gln Ala Gly Ala Ala Phe Val Ser Phe Pro Gln Asp Val Val Asn
                165                 170                 175

Glu Val Thr Asn Thr Lys Asn Val Arg Ala Val Ala Ala Pro Lys Leu
            180                 185                 190

Gly Pro Ala Ala Asp Asp Ala Ile Ser Ala Ala Ile Ala Lys Ile Gln
        195                 200                 205

Thr Ala Lys Leu Pro Val Val Leu Val Gly Met Lys Gly Gly Arg Pro
    210                 215                 220

Glu Ala Ile Lys Ala Val Arg Lys Leu Leu Lys Val Gln Leu Pro
225                 230                 235                 240

Phe Val Glu Thr Tyr Gln Ala Ala Gly Thr Leu Ser Arg Asp Leu Glu
                245                 250                 255

Asp Gln Tyr Phe Gly Arg Ile Gly Leu Phe Arg Asn Gln Pro Gly Asp
            260                 265                 270

Leu Leu Leu Glu Gln Ala Asp Val Val Leu Thr Ile Gly Tyr Asp Pro
        275                 280                 285

Ile Glu Tyr Asp Pro Lys Phe Trp Asn Ile Asn Gly Asp Arg Thr Ile
    290                 295                 300

Ile His Leu Asp Glu Ile Ile Ala Asp Ile Asp His Ala Tyr Gln Pro
305                 310                 315                 320

Asp Leu Glu Leu Ile Gly Asp Ile Pro Ser Thr Ile Asn His Ile Glu
                325                 330                 335

His Asp Ala Val Lys Val Glu Phe Ala Glu Arg Glu Gln Lys Ile Leu
            340                 345                 350

Ser Asp Leu Lys Gln Tyr Met His Glu Gly Glu Gln Val Pro Ala Asp
        355                 360                 365

Trp Lys Ser Asp Arg Ala His Pro Leu Glu Ile Val Lys Glu Leu Arg
    370                 375                 380

Asn Ala Val Asp Asp His Val Thr Val Thr Cys Asp Ile Gly Ser His
385                 390                 395                 400

Ala Ile Trp Met Ser Arg Tyr Phe Arg Ser Tyr Glu Pro Leu Thr Leu
                405                 410                 415

Met Ile Ser Asn Gly Met Gln Thr Leu Gly Val Ala Leu Pro Trp Ala
            420                 425                 430

Ile Gly Ala Ser Leu Val Lys Pro Gly Glu Lys Val Val Ser Val Ser
        435                 440                 445

Gly Asp Gly Gly Phe Leu Phe Ser Ala Met Glu Leu Glu Thr Ala Val
    450                 455                 460

Arg Leu Lys Ala Pro Ile Val His Ile Val Trp Asn Asp Ser Thr Tyr
465                 470                 475                 480

Asp Met Val Ala Phe Gln Gln Leu Lys Lys Tyr Asn Arg Thr Ser Ala
                485                 490                 495

Val Asp Phe Gly Asn Ile Asp Ile Val Lys Tyr Ala Glu Ser Phe Gly
            500                 505                 510

Ala Thr Gly Leu Arg Val Glu Ser Pro Asp Gln Leu Ala Asp Val Leu
        515                 520                 525

Arg Gln Gly Met Asn Ala Glu Gly Pro Val Ile Ile Asp Val Pro Val
    530                 535                 540

Asp Tyr Ser Asp Asn Ile Asn Leu Ala Ser Asp Lys Leu Pro Lys Glu
545                 550                 555                 560

Phe Gly Glu Leu Met Lys Thr Lys Ala Leu
                565                 570
```

<210> SEQ ID NO 43
<211> LENGTH: 1188
<212> TYPE: DNA
<213> ORGANISM: Saccharomyces cerevisiae

<400> SEQUENCE: 43

```
atgttgagaa ctcaagccgc cagattgatc tgcaactccc gtgtcatcac tgctaagaga      60
acctttgctt tggccacccg tgctgctgct tacagcagac cagctgcccg tttcgttaag     120
ccaatgatca ctacccgtgg tttgaagcaa atcaacttcg gtggtactgt tgaaaccgtc     180
tacgaaagag ctgactggcc aagagaaaag ttgttggact acttcaagaa cgacactttt     240
gctttgatcg gttacggttc ccaaggttac ggtcaaggtt tgaacttgag agacaacggt     300
ttgaacgtta tcattggtgt ccgtaaagat ggtgcttctt ggaaggctgc catcgaagac     360
ggttgggttc aggcaagaa cttgttcact gttgaagatg ctatcaagag aggtagttac     420
gttatgaact tgttgtccga tgccgctcaa tcagaaacct ggcctgctat caagccattg     480
ttgaccaagg gtaagacttt gtacttctcc acggtttct ccccagtctt caaggacttg     540
actcacgttg aaccaccaaa ggacttagat gttatcttgg ttgctccaaa gggttccggt     600
agaactgtca gatctttgtt caaggaaggt cgtggtatta actcttctta cgccgtctgg     660
aacgatgtca ccggtaaggc tcacgaaaag gcccaagctt tggccgttgc cattggttcc     720
ggttacgttt accaaaccac tttcgaaaga agttcaact ctgacttgta cggtgaaaga     780
ggttgtttaa tgggtggtat ccacggtatg ttcttggctc aatacgacgt cttgagagaa     840
aacggtcact ccccatctga agctttcaac gaaaccgtcg aagaagctac ccaatctcta     900
tacccattga tcggtaagta cggtatggat acatgtacg atgcttgttc caccaccgcc     960
agaagaggtg ctttggactg gtacccaatc ttcaagaatg ctttgaagcc tgttttccaa    1020
gacttgtacg aatctaccaa gaacggtacc gaaaccaaga gatctttgga attcaactct    1080
caacctgact acagagaaaa gctagaaaag gaattagaca ccatcagaaa catggaaatc    1140
tggaaggttg gtaaggaagt cagaaagttg agaccagaaa accaataa                1188
```

<210> SEQ ID NO 44
<211> LENGTH: 395
<212> TYPE: PRT
<213> ORGANISM: Saccharomyces cerevisiae

<400> SEQUENCE: 44

```
Met Leu Arg Thr Gln Ala Ala Arg Leu Ile Cys Asn Ser Arg Val Ile
1               5                   10                  15

Thr Ala Lys Arg Thr Phe Ala Leu Ala Thr Arg Ala Ala Ala Tyr Ser
            20                  25                  30

Arg Pro Ala Ala Arg Phe Val Lys Pro Met Ile Thr Thr Arg Gly Leu
        35                  40                  45

Lys Gln Ile Asn Phe Gly Gly Thr Val Glu Thr Val Tyr Glu Arg Ala
    50                  55                  60

Asp Trp Pro Arg Glu Lys Leu Leu Asp Tyr Phe Lys Asn Asp Thr Phe
65                  70                  75                  80

Ala Leu Ile Gly Tyr Gly Ser Gln Gly Tyr Gly Gln Gly Leu Asn Leu
                85                  90                  95

Arg Asp Asn Gly Leu Asn Val Ile Ile Gly Val Arg Lys Asp Gly Ala
            100                 105                 110

Ser Trp Lys Ala Ala Ile Glu Asp Gly Trp Val Pro Gly Lys Asn Leu
        115                 120                 125
```

```
Phe Thr Val Glu Asp Ala Ile Lys Arg Gly Ser Tyr Val Met Asn Leu
            130                 135                 140

Leu Ser Asp Ala Ala Gln Ser Glu Thr Trp Pro Ala Ile Lys Pro Leu
145                 150                 155                 160

Leu Thr Lys Gly Lys Thr Leu Tyr Phe Ser His Gly Phe Ser Pro Val
                165                 170                 175

Phe Lys Asp Leu Thr His Val Glu Pro Pro Lys Asp Leu Asp Val Ile
            180                 185                 190

Leu Val Ala Pro Lys Gly Ser Gly Arg Thr Val Arg Ser Leu Phe Lys
            195                 200                 205

Glu Gly Arg Gly Ile Asn Ser Ser Tyr Ala Val Trp Asn Asp Val Thr
            210                 215                 220

Gly Lys Ala His Glu Lys Ala Gln Ala Leu Ala Val Ala Ile Gly Ser
225                 230                 235                 240

Gly Tyr Val Tyr Gln Thr Thr Phe Glu Arg Glu Val Asn Ser Asp Leu
                245                 250                 255

Tyr Gly Glu Arg Gly Cys Leu Met Gly Gly Ile His Gly Met Phe Leu
            260                 265                 270

Ala Gln Tyr Asp Val Leu Arg Glu Asn Gly His Ser Pro Ser Glu Ala
            275                 280                 285

Phe Asn Glu Thr Val Glu Glu Ala Thr Gln Ser Leu Tyr Pro Leu Ile
            290                 295                 300

Gly Lys Tyr Gly Met Asp Tyr Met Tyr Asp Ala Cys Ser Thr Thr Ala
305                 310                 315                 320

Arg Arg Gly Ala Leu Asp Trp Tyr Pro Ile Phe Lys Asn Ala Leu Lys
                325                 330                 335

Pro Val Phe Gln Asp Leu Tyr Glu Ser Thr Lys Asn Gly Thr Glu Thr
            340                 345                 350

Lys Arg Ser Leu Glu Phe Asn Ser Gln Pro Asp Tyr Arg Glu Lys Leu
            355                 360                 365

Glu Lys Glu Leu Asp Thr Ile Arg Asn Met Glu Ile Trp Lys Val Gly
            370                 375                 380

Lys Glu Val Arg Lys Leu Arg Pro Glu Asn Gln
385                 390                 395

<210> SEQ ID NO 45
<211> LENGTH: 1029
<212> TYPE: DNA
<213> ORGANISM: Bacillus subtilis

<400> SEQUENCE: 45
atggtaaaag tatattataa cggtgatatc aaagagaacg tattggctgg aaaaacagta      60
gcggttatcg ggtacggttc gcaaggccac gcacatgccc tgaaccttaa agaaagcgga     120
gtagacgtga tcgtcggtgt tagacaagga aaatctttca ctcaagccca agaagacgga     180
cataaagtat tttcagtaaa agaagcggca gcccaagccg aaatcatcat ggttctgctt     240
ccggatgagc agcagcaaaa agtatacgaa gctgaaatca agatgaatt gacagcagga     300 aaatcattag tattcgctca tggatttaac gtgcatttcc atcaaattgt tcctccggcg     360
gatgtagatg tattcttagt ggcccctaaa ggcccgggac acttggtaag aagaacatat     420
gagcaaggag ctggcgtacc tgcattgttc gcaatctatc aagatgtgac tggagaagca     480
agagacaaag ccctcgctta tgctaaagga tcggcggcg caagagcggg cgtattagaa     540
acgacattta agaagaaac agaaacagat ttgttcggtg agcaagcagt tctttgcggc     600
```

-continued

```
ggattaagcg cgcttgtcaa agccggattt gaaaccttaa ctgaagcagg ttatcagcct    660
gaacttgcat acttcgagtg tcttcatgag ctgaaattaa tcgtagacct tatgtacgaa    720
gaaggacttg caggaatgag atattcaatc tctgacacag cacagtgggg agatttcgta    780
tcaggccctc gcgttgtgga cgccaaagta aagaatcta tgaaagaagt attaaaagat     840
atccaaaacg gtacattcgc aaaagagtgg atcgtcgaaa accaagtaaa ccgtcctcgt    900
ttcaacgcta tcaatgcaag cgagaacgaa catcaaatcg aagtagtggg aagaaagctt    960
cgtgaaatga tgccgtttgt gaaacaaggc aagaagaagg aagcggtggt ctccgttgcg   1020
caaaattaa                                                            1029
```

<210> SEQ ID NO 46
<211> LENGTH: 342
<212> TYPE: PRT
<213> ORGANISM: Bacillus subtilis

<400> SEQUENCE: 46

```
Met Val Lys Val Tyr Tyr Asn Gly Asp Ile Lys Glu Asn Val Leu Ala
1               5                   10                  15

Gly Lys Thr Val Ala Val Ile Gly Tyr Gly Ser Gln Gly His Ala His
            20                  25                  30

Ala Leu Asn Leu Lys Glu Ser Gly Val Asp Val Ile Gly Val Arg
        35                  40                  45

Gln Gly Lys Ser Phe Thr Gln Ala Gln Glu Asp Gly His Lys Val Phe
    50                  55                  60

Ser Val Lys Glu Ala Ala Gln Ala Glu Ile Ile Met Val Leu Leu
65                  70                  75                  80

Pro Asp Glu Gln Gln Gln Lys Val Tyr Glu Ala Glu Ile Lys Asp Glu
                85                  90                  95

Leu Thr Ala Gly Lys Ser Leu Val Phe Ala His Gly Phe Asn Val His
            100                 105                 110

Phe His Gln Ile Val Pro Pro Ala Asp Val Asp Val Phe Leu Val Ala
        115                 120                 125

Pro Lys Gly Pro Gly His Leu Val Arg Arg Thr Tyr Glu Gln Gly Ala
    130                 135                 140

Gly Val Pro Ala Leu Phe Ala Ile Tyr Gln Asp Val Thr Gly Glu Ala
145                 150                 155                 160

Arg Asp Lys Ala Leu Ala Tyr Ala Lys Gly Ile Gly Gly Ala Arg Ala
                165                 170                 175

Gly Val Leu Glu Thr Thr Phe Lys Glu Glu Thr Glu Thr Asp Leu Phe
            180                 185                 190

Gly Glu Gln Ala Val Leu Cys Gly Gly Leu Ser Ala Leu Val Lys Ala
        195                 200                 205

Gly Phe Glu Thr Leu Thr Glu Ala Gly Tyr Gln Pro Glu Leu Ala Tyr
    210                 215                 220

Phe Glu Cys Leu His Glu Leu Lys Leu Ile Val Asp Leu Met Tyr Glu
225                 230                 235                 240

Glu Gly Leu Ala Gly Met Arg Tyr Ser Ile Ser Asp Thr Ala Gln Trp
                245                 250                 255

Gly Asp Phe Val Ser Gly Pro Arg Val Val Asp Ala Lys Val Lys Glu
            260                 265                 270

Ser Met Lys Glu Val Leu Lys Asp Ile Gln Asn Gly Thr Phe Ala Lys
        275                 280                 285
```

```
Glu Trp Ile Val Glu Asn Gln Val Asn Arg Pro Arg Phe Asn Ala Ile
    290             295                 300
Asn Ala Ser Glu Asn Glu His Gln Ile Glu Val Val Gly Arg Lys Leu
305             310                 315                 320
Arg Glu Met Met Pro Phe Val Lys Gln Gly Lys Lys Lys Glu Ala Val
            325                 330                 335
Val Ser Val Ala Gln Asn
            340
```

<210> SEQ ID NO 47
<211> LENGTH: 1758
<212> TYPE: DNA
<213> ORGANISM: Saccharomyces cerevisiae

<400> SEQUENCE: 47

| | |
|---|---|
| atgggcttgt taacgaaagt tgctacatct agacaattct ctacaacgag atgcgttgca | 60 |
| aagaagctca acaagtactc gtatatcatc actgaaccta agggccaagg tgcgtcccag | 120 |
| gccatgcttt atgccaccgg tttcaagaag gaagatttca agaagcctca agtcggggtt | 180 |
| ggttcctgtt ggtggtccgg taacccatgt aacatgcatc tattggactt gaataacaga | 240 |
| tgttctcaat ccattgaaaa agcgggtttg aaagctatgc agttcaacac catcggtgtt | 300 |
| tcagacggta tctctatggg tactaaaggt atgagatact cgttacaaag tagagaaatc | 360 |
| attgcagact cctttgaaac catcatgatg gcacaacact acgatgctaa catcgccatc | 420 |
| ccatcatgtg acaaaaacat gcccggtgtc atgatggcca tgggtagaca aacagacct | 480 |
| tccatcatgg tatatggtgg tactatcttg cccggtcatc aacatgtgg ttcttcgaag | 540 |
| atctctaaaa acatcgatat cgtctctgcg ttccaatcct acggtgaata tatttccaag | 600 |
| caattcactg aagaagaaag agaagatgtt gtggaacatg catgcccagg tcctggttct | 660 |
| tgtggtggta tgtatactgc aacacaatg gcttctgccg ctgaagtgct aggtttgacc | 720 |
| attccaaact cctcttcctt cccagccgtt tccaaggaga agttagctga gtgtgacaac | 780 |
| attggtgaat acatcaagaa gacaatggaa ttgggtattt acctcgtga tatcctcaca | 840 |
| aaagaggctt ttgaaaacgc cattacttat gtcgttgcaa ccggtgggtc cactaatgct | 900 |
| gttttgcatt tggtggctgt tgctcactct gcgggtgtca agttgtcacc agatgatttc | 960 |
| caaagaatca gtgatactac accattgatc ggtgacttca aaccttctgg taaatacgtc | 1020 |
| atggccgatt tgattaacgt tggtggtacc caatctgtga ttaagtatct atatgaaaac | 1080 |
| aacatgttgc acggtaacac aatgactgtt accggtgaca ctttggcaga acgtgcaaag | 1140 |
| aaagcaccaa gcctacctga aggacaagag attattaagc cactctccca cccaatcaag | 1200 |
| gccaacggtc acttgcaaat tctgtacggt tcattggcac aggtggagc tgtgggtaaa | 1260 |
| attaccggta aggaaggtac ttacttcaag ggtagagcac gtgtgttcga agaggaaggt | 1320 |
| gcctttattg aagccttgga agaggtgaa atcaagaagg gtgaaaaaac cgttgttgtt | 1380 |
| atcagatatg aaggtccaag aggtgcacca ggtatgcctg aaatgctaaa gccttcctct | 1440 |
| gctctgatgg gttacggttt gggtaaagat gttgcattgt tgactgatgg tagattctct | 1500 |
| ggtggttctc acgggttctt aatcggccac attgttcccg aagccgctga aggtggtcct | 1560 |
| atcgggttgg tcagagacgg cgatgagatt atcattgatg ctgataataa caagattgac | 1620 |
| ctattagtct ctgataagga aatggctcaa cgtaaacaaa gttgggttgc acctccacct | 1680 |
| cgttacacaa gaggtactct atccaagtat gctaagttgg tttccaacgc ttccaacggt | 1740 |
| tgtgttttag atgcttga | 1758 |

<210> SEQ ID NO 48
<211> LENGTH: 585
<212> TYPE: PRT
<213> ORGANISM: Saccharomyces cerevisiae

<400> SEQUENCE: 48

Met Gly Leu Leu Thr Lys Val Ala Thr Ser Arg Gln Phe Ser Thr Thr
1               5                   10                  15

Arg Cys Val Ala Lys Lys Leu Asn Lys Tyr Ser Tyr Ile Ile Thr Glu
            20                  25                  30

Pro Lys Gly Gln Gly Ala Ser Gln Ala Met Leu Tyr Ala Thr Gly Phe
        35                  40                  45

Lys Lys Glu Asp Phe Lys Lys Pro Gln Val Gly Val Gly Ser Cys Trp
    50                  55                  60

Trp Ser Gly Asn Pro Cys Asn Met His Leu Leu Asp Leu Asn Asn Arg
65                  70                  75                  80

Cys Ser Gln Ser Ile Glu Lys Ala Gly Leu Lys Ala Met Gln Phe Asn
                85                  90                  95

Thr Ile Gly Val Ser Asp Gly Ile Ser Met Gly Thr Lys Gly Met Arg
            100                 105                 110

Tyr Ser Leu Gln Ser Arg Glu Ile Ile Ala Asp Ser Phe Glu Thr Ile
        115                 120                 125

Met Met Ala Gln His Tyr Asp Ala Asn Ile Ala Ile Pro Ser Cys Asp
    130                 135                 140

Lys Asn Met Pro Gly Val Met Met Ala Met Gly Arg His Asn Arg Pro
145                 150                 155                 160

Ser Ile Met Val Tyr Gly Gly Thr Ile Leu Pro Gly His Pro Thr Cys
                165                 170                 175

Gly Ser Ser Lys Ile Ser Lys Asn Ile Asp Ile Val Ser Ala Phe Gln
            180                 185                 190

Ser Tyr Gly Glu Tyr Ile Ser Lys Gln Phe Thr Glu Glu Arg Glu
        195                 200                 205

Asp Val Val Glu His Ala Cys Pro Gly Pro Gly Ser Cys Gly Gly Met
    210                 215                 220

Tyr Thr Ala Asn Thr Met Ala Ser Ala Ala Glu Val Leu Gly Leu Thr
225                 230                 235                 240

Ile Pro Asn Ser Ser Phe Pro Ala Val Ser Lys Glu Lys Leu Ala
                245                 250                 255

Glu Cys Asp Asn Ile Gly Glu Tyr Ile Lys Lys Thr Met Glu Leu Gly
            260                 265                 270

Ile Leu Pro Arg Asp Ile Leu Thr Lys Glu Ala Phe Glu Asn Ala Ile
        275                 280                 285

Thr Tyr Val Val Ala Thr Gly Gly Ser Thr Asn Ala Val Leu His Leu
    290                 295                 300

Val Ala Val Ala His Ser Ala Gly Val Lys Leu Ser Pro Asp Asp Phe
305                 310                 315                 320

Gln Arg Ile Ser Asp Thr Thr Pro Leu Ile Gly Asp Phe Lys Pro Ser
                325                 330                 335

Gly Lys Tyr Val Met Ala Asp Leu Ile Asn Val Gly Gly Thr Gln Ser
            340                 345                 350

Val Ile Lys Tyr Leu Tyr Glu Asn Asn Met Leu His Gly Asn Thr Met
        355                 360                 365

Thr Val Thr Gly Asp Thr Leu Ala Glu Arg Ala Lys Lys Ala Pro Ser

```
                 370               375               380
Leu Pro Glu Gly Gln Glu Ile Ile Lys Pro Leu Ser His Pro Ile Lys
385                 390               395               400

Ala Asn Gly His Leu Gln Ile Leu Tyr Gly Ser Leu Ala Pro Gly Gly
                405               410               415

Ala Val Gly Lys Ile Thr Gly Lys Glu Gly Thr Tyr Phe Lys Gly Arg
                420               425               430

Ala Arg Val Phe Glu Glu Glu Gly Ala Phe Ile Glu Ala Leu Glu Arg
                435               440               445

Gly Glu Ile Lys Lys Gly Glu Lys Thr Val Val Ile Arg Tyr Glu
450                 455               460

Gly Pro Arg Gly Ala Pro Gly Met Pro Glu Met Leu Lys Pro Ser Ser
465                 470               475               480

Ala Leu Met Gly Tyr Gly Leu Gly Lys Asp Val Ala Leu Leu Thr Asp
                485               490               495

Gly Arg Phe Ser Gly Ser His Gly Phe Leu Ile Gly His Ile Val
                500               505               510

Pro Glu Ala Ala Glu Gly Gly Pro Ile Gly Leu Val Arg Asp Gly Asp
                515               520               525

Glu Ile Ile Ile Asp Ala Asp Asn Asn Lys Ile Asp Leu Leu Val Ser
530                 535               540

Asp Lys Glu Met Ala Gln Arg Lys Gln Ser Trp Val Ala Pro Pro
545                 550               555               560

Arg Tyr Thr Arg Gly Thr Leu Ser Lys Tyr Ala Lys Leu Val Ser Asn
                565               570               575

Ala Ser Asn Gly Cys Val Leu Asp Ala
                580               585

<210> SEQ ID NO 49
<211> LENGTH: 840
<212> TYPE: DNA
<213> ORGANISM: Saccharomyces cereivsiae

<400> SEQUENCE: 49
atggctgata agatagagag gcatactttc aaggtcttca atcaagattt cagtgtagat      60
aagaggtttc aacttatcaa agaaataggg catggagcat acggcatagt gtgttcagcg     120
cggtttgcag aagctgccga agataccaca gttgccatca agaaagtgac aaacgttttt     180
tcgaagacct tactatgtaa aagatcccta cgtgagctaa agcttttgag acatttcaga     240
ggccacaaaa atattacatg tctttatgat atggatattg ttttttatcc agacgggtct     300
atcaatggac tatatcttta tgaggaactt atggaatgtg atatgcacca aatcatcaaa     360
tccggtcaac ctttgacgga tgctcactat caaagtttca cataccaaat attatgtggt     420
ttaaagtata ttcattctgc agatgtcttg catcgtgatt tgaagcccgg caatttgctt     480
gtcaatgcag attgtcaatt gaaaatctgt gattttgggt tagctagagg ttattcggag     540
aatcctgtcg aaaacagtca attttttgacg gagtacgtgg ccactagatg gtatagagct     600
ccggaaataa tgttgagtta ccaaggatat accaaggcga ttgacgtatg gtcagctggc     660 tgtatttag cggagttttct tggtggaaag ccaatcttca aggaaagga ttacgttaat     720 caattgaatc aaatattaca agttttaggg acaccccag acgaaacttt aagaaggatt     780
ggttctaaaa atgttcagga ctacatacat caattaggtt tcattccaaa agtaccttt      840

<210> SEQ ID NO 50
```

<211> LENGTH: 484
<212> TYPE: PRT
<213> ORGANISM: Saccharomyces cerevisiae

<400> SEQUENCE: 50

```
Met Ala Asp Lys Ile Glu Arg His Thr Phe Lys Val Phe Asn Gln Asp
1               5                   10                  15

Phe Ser Val Asp Lys Arg Phe Gln Leu Ile Lys Glu Ile Gly His Gly
                20                  25                  30

Ala Tyr Gly Ile Val Cys Ser Ala Arg Phe Ala Glu Ala Ala Glu Asp
            35                  40                  45

Thr Thr Val Ala Ile Lys Lys Val Thr Asn Val Phe Ser Lys Thr Leu
50                  55                  60

Leu Cys Lys Arg Ser Leu Arg Glu Leu Lys Leu Leu Arg His Phe Arg
65                  70                  75                  80

Gly His Lys Asn Ile Thr Cys Leu Tyr Asp Met Asp Ile Val Phe Tyr
                85                  90                  95

Pro Asp Gly Ser Ile Asn Gly Leu Tyr Leu Tyr Glu Glu Leu Met Glu
            100                 105                 110

Cys Asp Met His Gln Ile Ile Lys Ser Gly Gln Pro Leu Thr Asp Ala
        115                 120                 125

His Tyr Gln Ser Phe Thr Tyr Gln Ile Leu Cys Gly Leu Lys Tyr Ile
130                 135                 140

His Ser Ala Asp Val Leu His Arg Asp Leu Lys Pro Gly Asn Leu Leu
145                 150                 155                 160

Val Asn Ala Asp Cys Gln Leu Lys Ile Cys Asp Phe Gly Leu Ala Arg
                165                 170                 175

Gly Tyr Ser Glu Asn Pro Val Glu Asn Ser Gln Phe Leu Thr Glu Tyr
            180                 185                 190

Val Ala Thr Arg Trp Tyr Arg Ala Pro Glu Ile Met Leu Ser Tyr Gln
        195                 200                 205

Gly Tyr Thr Lys Ala Ile Asp Val Trp Ser Ala Gly Cys Ile Leu Ala
210                 215                 220

Glu Phe Leu Gly Gly Lys Pro Ile Phe Lys Gly Lys Asp Tyr Val Asn
225                 230                 235                 240

Gln Leu Asn Gln Ile Leu Gln Val Leu Gly Thr Pro Pro Asp Glu Thr
                245                 250                 255

Leu Arg Arg Ile Gly Ser Lys Asn Val Gln Asp Tyr Ile His Gln Leu
            260                 265                 270

Gly Phe Ile Pro Lys Val Pro Phe Val Asn Leu Tyr Pro Asn Ala Asn
        275                 280                 285

Ser Gln Ala Leu Asp Leu Leu Glu Gln Met Leu Ala Phe Asp Pro Gln
290                 295                 300

Lys Arg Ile Thr Val Asp Glu Ala Leu Glu His Pro Tyr Leu Ser Ile
305                 310                 315                 320

Trp His Asp Pro Ala Asp Glu Pro Val Cys Ser Glu Lys Phe Glu Phe
                325                 330                 335

Ser Phe Glu Ser Val Asn Asp Met Glu Asp Leu Lys Gln Met Val Ile
            340                 345                 350

Gln Glu Val Gln Asp Phe Arg Leu Phe Val Arg Gln Pro Leu Leu Glu
        355                 360                 365

Glu Gln Arg Gln Leu Gln Leu Gln Gln Gln Gln Gln Gln Gln Gln Gln
370                 375                 380

Gln Gln Gln Gln Gln Gln Gln Pro Ser Asp Val Asp Asn Gly Asn Ala
```

```
                385                 390                 395                 400
Ala Ala Ser Glu Glu Asn Tyr Pro Lys Gln Met Ala Thr Ser Asn Ser
                405                 410                 415

Val Ala Pro Gln Gln Glu Ser Phe Gly Ile His Ser Gln Asn Leu Pro
                420                 425                 430

Arg His Asp Ala Asp Phe Pro Pro Arg Pro Gln Glu Ser Met Met Glu
                435                 440                 445

Met Arg Pro Ala Thr Gly Asn Thr Ala Asp Ile Pro Pro Gln Asn Asp
            450                 455                 460

Asn Gly Thr Leu Leu Asp Leu Glu Lys Glu Leu Glu Phe Gly Leu Asp
465                 470                 475                 480

Arg Lys Tyr Phe

<210> SEQ ID NO 51
<211> LENGTH: 1467
<212> TYPE: DNA
<213> ORGANISM: Candida glabrata

<400> SEQUENCE: 51
atggacgttg agagacagac atttaaggtc tttaaccagg acttcaccat tgataagagg      60
ttcgaattga tcaaagagat tggccatggc gcatatggta tagtgtgttc tgccaggttc     120
acagaggcaa gcgaggagac tacagttgct atcaagaaag tgaccaacat cttcagcaaa     180
acacttctgt gtaaaagatc gctcagagag ttgaagcttc tgagacattt tagaggacat     240
aagaacatta cctgtcttta cgatatggat atcgtattct acccagatgg gtctataaat     300
ggccttcatt tatacgaaga actgatggaa tgtgatatgc accagattat aaaatctggg     360
caagcactaa cagatgcgca ttaccagagt ttcacatatc agatcttgtg tggtttaaaa     420
tatatccact cagctgacgt tctacatcgt gacttaaaac caggtaattt gctggtgaat     480
gccgattgcc aacttaaaat ttgtgatttc gggcttgcaa gaggttatag tgagaatccc     540
gaagagaaca accaattttt aactgagtat gtggcgacca ggtggtatag agcacctgaa     600
atcatgctaa gttaccaagg ttacacaaag gccattgaca tctggtcaac aggttgtatt     660
ttagcagagt ttttaggtgg caaaccgtta ttcaaggggga aggactacgt tgatcaactg     720
aatagaattt tacaggtctt aggtacacca cctgatgaaa ctttaaggag agtgggctca     780
aagaatgtcc aagattatat tcaccaactt ggatacatac aaaagatacc attttctgaa     840
ttattcccta tgcgaatgaa agatgcttta gatctcctgg agggaatgct ggcgtttgat     900
ccacaaaaga gaataactgt ggataaggca ctagagcatc catatctaac catatggcac     960
gacccagctg atgaacctga gtgtaacgaa aagtttgaat tcagtttcga aagcgtgaac    1020
gaaatggaag atttaaagcg catggttgtt gatgaggtac aaagtttcag ggaatttgta    1080
aggcaacctt taatggatga caaatctcaa gaagacgaac aacaacaagg atctcccgag    1140
aattaccaac agacaagccc aacgaatata tccccacaac gtttacataa taatgggtct    1200
catgatctgt tacaggaacc agaatttttg acacagacac caaatcagaa ctcaactatt    1260
ccggatcaac tacaggaatc attcgttgga atccactcag ataatttacc tgagcatgat    1320
acagatttcc caccgagacc tcaagagaac attctggcat cacctatggg actcccatcc    1380
gcatctgatc gaaactccat gaacaacgat tccttcctcg atttagaacg cgagttggag    1440
tttggactgg ataggagata tttatga                                        1467

<210> SEQ ID NO 52
```

```
<211> LENGTH: 488
<212> TYPE: PRT
<213> ORGANISM: Candida glabrata

<400> SEQUENCE: 52

Met Asp Val Glu Arg Gln Thr Phe Lys Val Phe Asn Gln Asp Phe Thr
1               5                   10                  15

Ile Asp Lys Arg Phe Glu Leu Ile Lys Glu Ile Gly His Gly Ala Tyr
            20                  25                  30

Gly Ile Val Cys Ser Ala Arg Phe Thr Glu Ala Ser Glu Thr Thr
        35                  40                  45

Val Ala Ile Lys Lys Val Thr Asn Ile Phe Ser Lys Thr Leu Leu Cys
    50                  55                  60

Lys Arg Ser Leu Arg Glu Leu Lys Leu Leu Arg His Phe Arg Gly His
65                  70                  75                  80

Lys Asn Ile Thr Cys Leu Tyr Asp Met Asp Ile Val Phe Tyr Pro Asp
                85                  90                  95

Gly Ser Ile Asn Gly Leu Tyr Leu Tyr Glu Glu Leu Met Glu Cys Asp
            100                 105                 110

Met His Gln Ile Ile Lys Ser Gly Gln Ala Leu Thr Asp Ala His Tyr
        115                 120                 125

Gln Ser Phe Thr Tyr Gln Ile Leu Cys Gly Leu Lys Tyr Ile His Ser
    130                 135                 140

Ala Asp Val Leu His Arg Asp Leu Lys Pro Gly Asn Leu Leu Val Asn
145                 150                 155                 160

Ala Asp Cys Gln Leu Lys Ile Cys Asp Phe Gly Leu Ala Arg Gly Tyr
                165                 170                 175

Ser Glu Asn Pro Glu Glu Asn Gln Phe Leu Thr Glu Tyr Val Ala
            180                 185                 190

Thr Arg Trp Tyr Arg Ala Pro Glu Ile Met Leu Ser Tyr Gln Gly Tyr
        195                 200                 205

Thr Lys Ala Ile Asp Ile Trp Ser Thr Gly Cys Ile Leu Ala Glu Phe
    210                 215                 220

Leu Gly Gly Lys Pro Leu Phe Lys Gly Lys Asp Tyr Val Asp Gln Leu
225                 230                 235                 240

Asn Arg Ile Leu Gln Val Leu Gly Thr Pro Pro Asp Glu Thr Leu Arg
                245                 250                 255

Arg Val Gly Ser Lys Asn Val Gln Asp Tyr Ile His Gln Leu Gly Tyr
            260                 265                 270

Ile Gln Lys Ile Pro Phe Ser Glu Leu Phe Pro Asn Ala Asn Glu Asp
        275                 280                 285

Ala Leu Asp Leu Leu Glu Gly Met Leu Ala Phe Asp Pro Gln Lys Arg
    290                 295                 300

Ile Thr Val Asp Lys Ala Leu Glu His Pro Tyr Leu Thr Ile Trp His
305                 310                 315                 320

Asp Pro Ala Asp Glu Pro Glu Cys Asn Glu Lys Phe Glu Phe Ser Phe
                325                 330                 335

Glu Ser Val Asn Glu Met Glu Asp Leu Lys Arg Met Val Val Asp Glu
            340                 345                 350

Val Gln Ser Phe Arg Glu Phe Val Arg Gln Pro Leu Met Asp Asp Lys
        355                 360                 365

Ser Gln Glu Asp Glu Gln Gln Gly Ser Pro Glu Asn Tyr Gln Gln
    370                 375                 380

Thr Ser Pro Thr Asn Ile Ser Pro Gln Arg Leu His Asn Asn Gly Ser
```

```
                385               390               395               400
His Asp Leu Leu Gln Glu Pro Glu Phe Leu Thr Gln Thr Pro Asn Gln
                405               410               415

Asn Ser Thr Ile Pro Asp Gln Leu Gln Glu Ser Phe Val Gly Ile His
                420               425               430

Ser Asp Asn Leu Pro Glu His Asp Thr Asp Phe Pro Pro Arg Pro Gln
                435               440               445

Glu Asn Ile Leu Ala Ser Pro Met Gly Leu Pro Ser Ala Ser Asp Arg
    450               455               460

Asn Ser Met Asn Asn Asp Ser Phe Leu Asp Leu Glu Arg Glu Leu Glu
465               470               475               480

Phe Gly Leu Asp Arg Arg Tyr Leu
                485

<210> SEQ ID NO 53
<211> LENGTH: 1530
<212> TYPE: DNA
<213> ORGANISM: Candida albicans

<400> SEQUENCE: 53
atggatcaac aagaagcacc catatattat ggcagatccg taaataaggt ctacaaccag      60
gaatttatca ttgatagtcg attcaaaata gtcaaggagt tgggccatgg tgcctatggt     120
attgtgtgtt cagcaaaata cgataatggg tccaaaaagg ttcctgattc aaacaacggt     180
aatgcctcat cttcagctaa tgcatcgttt gtggcaatca aaagatcac taatattttc      240 agcaaaaaca tcttatgtaa acgtgctttg cgtgaattga agttgttgca gttcttcagg     300
ggccataaaa atataacatg tttatatgat ttggacatta tccccaatcc catgacaggc     360
gagtttaatg aaatatattt atacgaagaa ttaatggaat gtgacatgca ccaaatcatt     420
agatctggac aaccattgtc cgatcagcac taccagtcgt ttatttatca ggtattgtgt     480
ggattgaact tcatccattc ggctgatgtg ttgcatcgtg atttgaaacc aggtaactta     540
cttgtcaatg ccgactgtga gcttaaaatt tgtgactttg gtttagcaag agggttttct     600
gagaaccccg acgaaaatgc tgggtttatg acagagtatg ttgccaccag atggtacagg     660
gcaccagaaa ttatgttgag tttcaccaac tacactaagg caatcgacat ctggtctgtt     720
ggttgtatat tggcagaact tttgggggc aagccactttt ccgtggcaa agattacgta     780 gatcaactta tcagatttt aatgatatta ggtaccccac cagaatccac gttacaaaga      840
atagggtccc acagagccca gaactatgtc agatctttgc cgattacgag aaaagctagc     900
tacgaagaac ttttccctga cgccaacccg ttggcgttgg atttattgga agaatgttg      960 actttagacc cacgtgagag aattacagtt cgagatgcat tgaatcataa gtacttagag    1020
ctttggcatg atcctaaaga agaaattgag tgccaagtca aatttgattt caagtcgttt    1080
gagactgtag atgggttgga cgaaatgaaa cagttgatca tggatgaagt tcagaagttt    1140
cgtgaatttg tgaggaagcc aattgaggaa cagcagcgaa tacaaatgca gctacatatg    1200
caaaaacgtg aagaacagcg acaagaggag gaagagaaag agctactaga acagcaaaga    1260
cagtttccag ctcaagagag tatggatatt tctcagaccc cttacaataa cttggaaacg    1320
aatataggta ctcctcaggt tgaagatgat tatcccagac acaagagtt ggatgagttt     1380 actttttcaa atttggaatc ttcaagctcc atgaatttgt tccaagacat ggctaaacca    1440
tcaggagaag agtatataaa gctagaggaa gagcttgggt ttggattaga tggtgctatg    1500
tttaacaact actgtaacga ccaccagtag                                     1530
```

```
<210> SEQ ID NO 54
<211> LENGTH: 509
<212> TYPE: PRT
<213> ORGANISM: Candida albicans

<400> SEQUENCE: 54

Met Asp Gln Gln Glu Ala Pro Ile Tyr Tyr Gly Arg Ser Val Asn Lys
1               5                   10                  15

Val Tyr Asn Gln Glu Phe Ile Ile Asp Ser Arg Phe Lys Ile Val Lys
            20                  25                  30

Glu Leu Gly His Gly Ala Tyr Gly Ile Val Cys Ser Ala Lys Tyr Asp
        35                  40                  45

Asn Gly Ser Lys Lys Val Pro Asp Ser Asn Asn Gly Asn Ala Ser Ser
    50                  55                  60

Ser Ala Asn Ala Ser Phe Val Ala Ile Lys Lys Ile Thr Asn Ile Phe
65                  70                  75                  80

Ser Lys Asn Ile Leu Cys Lys Arg Ala Leu Arg Glu Leu Lys Leu Leu
                85                  90                  95

Gln Phe Phe Arg Gly His Lys Asn Ile Thr Cys Leu Tyr Asp Leu Asp
            100                 105                 110

Ile Ile Pro Asn Pro Met Thr Gly Glu Phe Asn Glu Ile Tyr Leu Tyr
        115                 120                 125

Glu Glu Leu Met Glu Cys Asp Met His Gln Ile Ile Arg Ser Gly Gln
    130                 135                 140

Pro Leu Ser Asp Gln His Tyr Gln Ser Phe Ile Tyr Gln Val Leu Cys
145                 150                 155                 160

Gly Leu Asn Phe Ile His Ser Ala Asp Val Leu His Arg Asp Leu Lys
                165                 170                 175

Pro Gly Asn Leu Leu Val Asn Ala Asp Cys Glu Leu Lys Ile Cys Asp
            180                 185                 190

Phe Gly Leu Ala Arg Gly Phe Ser Glu Asn Pro Asp Glu Asn Ala Gly
        195                 200                 205

Phe Met Thr Glu Tyr Val Ala Thr Arg Trp Tyr Arg Ala Pro Glu Ile
    210                 215                 220

Met Leu Ser Phe Thr Asn Tyr Thr Lys Ala Ile Asp Ile Trp Ser Val
225                 230                 235                 240

Gly Cys Ile Leu Ala Glu Leu Leu Gly Gly Lys Pro Leu Phe Arg Gly
                245                 250                 255

Lys Asp Tyr Val Asp Gln Leu Asn Gln Ile Leu Met Ile Leu Gly Thr
            260                 265                 270

Pro Pro Glu Ser Thr Leu Gln Arg Ile Gly Ser His Arg Ala Gln Asn
        275                 280                 285

Tyr Val Arg Ser Leu Pro Ile Thr Arg Lys Ala Ser Tyr Glu Glu Leu
    290                 295                 300

Phe Pro Asp Ala Asn Pro Leu Ala Leu Asp Leu Glu Arg Met Leu
305                 310                 315                 320

Thr Leu Asp Pro Arg Glu Arg Ile Thr Val Arg Asp Ala Leu Asn His
                325                 330                 335

Lys Tyr Leu Glu Leu Trp His Asp Pro Lys Glu Ile Glu Cys Gln
            340                 345                 350

Val Lys Phe Asp Phe Lys Ser Phe Glu Thr Val Asp Gly Leu Asp Glu
        355                 360                 365

Met Lys Gln Leu Ile Met Asp Glu Val Gln Lys Phe Arg Glu Phe Val
```

```
                370             375             380
Arg Lys Pro Ile Glu Glu Gln Gln Arg Ile Gln Met Gln Leu His Met
385             390             395             400

Gln Lys Arg Glu Glu Arg Gln Glu Glu Glu Lys Glu Leu Leu
            405             410             415

Glu Gln Gln Arg Gln Phe Pro Ala Gln Glu Ser Met Asp Ile Ser Gln
            420             425             430

Thr Pro Tyr Asn Asn Leu Glu Thr Asn Ile Gly Thr Pro Gln Val Glu
            435             440             445

Asp Asp Tyr Pro Arg Pro Gln Glu Leu Asp Glu Phe Thr Phe Ser Asn
450             455             460

Leu Glu Ser Ser Ser Ser Met Asn Leu Phe Gln Asp Met Ala Lys Pro
465             470             475             480

Ser Gly Glu Glu Tyr Ile Lys Leu Glu Glu Glu Leu Gly Phe Gly Leu
            485             490             495

Asp Gly Ala Met Phe Asn Asn Tyr Cys Asn Asp His Gln
            500             505

<210> SEQ ID NO 55
<211> LENGTH: 1518
<212> TYPE: DNA
<213> ORGANISM: Yarrowia lipolytica

<400> SEQUENCE: 55
atgatacgag cggaccgaca cacgtacaag gtgttcaacc aggaattcac catagacaag     60
cggttccagg tgaccaaaga gctgggccat ggcgcgtacg gcattgtgtg tgcagccaag    120
tacactggga cgcctgatgg gcctggagtt gctatcaaga aggtgaccaa cattttctcg    180
aaaaacattc tgtgtaagcg ggcgttgcgg gagctcaagc tactgaacca cttccgggg    240
cacaagaaca tcacctgtct gtacgatatg gacattgtgg acaccaacaa tttcaacgag    300
ctgtatctgt acgaagagct catggagtgc gatatgcatc agatcatccg gtccggccag    360
cctctgactg acgcccatta ccagtcgttt gtttaccaga ttctcgccgg tgtcaagtac    420
attcattccg ccgatgttct ccatcgggat cttaaacccg caatttgct ggttaacgcc    480
gactgtgagc tcaagatttg cgatttcgga cttgcgcgtg gattctcttc cgacgacgaa    540
aagaatgccg gttcctgac agaatacgtc gccacccgt ggtacagagc cccggagatc    600
atgctctctt ccagtcttac acaaaggcc attgacatct ggtccgtggg ctgcattctg    660
gccgagcttc tggaggaaaa gccgctgttc aagggcaaga actacgtcga ccagctcaat    720
caaattctgc actacctcgg aacgccctcg gaggagactc tcaagcgaat cggcagtccc    780
agagcccagg agtacgttcg gggtcttccc ttcatgccca agattccctt ttccacgcta    840
ttccccaccg ccaaccccga ggctctggat ctgctggaga aaatgcttgc cttcgatcct    900
gcggagcgag tgacggttga ggaggctctt gagcacccct acctgaagat ctggcacgat    960
ccccgagatg agcctgtgtg tcccactccg ttcgacttct cgttcgagga ggtcaatgac   1020
atggaggcaa tgaagcagat gattctggac gaggttgtgg acttccgggc catggttcga   1080
aagcctgtcg atgagcagac acgaatcaga gacgagcaga tcgaggagca gcggagagag   1140
gaggagaagc aggaggtgga gagacaacag aaggaggctg aacgtcagaa gcaacaccag   1200
caggaagctg agagacagca acaccagcag cagcaacatc accctcaaca gcaggactct   1260
ccatccaccg tgtcgggctt ctcggactcg gaccagtctg ctaaccccca cttttacgag   1320
tacgccggct ttggagtcgg ctcacagacc tcggacatgg ccagccacc cgtcattcag   1380
```

-continued

```
cgaaaggact ctctgggtat ccccgaggag gacttcaagt accaggaccc gccaccaaag   1440
ccccaggagt ccggacgcca gggagatggc gacctggagc tcgagctgga gtacggcttg   1500
gatggatgga gaagttga                                                 1518
```

<210> SEQ ID NO 56
<211> LENGTH: 505
<212> TYPE: PRT
<213> ORGANISM: Yarrowia lipolytica

<400> SEQUENCE: 56

```
Met Ile Arg Ala Asp Arg His Thr Tyr Lys Val Phe Asn Gln Glu Phe
1               5                   10                  15

Thr Ile Asp Lys Arg Phe Gln Val Thr Lys Glu Leu Gly His Gly Ala
            20                  25                  30

Tyr Gly Ile Val Cys Ala Ala Lys Tyr Thr Gly Thr Pro Asp Gly Pro
        35                  40                  45

Gly Val Ala Ile Lys Lys Val Thr Asn Ile Phe Ser Lys Asn Ile Leu
    50                  55                  60

Cys Lys Arg Ala Leu Arg Glu Leu Lys Leu Leu Asn His Phe Arg Gly
65                  70                  75                  80

His Lys Asn Ile Thr Cys Leu Tyr Asp Met Asp Ile Val Asp Thr Asn
                85                  90                  95

Asn Phe Asn Glu Leu Tyr Leu Tyr Glu Leu Met Glu Cys Asp Met
            100                 105                 110

His Gln Ile Ile Arg Ser Gly Gln Pro Leu Thr Asp Ala His Tyr Gln
        115                 120                 125

Ser Phe Val Tyr Gln Ile Leu Ala Gly Val Lys Tyr Ile His Ser Ala
    130                 135                 140

Asp Val Leu His Arg Asp Leu Lys Pro Gly Asn Leu Leu Val Asn Ala
145                 150                 155                 160

Asp Cys Glu Leu Lys Ile Cys Asp Phe Gly Leu Ala Arg Gly Phe Ser
                165                 170                 175

Ser Asp Asp Glu Lys Asn Ala Gly Phe Leu Thr Glu Tyr Val Ala Thr
            180                 185                 190

Arg Trp Tyr Arg Ala Pro Glu Ile Met Leu Ser Phe Gln Ser Tyr Thr
        195                 200                 205

Lys Ala Ile Asp Ile Trp Ser Val Gly Cys Ile Leu Ala Glu Leu Leu
    210                 215                 220

Gly Gly Lys Pro Leu Phe Lys Gly Lys Asn Tyr Val Asp Gln Leu Asn
225                 230                 235                 240

Gln Ile Leu His Tyr Leu Gly Thr Pro Ser Glu Glu Thr Leu Lys Arg
                245                 250                 255

Ile Gly Ser Pro Arg Ala Gln Glu Tyr Val Arg Gly Leu Pro Phe Met
            260                 265                 270

Pro Lys Ile Pro Phe Ser Thr Leu Phe Pro Thr Ala Asn Pro Glu Ala
        275                 280                 285

Leu Asp Leu Leu Glu Lys Met Leu Ala Phe Asp Pro Ala Glu Arg Val
    290                 295                 300

Thr Val Glu Glu Ala Leu Glu His Pro Tyr Leu Lys Ile Trp His Asp
305                 310                 315                 320

Pro Arg Asp Glu Pro Val Cys Pro Thr Pro Phe Asp Phe Ser Phe Glu
                325                 330                 335

Glu Val Asn Asp Met Glu Ala Met Lys Gln Met Ile Leu Asp Glu Val
```

```
              340                 345                 350
Val Asp Phe Arg Ala Met Val Arg Lys Pro Val Asp Glu Gln Thr Arg
            355                 360                 365
Ile Arg Asp Glu Gln Ile Glu Glu Gln Arg Glu Glu Lys Gln
        370                 375                 380
Glu Val Glu Arg Gln Gln Lys Glu Ala Glu Arg Gln Lys Gln His Gln
385                 390                 395                 400
Gln Glu Ala Glu Arg Gln Gln His Gln Gln Gln His His Pro Gln
                405                 410                 415
Gln Gln Asp Ser Pro Ser Thr Leu Ser Gly Phe Ser Asp Ser Asp Gln
            420                 425                 430
Ser Ala Asn Pro His Phe Tyr Glu Tyr Ala Gly Phe Gly Val Gly Ser
                435                 440                 445
Gln Thr Ser Asp Met Gly Gln Pro Pro Val Ile Gln Arg Lys Asp Ser
            450                 455                 460
Leu Gly Ile Pro Glu Glu Asp Phe Lys Tyr Gln Asp Pro Pro Lys
465                 470                 475                 480
Pro Gln Glu Ser Gly Arg Gln Gly Asp Gly Asp Leu Glu Leu Glu Leu
                485                 490                 495
Glu Tyr Gly Leu Asp Gly Trp Arg Ser
            500                 505

<210> SEQ ID NO 57
<211> LENGTH: 1551
<212> TYPE: DNA
<213> ORGANISM: Pichia stipitis

<400> SEQUENCE: 57
atatactacg gacgatccgt caacaaggtg ttcaaccaag acttcattat agacaaacgg     60
ttcaagatcg taaaggagct tggccatgga gcctatggta tagtatgctc cgccaaatac    120
gacgatggat ccggcaacga cgacatcacc accaacaata tgatgctgc tggcaactcg     180
tcatcatctg atggatcgta cgtggccata agaaaaatca ccaatatctt ttccaaaaag    240
atattgtgca acggtcgct ccgtgagcta aagttgctcc agttcttccg cggtcacaag     300
aacatcacct gcttgtacga tttggacatc attcccaatc cgttgaatgg tgagttcaac    360
gaaatctatt tgtacgaaga gttgatggag tgtgacatgc accagattat ccggtcggga    420
cagccactca ccgatctgca ttaccaatct ttcatctacc aggtgttgtg cggtctcaaa    480
tacattcatc tggccgacgt gttacatcgg gacttgaagc cgggcaatct cttggttaat    540
gctgattgtg agttgaaaat ctgtgacttc gggttagccc gaggcttctc ggagaacccc    600
gaacagaatg ccggttacat gacagaatac gtagctacca gatggtacag agcccctgag    660
atcatgttga gtttcaccaa ctactcgaag gctattgata tctggtctgt aggttgtatt    720
ttggctgaac tcttaggagg aaagcctctt tccgcggaa aggactacgt agaccaattg    780
aaccagattc tattggtatt aggcactccg aaagaagcca ctttgaccaa gatcggttct    840
gtgcgagcac agaactacgt caggtcactt cccttgatga agaaggtgag ttatagcgag    900
cttttcccta cgctaacccc tttggcactt gacttacttg agaagatgtt gactcttgac    960
ccattcgaga gaatttcggt cgaagaagca ttgagccatc cttatcttgc cgtgtggcac   1020
gatccacaag acgagcccga gtgtcaggtc aaatttaact tcaaatcgtt tgaaacggta   1080
gacaatatgg acgacatgaa acaattgatc atagacgaag taagaagtt tagagagttt   1140
gttcgtaagc ccatccacga acagcagcag attcaattac agatccagtt gcaacagcgg   1200
```

-continued

```
caaatcgaag aacaagaagc agcagctgaa gcccacagaa aggaacaatt gctcgaacaa    1260
cagagacaac aacagcagca acaacaactt caagaccaac tcaatgtcat ggatatcgtt    1320
gaaactccgg ctttctccaa taacgctgat gttcagtact accagtcgat tcccaagccc    1380
caagagttgg acgagttcac tttctctcac ggcagtaact cagctgctgc taacgacttg    1440
tatgagaaca atagcttaca gtaccagaat ctgcagacgc cagctgagtt cagaaccag     1500 tctgcttcgg acttgttccg tttggaagaa gagttgggat tcggtctaga t            1551
```

<210> SEQ ID NO 58
<211> LENGTH: 517
<212> TYPE: PRT
<213> ORGANISM: Pichia stipitis

<400> SEQUENCE: 58

```
Ile Tyr Tyr Gly Arg Ser Val Asn Lys Val Phe Asn Gln Asp Phe Ile
1               5                   10                  15

Ile Asp Lys Arg Phe Lys Ile Val Lys Glu Leu Gly His Gly Ala Tyr
                20                  25                  30

Gly Ile Val Cys Ser Ala Lys Tyr Asp Asp Gly Ser Gly Asn Asp Asp
            35                  40                  45

Ile Thr Thr Asn Asn Asn Asp Ala Ala Gly Asn Ser Ser Ser Ser Asp
        50                  55                  60

Gly Ser Tyr Val Ala Ile Lys Lys Ile Thr Asn Ile Phe Ser Lys Lys
65                  70                  75                  80

Ile Leu Cys Lys Arg Ser Leu Arg Glu Leu Lys Leu Leu Gln Phe Phe
                85                  90                  95

Arg Gly His Lys Asn Ile Thr Cys Leu Tyr Asp Leu Asp Ile Ile Pro
            100                 105                 110

Asn Pro Leu Asn Gly Glu Phe Asn Glu Ile Tyr Leu Tyr Glu Glu Leu
        115                 120                 125

Met Glu Cys Asp Met His Gln Ile Ile Arg Ser Gly Gln Pro Leu Thr
    130                 135                 140

Asp Ser His Tyr Gln Ser Phe Ile Tyr Gln Val Leu Cys Gly Leu Lys
145                 150                 155                 160

Tyr Ile His Ser Ala Asp Val Leu His Arg Asp Leu Lys Pro Gly Asn
                165                 170                 175

Leu Leu Val Asn Ala Asp Cys Glu Leu Lys Ile Cys Asp Phe Gly Leu
            180                 185                 190

Ala Arg Gly Phe Ser Glu Asn Pro Glu Gln Asn Ala Gly Tyr Met Thr
        195                 200                 205

Glu Tyr Val Ala Thr Arg Trp Tyr Arg Ala Pro Glu Ile Met Leu Ser
    210                 215                 220

Phe Thr Asn Tyr Ser Lys Ala Ile Asp Ile Trp Ser Val Gly Cys Ile
225                 230                 235                 240

Leu Ala Glu Leu Leu Gly Gly Lys Pro Leu Phe Arg Gly Lys Asp Tyr
                245                 250                 255

Val Asp Gln Leu Asn Gln Ile Leu Leu Val Leu Gly Thr Pro Lys Glu
            260                 265                 270

Ala Thr Leu Thr Lys Ile Gly Ser Val Arg Ala Gln Asn Tyr Val Arg
        275                 280                 285

Ser Leu Pro Leu Met Lys Lys Val Ser Tyr Ser Glu Leu Phe Pro Asn
    290                 295                 300

Ala Asn Pro Leu Ala Leu Asp Leu Leu Glu Lys Met Leu Thr Leu Asp
```

```
                305                 310                 315                 320
        Pro Phe Glu Arg Ile Ser Val Glu Glu Ala Leu Ser His Pro Tyr Leu
                        325                 330                 335

Ala Val Trp His Asp Pro Gln Asp Glu Pro Glu Cys Gln Val Lys Phe
                        340                 345                 350

Asn Phe Lys Ser Phe Glu Thr Val Asp Asn Met Asp Met Lys Gln
                        355                 360                 365

Leu Ile Ile Asp Glu Val Lys Lys Phe Arg Glu Phe Val Arg Lys Pro
                370                 375                 380

Ile His Glu Gln Gln Gln Ile Gln Leu Gln Ile Gln Leu Gln Gln Arg
        385                 390                 395                 400

Gln Ile Glu Glu Gln Glu Ala Ala Ala Glu Ala His Arg Lys Glu Gln
                        405                 410                 415

Leu Leu Glu Gln Gln Arg Gln Gln Gln Gln Gln Gln Leu Gln Asp
                        420                 425                 430

Gln Leu Asn Val Met Asp Ile Val Glu Thr Pro Ala Phe Ser Asn Asn
                        435                 440                 445

Ala Asp Val Gln Tyr Tyr Gln Ser Ile Pro Lys Pro Gln Glu Leu Asp
                450                 455                 460

Glu Phe Thr Phe Ser His Gly Ser Asn Ser Ala Ala Asn Asp Leu
        465                 470                 475                 480

Tyr Glu Asn Asn Ser Leu Gln Tyr Gln Asn Ser Gln Thr Pro Ala Glu
                        485                 490                 495

Phe Gln Asn Gln Ser Ala Ser Asp Leu Phe Arg Leu Glu Glu Leu
                        500                 505                 510

Gly Phe Gly Leu Asp
                515

<210> SEQ ID NO 59
<211> LENGTH: 1512
<212> TYPE: DNA
<213> ORGANISM: Debaryomyces hansenii

<400> SEQUENCE: 59
atgccacaag atacagagac aatgtattct ggacgtgttg tgaataaggt ttataaccaa      60
gatttcatca ttgatagaag attcaagata gtgaaagaat tagggcatgg ggcttatgga     120
atcgtatgtt cggccaagta tgacgatgga tctgataatg aagatggaag ctatgtagct     180
attaagaaga tcaccaatat tttcagcaag aaaatattgt gtaagagatc tttgagagaa     240
ttgaaattgc tacaattctt cagaggacac aagaatatta catgtctata tgatttggat     300
attattccta atccaataac cggagaattc aacgaaatat atctttatga agaattaatg     360
gaatgtgaca tgcatcaaat cattagatca ggtcaacact taacggattc gcattatcaa     420
tcattcattt atcagacatt gtgtggttta agtatattc atagtgctga cgtcttgcat     480
cgtgatttaa aaccaggcaa tttattagtt aacgctgatt gtgaattgaa gatttgtgat     540
tttggattag caagggggtt cctggaatgt cctgagcaga atgttgggtt catgactgaa     600
tatgtagcaa ctaggtggta cagagctcct gagatcatgt tgagttttac aaattatact     660
aaagcaattg atatctggtc agttggttgt atattggccg aattattagg agggaaacca     720
attttcagag gtaaggatta tgttgatcaa ttgaatcaaa ttttacttat tttaggaacc     780
ccgaaggaat caacattaac taagattgga tctgtcagag ctcagaatta tgtgagatcc     840
ttaccgttta tgcgaaaggt tcattattct gaattgtttc caactgcaaa tccgttggct     900
```

```
ctagatttat tggaaaaaat gctcacttta gatccgtatg aaagaattac cgttgaagaa    960
gcgttaaacc atccatattt atctgtttgg catgatccac aagatgaacc agagtgtcaa   1020
ataaaatttg atttcaagtc gtttgaaact gtcgatgata tgaagtcaat gaaaaatctt   1080
ataattgatg aggtcaagaa ttttagagat tttgtcagaa aaccattaca agaacaacag   1140
caaattcaac tacaaatgca gatacagcaa caggaaagag agaaacaaaa aaatgattcc   1200
atggatttat caactccaat aaatcagcaa caatttaatg aaatgttaag ttcaagttct   1260
aactctaact ccaattcaaa ttcaaaccca gagacggggg ttaatacaga cactccaaag   1320
atgacgaatg ataatgactt gcagtattat caatctattc aaaaccaca ggaacttgat    1380 gaatttacat tttcacataa tagtaagggc ttatctccga cagataataa tgacaatcat   1440
actgatttat ttagattgga agaagaacta gggtttggct tagatggtgc tgggatgttc   1500
aataatattt aa                                                      1512

<210> SEQ ID NO 60
<211> LENGTH: 503
<212> TYPE: PRT
<213> ORGANISM: Debaryomyces hansenii

<400> SEQUENCE: 60

Met Pro Gln Asp Thr Glu Thr Met Tyr Ser Gly Arg Val Val Asn Lys
1               5                   10                  15

Val Tyr Asn Gln Asp Phe Ile Ile Asp Arg Arg Phe Lys Ile Val Lys
                20                  25                  30

Glu Leu Gly His Gly Ala Tyr Gly Ile Val Cys Ser Ala Lys Tyr Asp
            35                  40                  45

Asp Gly Ser Asp Asn Glu Asp Gly Ser Tyr Val Ala Ile Lys Lys Ile
        50                  55                  60

Thr Asn Ile Phe Ser Lys Lys Ile Leu Cys Lys Arg Ser Leu Arg Glu
65                  70                  75                  80

Leu Lys Leu Leu Gln Phe Phe Arg Gly His Lys Asn Ile Thr Cys Leu
                85                  90                  95

Tyr Asp Leu Asp Ile Ile Pro Asn Pro Ile Thr Gly Glu Phe Asn Glu
            100                 105                 110

Ile Tyr Leu Tyr Glu Glu Leu Met Glu Cys Asp Met His Gln Ile Ile
        115                 120                 125

Arg Ser Gly Gln His Leu Thr Asp Ser His Tyr Gln Ser Phe Ile Tyr
    130                 135                 140

Gln Thr Leu Cys Gly Leu Lys Tyr Ile His Ser Ala Asp Val Leu His
145                 150                 155                 160

Arg Asp Leu Lys Pro Gly Asn Leu Leu Val Asn Ala Asp Cys Glu Leu
                165                 170                 175

Lys Ile Cys Asp Phe Gly Leu Ala Arg Gly Phe Leu Glu Cys Pro Glu
            180                 185                 190

Gln Asn Val Gly Phe Met Thr Glu Tyr Val Ala Thr Arg Trp Tyr Arg
        195                 200                 205

Ala Pro Glu Ile Met Leu Ser Phe Thr Asn Tyr Thr Lys Ala Ile Asp
    210                 215                 220

Ile Trp Ser Val Gly Cys Ile Leu Ala Glu Leu Gly Gly Lys Pro
225                 230                 235                 240

Ile Phe Arg Gly Lys Asp Tyr Val Asp Gln Leu Asn Gln Ile Leu Leu
                245                 250                 255

Ile Leu Gly Thr Pro Lys Glu Ser Thr Leu Thr Lys Ile Gly Ser Val
```

```
                260                 265                 270
Arg Ala Gln Asn Tyr Val Arg Ser Leu Pro Phe Met Arg Lys Val His
            275                 280                 285

Tyr Ser Glu Leu Phe Pro Thr Ala Asn Pro Leu Ala Leu Asp Leu Leu
            290                 295                 300

Glu Lys Met Leu Thr Leu Asp Pro Tyr Glu Arg Ile Thr Val Glu Glu
305                 310                 315                 320

Ala Leu Asn His Pro Tyr Leu Ser Val Trp His Asp Pro Gln Asp Glu
                325                 330                 335

Pro Glu Cys Gln Ile Lys Phe Asp Phe Lys Ser Phe Glu Thr Val Asp
            340                 345                 350

Asp Met Lys Ser Met Lys Asn Leu Ile Ile Asp Glu Val Lys Asn Phe
            355                 360                 365

Arg Asp Phe Val Arg Lys Pro Leu Gln Glu Gln Gln Ile Gln Leu
            370                 375                 380

Gln Met Gln Ile Gln Gln Glu Arg Glu Lys Gln Lys Asn Asp Ser
385                 390                 395                 400

Met Asp Leu Ser Thr Pro Ile Asn Gln Gln Gln Phe Asn Glu Met Leu
                405                 410                 415

Ser Ser Ser Ser Asn Ser Asn Ser Asn Ser Asn Pro Glu Thr
                420                 425                 430

Gly Val Asn Thr Asp Thr Pro Lys Met Thr Asn Asp Asp Leu Gln
            435                 440                 445

Tyr Tyr Gln Ser Ile Pro Lys Pro Gln Glu Leu Asp Glu Phe Thr Phe
            450                 455                 460

Ser His Asn Ser Lys Gly Leu Ser Pro Thr Asp Asn Asp Asn His
465                 470                 475                 480

Thr Asp Leu Phe Arg Leu Glu Glu Glu Leu Gly Phe Gly Leu Asp Gly
                485                 490                 495

Ala Gly Met Phe Asn Asn Ile
            500

<210> SEQ ID NO 61
<211> LENGTH: 1488
<212> TYPE: DNA
<213> ORGANISM: Kluyveromyces lactis

<400> SEQUENCE: 61
atgaacgaat acgatgcggt agatagacac actttcaaag tgtttaatca ggacttcaca      60
gtggataaac ggttccagtt gattaaagaa ataggtcatg gttcgtacgg gattgtttgc     120
tctgcccggt tcactgaagc tgcagatgaa accacggtgg ctattaagaa agttaccaac     180
gttttctcaa agactctgct ctgcaaaaga tctctaaggg aactgaaact tctaagacat     240
tttagaggtc ataaaaatat cacttgtcta tacgatatgg atattgtgtt ccagccggac     300
ggtatgttca atggtcttta tttgtacgag gaattaatgg aatgtgatat gcatcaaatt     360
gtaaaatcgg tcagcccctt aacagatgcc cattaccaat cgttcatcta ccagattctt     420
tgtgggttaa atatattca ttcagcagac gtgctccatc gtgatttgaa gccagggaat     480
cttttggtta acgctgattg tcagttgaag atttgtgatt tcggattggc cagagggtac     540
agcgagaatc cagtagaaaa taaccaattt tgaccgaat acgtggcaac gagatggtac     600
agagcaccgg aaattatgtt gagctatcaa ggttatacaa aggctattga cgtatggtct     660
tgtggttgta tcttggcgga attgctaggt gggaaaccta tctttaaggg taaagattac     720
```

| | | |
|---|---|---|
| gtcgaccaat tgaataggat cttacaagtc ttggggactc ctccagagga aactttgaaa | 780 | |
| agaatcggat cgaaaaacgt ccaagactat atccaccagc taggatatat tccaaagata | 840 | |
| ccattcagca ctttataccc aaatgccaac ccggatgcat tgaaccttct tgagggaatg | 900 | |
| ttaagctttg atcctcaact tagaataaca gtcgatgatg ctctacaaca tccgtatttg | 960 | |
| tccatctggc atgatcctgc agatgaaccg atatgtacag aaaagttcga ttttctttt | 1020 | |
| gaaagtgtca atgagattga acaacttaaa caaatggtaa ttgacgaagt gaccgatttc | 1080 | |
| aggcaatatg tgagattacc cctcttacac gagcaacagc aacaacaggg gaagacagac | 1140 | |
| ggtggttttg atgatcaaat acgagaagat caacgcacat tcaagcgca gctagaagaa | 1200 | |
| caagtgaaca atggtagaac tgcatctaac gttccatcgt tcgatgagcc gttttctagt | 1260 | |
| caaatgatgg gttccgcgtc acaacaagat cctcttgttg gtattcattc ggataattta | 1320 | |
| ccaagccatg aacttgactt ccctcctagg cctagtgaga atgtgctaga ttcgccaatg | 1380 | |
| ggtctaagtc atcagcaaac gcataacggc tctcctgagt gccaagatat aaatgacctt | 1440 | |
| ttaggattag aaagagaact agaatttgga ttagatagac agttttaa | 1488 | |

<210> SEQ ID NO 62
<211> LENGTH: 495
<212> TYPE: PRT
<213> ORGANISM: Kluyveromyces lactis

<400> SEQUENCE: 62

Met Asn Glu Tyr Asp Ala Val Asp Arg His Thr Phe Lys Val Phe Asn
1               5                   10                  15

Gln Asp Phe Thr Val Asp Lys Arg Phe Gln Leu Ile Lys Glu Ile Gly
            20                  25                  30

His Gly Ser Tyr Gly Ile Val Cys Ser Ala Arg Phe Thr Glu Ala Ala
        35                  40                  45

Asp Glu Thr Thr Val Ala Ile Lys Lys Val Thr Asn Val Phe Ser Lys
    50                  55                  60

Thr Leu Leu Cys Lys Arg Ser Leu Arg Glu Leu Lys Leu Leu Arg His
65                  70                  75                  80

Phe Arg Gly His Lys Asn Ile Thr Cys Leu Tyr Asp Met Asp Ile Val
                85                  90                  95

Phe Gln Pro Asp Gly Met Phe Asn Gly Leu Tyr Leu Tyr Glu Glu Leu
            100                 105                 110

Met Glu Cys Asp Met His Gln Ile Val Lys Ser Gly Gln Pro Leu Thr
        115                 120                 125

Asp Ala His Tyr Gln Ser Phe Ile Tyr Gln Ile Leu Cys Gly Leu Lys
    130                 135                 140

Tyr Ile His Ser Ala Asp Val Leu His Arg Asp Leu Lys Pro Gly Asn
145                 150                 155                 160

Leu Leu Val Asn Ala Asp Cys Gln Leu Lys Ile Cys Asp Phe Gly Leu
                165                 170                 175

Ala Arg Gly Tyr Ser Glu Asn Pro Val Glu Asn Gln Phe Leu Thr
            180                 185                 190

Glu Tyr Val Ala Thr Arg Trp Tyr Arg Ala Pro Glu Ile Met Leu Ser
        195                 200                 205

Tyr Gln Gly Tyr Thr Lys Ala Ile Asp Val Trp Ser Cys Gly Cys Ile
    210                 215                 220

Leu Ala Glu Leu Leu Gly Gly Lys Pro Ile Phe Lys Gly Lys Asp Tyr
225                 230                 235                 240

| | | | | Val | Asp | Gln | Leu | Asn | Arg | Ile | Leu | Gln | Val | Leu | Gly | Thr | Pro | Pro | Glu |
|---|---|---|---|---|---|---|---|---|---|---|---|---|---|---|---|---|---|---|---|
| | | | | | | | | 245 | | | | | 250 | | | | | | 255 |

Val Asp Gln Leu Asn Arg Ile Leu Gln Val Leu Gly Thr Pro Pro Glu
                245                 250                 255

Glu Thr Leu Lys Arg Ile Gly Ser Lys Asn Val Gln Asp Tyr Ile His
            260                 265                 270

Gln Leu Gly Tyr Ile Pro Lys Ile Pro Phe Ser Thr Leu Tyr Pro Asn
        275                 280                 285

Ala Asn Pro Asp Ala Leu Asn Leu Leu Glu Gly Met Leu Ser Phe Asp
    290                 295                 300

Pro Gln Leu Arg Ile Thr Val Asp Asp Ala Leu Gln His Pro Tyr Leu
305                 310                 315                 320

Ser Ile Trp His Asp Pro Ala Asp Glu Pro Ile Cys Thr Glu Lys Phe
                325                 330                 335

Asp Phe Ser Phe Glu Ser Val Asn Glu Ile Glu Gln Leu Lys Gln Met
            340                 345                 350

Val Ile Asp Glu Val Thr Asp Phe Arg Gln Tyr Val Arg Leu Pro Leu
        355                 360                 365

Leu His Glu Gln Gln Gln Gln Gly Lys Thr Asp Gly Gly Phe Asp
    370                 375                 380

Asp Gln Ile Arg Glu Asp Gln Arg Thr Phe Gln Ala Gln Leu Glu Glu
385                 390                 395                 400

Gln Val Asn Asn Gly Arg Thr Ala Ser Asn Val Pro Ser Phe Asp Glu
                405                 410                 415

Pro Phe Ser Ser Gln Met Met Gly Ser Ala Ser Gln Gln Asp Pro Leu
            420                 425                 430

Val Gly Ile His Ser Asp Asn Leu Pro Ser His Glu Leu Asp Phe Pro
        435                 440                 445

Pro Arg Pro Ser Glu Asn Val Leu Asp Ser Pro Met Gly Leu Ser His
    450                 455                 460

Gln Gln Thr His Asn Gly Ser Pro Glu Cys Gln Asp Ile Asn Asp Leu
465                 470                 475                 480

Leu Gly Leu Glu Arg Glu Leu Glu Phe Gly Leu Asp Arg Gln Phe
                485                 490                 495

<210> SEQ ID NO 63
<211> LENGTH: 1710
<212> TYPE: DNA
<213> ORGANISM: Ashbya gossypii

<400> SEQUENCE: 63
atgtcggacg cagtggagcg tcatacattc aaggtgttca cccaggactt catggtggac     60
aagaggttcc agctaatcaa agagataggc tatggcgcgt acgggattgt gtgctcagcc    120
cggttcatgg agtcggtgga agacacaaca gtcgccatca agaaagtgac gaacgtgttc    180
tcgaaagctc tactctgcaa acggtcgcta agggagctga agctgctgcg gcactttcgg    240
gggcataaga atatcacgtg cctctacgac atggatatcg tgctgcttcc agatggctcc    300
tttaacgggc tggatctata cgaggaattg atggaatggg atatgcacca gatcatcaag    360
tccgggcagc cgctgacgga tgcgcactac cagagcttcg tctaccagat tttatgcggc    420
ctcaagtata tccactctgc ggacgtgctc catcgagatt tgaagccagg aaacctactt    480
gtgaatgctg attgtcaact caagatatgt gattttggtc tagctcgggg atatagcgaa    540
aaccccatcg aaaacgacca gttcctgacg gaatatgttg ccacgcggtg gtatcgcgcg    600
ccagaaataa tgttgagtta ccagggctac acccgcgcga tagatgtgtg gtcctgtggt    660
tgtgttctag cagaattatt aggcggaagg ccgatcttca aagggaagga ctacgttgat    720

```
cagctgaaca gaatccttca ggtgcttggt actccaccag aagagacgct aaaacgcata      780
ggttccaaaa acgtacagga ttacattcat caactagggt acattccaaa ggtgcccttc      840
gagcggctgt atcccaatgc caatccagat gcggcggatt tgttggaacg tatgttggcc      900
ctcgatccta agacacggat taccgttgac gaagctctgg agcacccata tctgtcaatc      960
tggcatgatc caagcgatga gccagtgtgc tgcaagaagt tcgactttag ttttgaaagt     1020
gtgaatgaga tggaagaact gaagcggatg gtcattgaag aagtaaagga ctttagaagg     1080
tttgttagac agcccaatat aagggacacg tcgctgcagg aacaggagga caacaaccca     1140
caacaaccac aacaaccaca acaaccacaa ccagaacagc cccaacatca gcggcagcat     1200
cagcaagcac aggcacaagc acaggcacaa gcgcatgagc agcaacagca acaccaccgt     1260
acacagtatc agcggtcggg tgctgtgcaa cgtcaaccac aaacggtgga acatggacaa     1320
catttacaac accgcagcgg acaccatagc gagcatctcc agcgagcaca tggccagcag     1380
gaacagtact tacctaaaaa agacgattcc agggcttttc aatcccgtcc agtgggtacg     1440
tccatctctg acagcagaag ctcatacgag gagcatgatt atgtacagca aatgatgttt     1500
gctcattctc ctactttagc ccacgattct tcatcgggga ttcattcaga aacctccccc     1560
gaacacaata cagacttccc cccacgacca caagagaata tgttagcatc tcccatggga     1620
ttttcggatg gtacacattc taatgcggaa tttggcgact tccttgatct ggagaaagaa     1680
ttggaatttg gtttggatag aaaaatttga                                     1710

<210> SEQ ID NO 64
<211> LENGTH: 569
<212> TYPE: PRT
<213> ORGANISM: Ashbya gossypii

<400> SEQUENCE: 64

Met Ser Asp Ala Val Glu Arg His Thr Phe Lys Val Phe Thr Gln Asp
1               5                   10                  15

Phe Met Val Asp Lys Arg Phe Gln Leu Ile Lys Glu Ile Gly Tyr Gly
            20                  25                  30

Ala Tyr Gly Ile Val Cys Ser Ala Arg Phe Met Glu Ser Val Glu Asp
        35                  40                  45

Thr Thr Val Ala Ile Lys Lys Val Thr Asn Val Phe Ser Lys Ala Leu
    50                  55                  60

Leu Cys Lys Arg Ser Leu Arg Glu Leu Lys Leu Leu Arg His Phe Arg
65                  70                  75                  80

Gly His Lys Asn Ile Thr Cys Leu Tyr Asp Met Asp Ile Val Leu Leu
                85                  90                  95

Pro Asp Gly Ser Phe Asn Gly Leu Asp Leu Tyr Glu Glu Leu Met Glu
            100                 105                 110

Trp Asp Met His Gln Ile Ile Lys Ser Gly Gln Pro Leu Thr Asp Ala
        115                 120                 125

His Tyr Gln Ser Phe Val Tyr Gln Ile Leu Cys Gly Leu Lys Tyr Ile
    130                 135                 140

His Ser Ala Asp Val Leu His Arg Asp Leu Lys Pro Gly Asn Leu Leu
145                 150                 155                 160

Val Asn Ala Asp Cys Gln Leu Lys Ile Cys Asp Phe Gly Leu Ala Arg
                165                 170                 175

Gly Tyr Ser Glu Asn Pro Ile Glu Asn Asp Gln Phe Leu Thr Glu Tyr
            180                 185                 190
```

Val Ala Thr Arg Trp Tyr Arg Ala Pro Glu Ile Met Leu Ser Tyr Gln
        195                 200                 205

Gly Tyr Thr Arg Ala Ile Asp Val Trp Ser Cys Gly Cys Val Leu Ala
    210                 215                 220

Glu Leu Leu Gly Gly Arg Pro Ile Phe Lys Gly Lys Asp Tyr Val Asp
225                 230                 235                 240

Gln Leu Asn Arg Ile Leu Gln Val Leu Gly Thr Pro Pro Glu Glu Thr
                245                 250                 255

Leu Lys Arg Ile Gly Ser Lys Asn Val Gln Asp Tyr Ile His Gln Leu
            260                 265                 270

Gly Tyr Ile Pro Lys Val Pro Phe Glu Arg Leu Tyr Pro Asn Ala Asn
        275                 280                 285

Pro Asp Ala Ala Asp Leu Leu Glu Arg Met Leu Ala Leu Asp Pro Lys
    290                 295                 300

Thr Arg Ile Thr Val Asp Glu Ala Leu Glu His Pro Tyr Leu Ser Ile
305                 310                 315                 320

Trp His Asp Pro Ser Asp Glu Pro Val Cys Cys Lys Lys Phe Asp Phe
                325                 330                 335

Ser Phe Glu Ser Val Asn Glu Met Glu Glu Leu Lys Arg Met Val Ile
            340                 345                 350

Glu Glu Val Lys Asp Phe Arg Arg Phe Val Arg Gln Pro Asn Ile Arg
        355                 360                 365

Asp Thr Ser Leu Gln Glu Gln Glu Gln Gln Pro Gln Gln Pro Gln
    370                 375                 380

Gln Pro Gln Gln Pro Gln Pro Gln Pro Gln His Gln Arg Gln His
385                 390                 395                 400

Gln Gln Ala Gln Ala Gln Ala Gln Ala His Glu Gln Gln Gln
                405                 410                 415

Gln His His Arg Thr Gln Tyr Gln Arg Ser Gly Ala Val Gln Arg Gln
            420                 425                 430

Pro Gln Thr Val Glu His Gly Gln His Leu Gln His Arg Ser Gly His
        435                 440                 445

His Ser Glu His Leu Gln Arg Ala His Gly Gln Gln Glu Gln Tyr Leu
    450                 455                 460

Pro Lys Lys Asp Asp Ser Arg Ala Phe Gln Ser Arg Pro Val Gly Thr
465                 470                 475                 480

Ser Ile Ser Asp Ser Arg Ser Ser Tyr Glu Glu His Asp Tyr Val Gln
                485                 490                 495

Gln Met Met Phe Ala His Ser Pro Thr Leu Ala His Asp Ser Phe Ile
            500                 505                 510

Gly Ile His Ser Glu Asn Leu Pro Glu His Asn Thr Asp Phe Pro Pro
        515                 520                 525

Arg Pro Gln Glu Asn Met Leu Ala Ser Pro Met Gly Phe Ser Asp Gly
    530                 535                 540

Thr His Ser Asn Ala Glu Phe Gly Asp Phe Leu Asp Leu Glu Lys Glu
545                 550                 555                 560

Leu Glu Phe Gly Leu Asp Arg Lys Ile
                565

<210> SEQ ID NO 65
<211> LENGTH: 1592
<212> TYPE: DNA
<213> ORGANISM: Aspergillus fumigatis

<400> SEQUENCE: 65

```
atgtctgatc tacagggtcg gaaggtcttc aaggtcttca accaagactt tatcgtggat      60
gaacggtaca atgtgaccaa ggagctgggc cagggtgcat acgtatcgt ttggtaggtt     120 atctgcattc tcaaggctgc gatggggtgt ctgttttcgt ctgtatccgt ggagagggct    180
gtatggcaga accacctcag aaggagtggt gaagcgtcgt ggatcgacca ttgaactgag    240
tactgatcac gatcatttga ctgtagtgct gccacgaatg ttcatactgg cgagggagtg    300
gccatcaaga aggttaccaa tgtcttcagc aagaaaattc tcgctaagcg ggcattgaga    360
gagattaagc ttcttcagca cttccgcggc caccgcaatg tacgtccaat gcttgtttgc    420
tattaaaaat cggtagggct gatcggaact gcagatcacc tgtctgtacg atatggatat    480
tccacgacca gacaatttca acgaaaccta tctctacgaa ggtgtgtgcc acaattgcta    540
tggtgcatag gaactgctga ttgattttat gcagagttga tggaatgcga tctgccgct     600 atcatccgct cgggacagcc cctgaccgac gcacattttc aatctttcat ctaccagatt    660
ttgtgtggac tcaagtatat ccattccgcc aatgtcctgc accgagatct gaagcctggt    720
aacttgctgg tcaacgcgga ctgcgagctc aagatctgcg atttcggttt ggcccgtggt    780
ttttcgatcg accccgagga gaacgccggc tacatgaccg aatatgttgc gacccggtgg    840
tatcgtgctc ccgagataat gctgagcttc cagagctaca ccaaagctag tatgtcatac    900
ctgattttgg ttgcaattag agcgccgata tgctgacgac tatagtcgac gtgtggtctg    960
taggatgcat cctggccgag ctgctcggcg gccgtccttt cttcaaaggc cgggactacg   1020
tcgaccagct caaccagatc ctgcactacc tgggtacccc caatgaggag accctgagcc   1080
gcattggatc tcctcgtgcg caggaatatg tccgcaacct gccgttcatg cccaagatcc   1140
ccttccagcg tttgttcccc aacgccaacc ccgacgcact cgatctgctc gaccgcatgc   1200
tggccttcga cccggcgtcg cgtatatcgg tcgaggaagc gctggagcac ccgtacctgc   1260
acatctggca cgacgcctcc gacgagccca cctgcccgac gacattcgac ttccacttcg   1320
aggtcgtcga cgacgtgcag gagatgcgca agatgattta cgacgaagtg gtgcgcttcc   1380
gcaacctcgt ccggcagcag tcccaggcgc aggccgccgc tgccgcgcag caacagcaac   1440
agcagattgc tcagcagacc aacgttccca tccctgacca ccagcaggga ggctggaagc   1500
aggaggagcc caagcctcag gaggtgcacg ccgcgggcgg ccatgtgaac gatctggaat   1560
cgtcattgca gcgggggatg gatgtccaat ag                                  1592
```

<210> SEQ ID NO 66
<211> LENGTH: 424
<212> TYPE: PRT
<213> ORGANISM: Aspergillus fumigatus

<400> SEQUENCE: 66

```
Met Ser Asp Leu Gln Gly Arg Lys Val Phe Lys Val Phe Asn Gln Asp
1               5                   10                  15

Phe Ile Val Asp Glu Arg Tyr Asn Val Thr Lys Glu Leu Gly Gln Gly
            20                  25                  30

Ala Tyr Gly Ile Val Cys Ala Ala Thr Asn Val His Thr Gly Glu Gly
        35                  40                  45

Val Ala Ile Lys Lys Val Thr Asn Val Phe Ser Lys Lys Ile Leu Ala
    50                  55                  60

Lys Arg Ala Leu Arg Glu Ile Lys Leu Leu Gln His Phe Arg Gly His
65                  70                  75                  80

Arg Asn Ile Thr Cys Leu Tyr Asp Met Asp Ile Pro Arg Pro Asp Asn
```

```
                85                  90                  95
Phe Asn Glu Thr Tyr Leu Tyr Glu Glu Leu Met Glu Cys Asp Leu Ala
            100                 105                 110
Ala Ile Ile Arg Ser Gly Gln Pro Leu Thr Asp Ala His Phe Gln Ser
            115                 120                 125
Phe Ile Tyr Gln Ile Leu Cys Gly Leu Lys Tyr Ile His Ser Ala Asn
            130                 135                 140
Val Leu His Arg Asp Leu Lys Pro Gly Asn Leu Leu Val Asn Ala Asp
145                 150                 155                 160
Cys Glu Leu Lys Ile Cys Asp Phe Gly Leu Ala Arg Gly Phe Ser Ile
                165                 170                 175
Asp Pro Glu Glu Asn Ala Gly Tyr Met Thr Glu Tyr Val Ala Thr Arg
            180                 185                 190
Trp Tyr Arg Ala Pro Glu Ile Met Leu Ser Phe Gln Ser Tyr Thr Lys
            195                 200                 205
Ala Ile Asp Val Trp Ser Val Gly Cys Ile Leu Ala Glu Leu Leu Gly
            210                 215                 220
Gly Arg Pro Phe Phe Lys Gly Arg Asp Tyr Val Asp Gln Leu Asn Gln
225                 230                 235                 240
Ile Leu His Tyr Leu Gly Thr Pro Asn Glu Glu Thr Leu Ser Arg Ile
                245                 250                 255
Gly Ser Pro Arg Ala Gln Glu Tyr Val Arg Asn Leu Pro Phe Met Pro
            260                 265                 270
Lys Ile Pro Phe Gln Arg Leu Phe Pro Asn Ala Asn Pro Asp Ala Leu
            275                 280                 285
Asp Leu Leu Asp Arg Met Leu Ala Phe Asp Pro Ala Ser Arg Ile Ser
            290                 295                 300
Val Glu Glu Ala Leu Glu His Pro Tyr Leu His Ile Trp His Asp Ala
305                 310                 315                 320
Ser Asp Glu Pro Thr Cys Pro Thr Thr Phe Asp Phe His Phe Glu Val
                325                 330                 335
Val Asp Asp Val Gln Glu Met Arg Lys Met Ile Tyr Asp Glu Val Val
            340                 345                 350
Arg Phe Arg Asn Leu Val Arg Gln Gln Ser Gln Ala Gln Ala Ala Ala
            355                 360                 365
Ala Ala Gln Gln Gln Gln Gln Ile Ala Gln Thr Asn Val Pro
            370                 375                 380
Ile Pro Asp His Gln Gln Gly Gly Trp Lys Gln Glu Glu Pro Lys Pro
385                 390                 395                 400
Gln Glu Val His Ala Ala Gly Gly His Val Asn Asp Leu Glu Ser Ser
                405                 410                 415
Leu Gln Arg Gly Met Asp Val Gln
            420

<210> SEQ ID NO 67
<211> LENGTH: 1566
<212> TYPE: DNA
<213> ORGANISM: Aspergillus terreus

<400> SEQUENCE: 67
atgggcgatt tacaaggtcg taagatcttc aaggtcttca accaggactt tattgtcgac      60
gaacggtaca acgtgaccaa ggagcttggt cagggtgcat acggtattgt ttggtaggtg     120
attgtcgatg ttcctctcag accccccgcg acggtcgcat ataaagatga ccacgatgca     180
```

```
agctccctct cactcggttg aacgtagcta atgacgatcg attgttctcg cttctagtgc   240
cgccacgaat acccagaccg gtgagggtgt cgccatcaaa aaggtgacca atgtgttcag   300
caagaagatc ctggccaagc gtgccctgcg agaaatcaag ctgctccagc atttccgggg   360
tcaccgcaac gtacgtcgct gttgtcgcaa tcacctgggt ccacggaagg ctgatccgtt   420
caatgtagat cacttgtctg tacgatatgg acattcctcg accggaaaac ttcaatgaga   480
catatctgta cgaaggtaag aacagcctgc cgatcaacga aataaatcat ctcttaacac   540
ttcttctctc cagaattgat ggaatgcgat ctggccgcaa tcatccgttc cggacagcct   600
ctgactgatg ctcatttcca atcattcatc taccagatcc tctgcggtct gaagtacatc   660
cactcggcca atgtgttgca cagagatctg aagcccggaa acttgctggt caatgccgac   720
tgcgaactga agatctgtga tttcggtctc gcgcgaggtt tctctatcga tcccgaggag   780
aatgccggct acatgactga atacgtcgcc acgagatggg atcgtgcccc tgaaattatg   840
ttgagcttcc aaagctacac caaggccagt acgtgcacac ccctcaccct gacccatctg   900
aaccctcgga cccttctaac gtgaatagtc gatgtgtggt ccgtaggctg cattctcgcc   960
gagctcctcg gcggccgccc cttcttcaag ggccgcgact atgtcgacca gctcaaccag  1020
atcctgcact acttgggtac acccaacgag gagaccctga ccgcatcgg ctcaccgcgt  1080
gctcaggagt acgtccgcaa cctgccctac atgccgaaga tccccttcca gcggctcttc  1140
ccgaatgcca acccggacgc tcttgacctc ctggaccgca tgctcgcctt cgacccgtcg  1200
tcgcgtatct ctgtcgaaga agccctggag cacccgtacc tgcacatctg gcatgacgcc  1260
tccgacgagc ccacctgccc cacgaccttc gatttccact ttgaggtcgt cgaggacgtt  1320
caggagatgc gtcgcatgat ctacgacgag gtcgtgcgtt ccgctctctc cgtgcggcag  1380
caatcccagg cgcaggccgc cgccgccgcc aacagcagc agatcgccaa caacgtcccc  1440
atccctgccg agcagcaggg cgtctggcga caggaggaac cgaagcccca ggaagcgctc  1500
gccgcgggcg gtggccaccc gaacgatctg aatcgtcgc tgcagcgggg tatggatgtg  1560
caatag                                                              1566
```

<210> SEQ ID NO 68
<211> LENGTH: 421
<212> TYPE: PRT
<213> ORGANISM: Aspergillus terreus

<400> SEQUENCE: 68

```
Met Gly Asp Leu Gln Gly Arg Lys Ile Phe Lys Val Phe Asn Gln Asp
1               5                   10                  15

Phe Ile Val Asp Glu Arg Tyr Asn Val Thr Lys Glu Leu Gly Gln Gly
            20                  25                  30

Ala Tyr Gly Ile Val Cys Ala Ala Thr Asn Thr Gln Thr Gly Glu Gly
        35                  40                  45

Val Ala Ile Lys Lys Val Thr Asn Val Phe Ser Lys Lys Ile Leu Ala
    50                  55                  60

Lys Arg Ala Leu Arg Glu Ile Lys Leu Leu Gln His Phe Arg Gly His
65                  70                  75                  80

Arg Asn Ile Thr Cys Leu Tyr Asp Met Asp Ile Pro Arg Pro Glu Asn
                85                  90                  95

Phe Asn Glu Thr Tyr Leu Tyr Glu Glu Leu Met Glu Cys Asp Leu Ala
            100                 105                 110

Ala Ile Ile Arg Ser Gly Gln Pro Leu Thr Asp Ala His Phe Gln Ser
        115                 120                 125
```

```
Phe Ile Tyr Gln Ile Leu Cys Gly Leu Lys Tyr Ile His Ser Ala Asn
    130                 135                 140

Val Leu His Arg Asp Leu Lys Pro Gly Asn Leu Val Asn Ala Asp
145                 150                 155                 160

Cys Glu Leu Lys Ile Cys Asp Phe Gly Leu Ala Arg Gly Phe Ser Ile
                165                 170                 175

Asp Pro Glu Glu Asn Ala Gly Tyr Met Thr Glu Tyr Val Ala Thr Arg
            180                 185                 190

Trp Tyr Arg Ala Pro Glu Ile Met Leu Ser Phe Gln Ser Tyr Thr Lys
        195                 200                 205

Ala Ile Asp Val Trp Ser Val Gly Cys Ile Leu Ala Glu Leu Leu Gly
    210                 215                 220

Gly Arg Pro Phe Phe Lys Gly Arg Asp Tyr Val Asp Gln Leu Asn Gln
225                 230                 235                 240

Ile Leu His Tyr Leu Gly Thr Pro Asn Glu Glu Thr Leu Ser Arg Ile
                245                 250                 255

Gly Ser Pro Arg Ala Gln Glu Tyr Val Arg Asn Leu Pro Tyr Met Pro
            260                 265                 270

Lys Ile Pro Phe Gln Arg Leu Phe Pro Asn Ala Asn Pro Asp Ala Leu
        275                 280                 285

Asp Leu Leu Asp Arg Met Leu Ala Phe Asp Pro Ser Ser Arg Ile Ser
    290                 295                 300

Val Glu Glu Ala Leu Glu His Pro Tyr Leu His Ile Trp His Asp Ala
305                 310                 315                 320

Ser Asp Glu Pro Thr Cys Pro Thr Thr Phe Asp Phe His Phe Glu Val
                325                 330                 335

Val Glu Asp Val Gln Glu Met Arg Arg Met Ile Tyr Asp Glu Val Val
            340                 345                 350

Arg Phe Arg Ser Leu Val Arg Gln Gln Ser Gln Ala Gln Ala Ala Ala
        355                 360                 365

Ala Ala Gln Gln Gln Gln Ile Ala Asn Asn Val Pro Ile Pro Ala Glu
    370                 375                 380

Gln Gln Gly Val Trp Arg Gln Glu Glu Pro Lys Pro Gly Glu Ala Leu
385                 390                 395                 400

Ala Ala Gly Gly Gly His Pro Asn Asp Leu Glu Ser Ser Leu Gln Arg
                405                 410                 415

Gly Met Asp Val Gln
            420

<210> SEQ ID NO 69
<211> LENGTH: 1326
<212> TYPE: DNA
<213> ORGANISM: Coprinopsis cinerea

<400> SEQUENCE: 69
atgcaaagaa gatcctttac cgctctcaac tctgtcttct gtgtcgatgc tcaatacgaa      60
ttcgtaaagg aattgggcca gggtgcttat ggctgcgtcg tagcggccag acatcgtcag     120
acgggtgaag gttgcgctat caagaagatc accaatatca acaccaagcg catcctcacc     180
aaacgatgct tgcgagagat caggcgagat agactgctgc accacttccg aggtcacaag     240
aacatcaccc tgcctctacga catggacatc gtattccagc ccaatggcaa cttcgacgag     300
gtctacctct acgaagagct gatggaggct gatctccacg ctattattcg ttcaggccag     360
cccttgacgg acgcccattt ccaatctttc atttaccaaa ccctttgtgg cctgaaatat     420
```

```
atccattccg ccaatgtcct tcaccgcgat ctcaagccag gcaaccttct cgtgaacgcc    480
gactgcgaac tcaagatctg tgattttggt ctcgctagag gatataccc  gggaagcggc    540 acgtcgcgtg cagcaggaaa ccaaggattt atgacagaat acgtggccac taggtggtat    600
cgcgcgccag aaatcatgtt gagcttcgcc aactattcaa ctgctattga tgtttggtct    660
gtcggttgta tcttggccga gctactcggt ggacggccca tcttcaaggg tagagactat    720
gtcgaccagc tgaatcaaat cctccactac cttggcaccc cttctgaaga caccctccgc    780
cgagtcggat ctcccagagc caagattac  attcgttcct tgccaatccg accaaggatc    840
tcgttctcta cgctcttccc ccaggccaat ccactcgcca ttgatctgct ttcacgcatg    900
ctctgctttg accctgctcg acgtatcagc tgcgaggaag ctctcaatca cccttatctc    960
gccgtatggc acgatcctgc tgatgaaccc aattgcgact ctatcttcga cttcagtttc   1020
gaagaagagg atagtatcga gggaatgaaa cgactgattg ttgaggaggt caacaacttc   1080
cgcgcggaag ttcgggcgca agcgcgtggt tctgcacaaa atcatcgcag taccaaggac   1140
tcggacaacc taggtattcc gtctcgagac gagattatca gctcccccgt caaggaattc   1200
ggtcctcacc ctggccatac gtccaattac accaccaacg ctccccgtgc tccgagccct   1260
attatggatg acccagtgc  agagctcgaa cgcgagcttg ctagcactca tatctccaag   1320
aaatga                                                              1326
```

<210> SEQ ID NO 70
<211> LENGTH: 441
<212> TYPE: PRT
<213> ORGANISM: Coprinopsis cinerea

<400> SEQUENCE: 70

```
Met Gln Arg Arg Ser Phe Thr Ala Leu Asn Ser Val Phe Cys Val Asp
  1               5                  10                  15

Ala Gln Tyr Glu Phe Val Lys Glu Leu Gly Gln Gly Ala Tyr Gly Cys
             20                  25                  30

Val Val Ala Ala Arg His Arg Gln Thr Gly Glu Gly Cys Ala Ile Lys
         35                  40                  45

Lys Ile Thr Asn Ile Asn Thr Lys Arg Ile Leu Thr Lys Arg Cys Leu
     50                  55                  60

Arg Glu Ile Arg Arg Asp Arg Leu Leu His His Phe Arg Gly His Lys
 65                  70                  75                  80

Asn Ile Thr Cys Leu Tyr Asp Met Asp Ile Val Phe Gln Pro Asn Gly
                 85                  90                  95

Asn Phe Asp Glu Val Tyr Leu Tyr Glu Glu Leu Met Glu Ala Asp Leu
            100                 105                 110

His Ala Ile Ile Arg Ser Gly Gln Pro Leu Thr Asp Ala His Phe Gln
        115                 120                 125

Ser Phe Ile Tyr Gln Thr Leu Cys Gly Leu Lys Tyr Ile His Ser Ala
    130                 135                 140

Asn Val Leu His Arg Asp Leu Lys Pro Gly Asn Leu Leu Val Asn Ala
145                 150                 155                 160

Asp Cys Glu Leu Lys Ile Cys Asp Phe Gly Leu Ala Arg Gly Tyr Thr
                165                 170                 175

Pro Gly Ser Gly Thr Ser Arg Ala Ala Gly Asn Gln Gly Phe Met Thr
            180                 185                 190

Glu Tyr Val Ala Thr Arg Trp Tyr Arg Ala Pro Glu Ile Met Leu Ser
        195                 200                 205
```

```
Phe Ala Asn Tyr Ser Thr Ala Ile Asp Val Trp Ser Val Gly Cys Ile
        210                 215                 220

Leu Ala Glu Leu Leu Gly Gly Arg Pro Ile Phe Lys Gly Arg Asp Tyr
225                 230                 235                 240

Val Asp Gln Leu Asn Gln Ile Leu His Tyr Leu Gly Thr Pro Ser Glu
                245                 250                 255

Asp Thr Leu Arg Arg Val Gly Ser Pro Arg Ala Gln Asp Tyr Ile Arg
            260                 265                 270

Ser Leu Pro Ile Arg Pro Arg Ile Ser Phe Ser Thr Leu Phe Pro Gln
        275                 280                 285

Ala Asn Pro Leu Ala Ile Asp Leu Leu Ser Arg Met Leu Cys Phe Asp
    290                 295                 300

Pro Ala Arg Arg Ile Ser Cys Glu Glu Ala Leu Asn His Pro Tyr Leu
305                 310                 315                 320

Ala Val Trp His Asp Pro Ala Asp Glu Pro Asn Cys Asp Ser Ile Phe
                325                 330                 335

Asp Phe Ser Phe Glu Glu Asp Ser Ile Glu Gly Met Lys Arg Leu
            340                 345                 350

Ile Val Glu Glu Val Asn Asn Phe Arg Ala Glu Val Arg Ala Gln Ala
        355                 360                 365

Arg Gly Ser Ala Gln Asn His Arg Ser Thr Lys Asp Ser Asp Asn Leu
    370                 375                 380

Gly Ile Pro Ser Arg Asp Glu Ile Ile Ser Ser Pro Val Lys Glu Phe
385                 390                 395                 400

Gly Pro His Pro Gly His Thr Ser Asn Tyr Thr Thr Asn Ala Pro Arg
                405                 410                 415

Ala Pro Ser Pro Ile Met Asp Asp Pro Ser Ala Glu Leu Glu Arg Glu
            420                 425                 430

Leu Ala Ser Thr His Ile Ser Lys Lys
        435                 440

<210> SEQ ID NO 71
<211> LENGTH: 1269
<212> TYPE: DNA
<213> ORGANISM: Schizosaccharomyces pombe

<400> SEQUENCE: 71
atggaccgtc gacatcgtgt ttaccgtgtg tttaaccagg agatgtatgt cgagcctaat     60
tttaaggtag tgaaggagtt gggtcaaggc gcttacggca ttgtttgtgc agcaagaaac    120
gtggctagca agatcaaga ggctgtagcc ataaaaaaaa ttacgaatgt gttttctaaa    180
tccattctta caaaaagagc tttgagagag ataaaactgc tgattcattt tcgtaatcat    240
cgtaacatta cttgcattta cgatctcgac attataaatc catacaattt taatgaagtt    300
tacatttacg aagagttgat ggaggccgat tgaatgcta ttattaaatc cggtcagcca    360
ttaacggatg cgcattttca atcattcatt taccagatac tttgtggttt aaagtatatt    420
cattctgcca acgttattca tcgtgactta agccaggta atctttagt taacgctgat    480 tgtgagctga aaatttgcga ttttggcctc gctcgcggat gttctgaaaa tccagaagaa    540
aatcctggtt ttatgacgga gtatgtggca acgcgctggt acagagctcc ggaaattatg    600
ctttcgttca gcagctatca taaggtatt gatgtttgga gtgttggttg cattttggca    660
gagctattag gtggaacccc tttgtttaag ggaaaagatt ttgttcatca gttaaattta    720
attttgcatc aacttggcac acctgatgag gaaaccctgt ctcatataag cagttcccgt    780
```

```
gcacaggagt atgttcgaag cttgccaaag caaagaccta ttcctttga aaccaatttt    840 cctaaagcca atcctttggc tcttgacctg cttgctaagc tcttggcttt cgaccccaac    900
agacgtattt cggttgacga tgctttagaa catccctatt tagctgtttg catgatccc    960 tctgacgaac ctgtgtgtga ttccgtcttt gatttcagct ttgaatacat tgaggatgca   1020
aatgagttac gccgtgtcat tttagatgaa gttttaaact ccgtcagaa agtccgacgc   1080 cgctctcatc caacaaaccc aacagtcaac atcccgcaac cagcccaaac cgttccatct   1140
aatgacaatg gttctttcaa tgttagtagc tcttcatcct ctcaaaccte taacaaaaag   1200 cgccatgatc attcttataa tgaaactgct gctatagacc ataagtctga tgataatcgc   1260
cataactaa                                                              1269
```

<210> SEQ ID NO 72
<211> LENGTH: 422
<212> TYPE: PRT
<213> ORGANISM: Schizosaccharomyces pombe

<400> SEQUENCE: 72

```
Met Asp Arg Arg His Arg Val Tyr Arg Val Phe Asn Gln Glu Met Tyr
1               5                   10                  15

Val Glu Pro Asn Phe Lys Val Val Lys Glu Leu Gly Gln Gly Ala Tyr
            20                  25                  30

Gly Ile Val Cys Ala Ala Arg Asn Val Ala Ser Lys Asp Gln Glu Ala
        35                  40                  45

Val Ala Ile Lys Lys Ile Thr Asn Val Phe Ser Lys Ser Ile Leu Thr
    50                  55                  60

Lys Arg Ala Leu Arg Glu Ile Lys Leu Leu Ile His Phe Arg Asn His
65                  70                  75                  80

Arg Asn Ile Thr Cys Ile Tyr Asp Leu Asp Ile Ile Asn Pro Tyr Asn
                85                  90                  95

Phe Asn Glu Val Tyr Ile Tyr Glu Glu Leu Met Glu Ala Asp Leu Asn
            100                 105                 110

Ala Ile Ile Lys Ser Gly Gln Pro Leu Thr Asp Ala His Phe Gln Ser
        115                 120                 125

Phe Ile Tyr Gln Ile Leu Cys Gly Leu Lys Tyr Ile His Ser Ala Asn
    130                 135                 140

Val Ile His Arg Asp Leu Lys Pro Gly Asn Leu Leu Val Asn Ala Asp
145                 150                 155                 160

Cys Glu Leu Lys Ile Cys Asp Phe Gly Leu Ala Arg Gly Cys Ser Glu
                165                 170                 175

Asn Pro Glu Glu Asn Pro Gly Phe Met Thr Glu Tyr Val Ala Thr Arg
            180                 185                 190

Trp Tyr Arg Ala Pro Glu Ile Met Leu Ser Phe Ser Ser Tyr His Lys
        195                 200                 205

Gly Ile Asp Val Trp Ser Val Gly Cys Ile Leu Ala Glu Leu Leu Gly
        210                 215                 220

Gly Thr Pro Leu Phe Lys Gly Lys Asp Phe Val His Gln Leu Asn Leu
225                 230                 235                 240

Ile Leu His Gln Leu Gly Thr Pro Asp Glu Glu Thr Leu Ser His Ile
                245                 250                 255

Ser Ser Ser Arg Ala Gln Glu Tyr Val Arg Ser Leu Pro Lys Gln Arg
            260                 265                 270

Pro Ile Pro Phe Glu Thr Asn Phe Pro Lys Ala Asn Pro Leu Ala Leu
```

```
              275                 280                 285
Asp Leu Leu Ala Lys Leu Leu Ala Phe Asp Pro Asn Arg Arg Ile Ser
    290                 295                 300

Val Asp Asp Ala Leu Glu His Pro Tyr Leu Ala Val Trp His Asp Pro
305                 310                 315                 320

Ser Asp Glu Pro Val Cys Asp Ser Val Phe Asp Ser Phe Glu Tyr
                325                 330                 335

Ile Glu Asp Ala Asn Glu Leu Arg Arg Val Ile Leu Asp Glu Val Leu
            340                 345                 350

Asn Phe Arg Gln Lys Val Arg Arg Ser His Pro Thr Asn Pro Thr
        355                 360                 365

Val Asn Ile Pro Gln Pro Ala Gln Thr Val Pro Ser Asn Asp Asn Gly
    370                 375                 380

Ser Phe Asn Val Ser Ser Ser Ser Ser Gln Thr Ser Asn Lys Lys
385                 390                 395                 400

Arg His Asp His Ser Tyr Asn Glu Thr Ala Ala Ile Asp His Lys Ser
                405                 410                 415

Asp Asp Asn Arg His Asn
            420

<210> SEQ ID NO 73
<211> LENGTH: 1275
<212> TYPE: DNA
<213> ORGANISM: Ustilago maydis

<400> SEQUENCE: 73
atgtcggcac atccatcaaa cccacaccgt acaccgtata acgtcctcaa tcagacgttc      60
ctgatcgaca tgcctacgc catcaccaag gacctcggcc agggtgccta cggttgcgta     120
gctgctgcca cccacaaggg caccggcgaa agcgtagcta tcaaaaagat caccaacgtc     180
ttcaccaaaa agatcctcac aaaacgtgcc ttacgagaga tcaaactttt gcgtcacttc     240
cgcggccaca aaaacatcac ctgcctatac gacatggaca ttatcgaccc cgtcggcttc     300
aacgaggtct atctctatga agagctcatg gaagctgatt tgcatgccat cattcgatcc     360
ggccagcctt tgtcggacgc tcactttcag tcgttcatct atcaaacact gtgcggcttg     420
aagtacattc attccgcctc ggtcttgcat cgagacctca gcccggcaa cttgctcatc     480 tgcgattttg gccttgcacg tggcttcgag acggatccgg aattggccaa gcaggtgggc     540
gcaggtttca tgaccgagta cgtagcaact cgatggtatc gtgcaccaga aatcatgctc     600
agctttcaga actataccac agcgatcgac atctggtcgc tcttgggagg cgaccgatc      660 ttcaagggta gggactacgt cgatcagctc aaccagattt tgcactactt gggaacgccg     720
agcgaagaga cgctccgacg cgttggatct ccgcgtgcac aggactacat cgatctcta      780 ccttatcaac cgcgcattcc tttcgatcga ctatatccac aagccaaccc tcaggcgctg     840
aacctgttgg aacgcatgct cgagttcgac cccgccaaac gcatctcctg cgaagaggca     900
ctgcagcacc catacctgtc agtatggcat gaccccgctg acgaaccgt ctgcccgcgc      960 aagtttgatt tcggctttga aagcgtcgat gaagtgcaag gcatgaagac gctcattctc    1020
gaggaagtgc gtagcttccg aaccgaagtt cgacgtcagg ccagattgat gcaacaacca    1080
aagaggcaag agtctttgcc tattccaagc agagaggaca ttcagcggag cagtccaacc    1140
gaggaaggca atccggccta ttcggtatta ggtgcaagtg cgggcatcat tcagggtgca    1200
accaactcgg agcatgccag cggcgtgctc aatgatgcgt gttcgaaaga tgtaggactt    1260
```
ggcagcttgg gttga                                                       1275

<210> SEQ ID NO 74
<211> LENGTH: 424
<212> TYPE: PRT
<213> ORGANISM: Ustilago maydis

<400> SEQUENCE: 74

```
Met Ser Ala His Pro Ser Asn Pro His Arg Thr Pro Tyr Asn Val Leu
1               5                   10                  15

Asn Gln Thr Phe Leu Ile Asp Asn Ala Tyr Ala Ile Thr Lys Asp Leu
            20                  25                  30

Gly Gln Gly Ala Tyr Gly Cys Val Ala Ala Thr His Lys Gly Thr
        35                  40                  45

Gly Glu Ser Val Ala Ile Lys Lys Ile Thr Asn Val Phe Thr Lys Lys
    50                  55                  60

Ile Leu Thr Lys Arg Ala Leu Arg Glu Ile Lys Leu Leu Arg His Phe
65                  70                  75                  80

Arg Gly His Lys Asn Ile Thr Cys Leu Tyr Asp Met Asp Ile Ile Asp
                85                  90                  95

Pro Val Gly Phe Asn Glu Val Tyr Leu Tyr Glu Glu Leu Met Glu Ala
            100                 105                 110

Asp Leu His Ala Ile Ile Arg Ser Gly Gln Pro Leu Ser Asp Ala His
        115                 120                 125

Phe Gln Ser Phe Ile Tyr Gln Thr Leu Cys Gly Leu Lys Tyr Ile His
    130                 135                 140

Ser Ala Ser Val Leu His Arg Asp Leu Lys Pro Gly Asn Leu Leu Ile
145                 150                 155                 160

Cys Asp Phe Gly Leu Ala Arg Gly Phe Glu Thr Asp Pro Glu Leu Ala
                165                 170                 175

Lys Gln Val Gly Ala Gly Phe Met Thr Glu Tyr Val Ala Thr Arg Trp
            180                 185                 190

Tyr Arg Ala Pro Glu Ile Met Leu Ser Phe Gln Asn Tyr Thr Thr Ala
        195                 200                 205

Ile Asp Ile Trp Ser Leu Leu Gly Gly Arg Pro Ile Phe Lys Gly Arg
    210                 215                 220

Asp Tyr Val Asp Gln Leu Asn Gln Ile Leu His Tyr Leu Gly Thr Pro
225                 230                 235                 240

Ser Glu Glu Thr Leu Arg Arg Val Gly Ser Pro Arg Ala Gln Asp Tyr
                245                 250                 255

Ile Arg Ser Leu Pro Tyr Gln Pro Arg Ile Pro Phe Asp Arg Leu Tyr
            260                 265                 270

Pro Gln Ala Asn Pro Gln Ala Leu Asn Leu Leu Glu Arg Met Leu Glu
        275                 280                 285

Phe Asp Pro Ala Lys Arg Ile Ser Cys Glu Glu Ala Leu Gln His Pro
    290                 295                 300

Tyr Leu Ser Val Trp His Asp Pro Ala Asp Glu Pro Val Cys Pro Arg
305                 310                 315                 320

Lys Phe Asp Phe Gly Phe Glu Ser Val Asp Glu Val Gln Gly Met Lys
                325                 330                 335

Thr Leu Ile Leu Glu Glu Val Arg Ser Phe Arg Thr Glu Val Arg Arg
            340                 345                 350

Gln Ala Arg Leu Met Gln Gln Pro Lys Arg Gln Glu Ser Leu Pro Ile
        355                 360                 365
```

-continued

```
Pro Ser Arg Glu Asp Ile Gln Arg Ser Ser Pro Thr Glu Glu Gly Asn
    370                 375                 380

Pro Ala Tyr Ser Val Leu Gly Ala Ser Ala Gly Ile Ile Gln Gly Ala
385                 390                 395                 400

Thr Asn Ser Glu His Ala Ser Gly Val Leu Asn Asp Ala Cys Ser Lys
                405                 410                 415

Asp Val Gly Leu Gly Ser Leu Gly
            420

<210> SEQ ID NO 75
<211> LENGTH: 23
<212> TYPE: DNA
<213> ORGANISM: artificial sequence
<220> FEATURE:
<223> OTHER INFORMATION: primer

<400> SEQUENCE: 75
ctatgcgcac ccgttctcgg agc                                            23

<210> SEQ ID NO 76
<211> LENGTH: 22
<212> TYPE: DNA
<213> ORGANISM: artificial sequence
<220> FEATURE:
<223> OTHER INFORMATION: primer

<400> SEQUENCE: 76
cgctcatgag cccgaagtgg cg                                             22

<210> SEQ ID NO 77
<211> LENGTH: 43
<212> TYPE: DNA
<213> ORGANISM: artificial sequence
<220> FEATURE:
<223> OTHER INFORMATION: primer

<400> SEQUENCE: 77
ccgctgctag gcgcgccgtg tctgaaaacg gaagaggagt agg                      43

<210> SEQ ID NO 78
<211> LENGTH: 44
<212> TYPE: DNA
<213> ORGANISM: artificial sequence
<220> FEATURE:
<223> OTHER INFORMATION: primer

<400> SEQUENCE: 78
gcagggatgc ggccgctgac ataacagaca tactccaagc tgcc                     44

<210> SEQ ID NO 79
<211> LENGTH: 45
<212> TYPE: DNA
<213> ORGANISM: artificial sequence
<220> FEATURE:
<223> OTHER INFORMATION: primer

<400> SEQUENCE: 79
ccgctgctag gcgcgccgtg catttggctt tttgattgat tgtac                    45

<210> SEQ ID NO 80
<211> LENGTH: 47
<212> TYPE: DNA
<213> ORGANISM: artificial sequence
<220> FEATURE:
<223> OTHER INFORMATION: primer
```

<400> SEQUENCE: 80
gcagggatgc ggccgctgac acttttattt tctcttttg cactcct    47

<210> SEQ ID NO 81
<211> LENGTH: 20
<212> TYPE: DNA
<213> ORGANISM: artificial sequence
<220> FEATURE:
<223> OTHER INFORMATION: primer

<400> SEQUENCE: 81
ccgctgctag gcgcgccgtg    20

<210> SEQ ID NO 82
<211> LENGTH: 25
<212> TYPE: DNA
<213> ORGANISM: artificial sequence
<220> FEATURE:
<223> OTHER INFORMATION: primer

<400> SEQUENCE: 82
gagcaatgaa cccaataacg aaatc    25

<210> SEQ ID NO 83
<211> LENGTH: 20
<212> TYPE: DNA
<213> ORGANISM: artificial sequence
<220> FEATURE:
<223> OTHER INFORMATION: primer

<400> SEQUENCE: 83
gcagggatgc ggccgctgac    20

<210> SEQ ID NO 84
<211> LENGTH: 25
<212> TYPE: DNA
<213> ORGANISM: artificial sequence
<220> FEATURE:
<223> OTHER INFORMATION: primer

<400> SEQUENCE: 84
cttgacgttc gttcgactga tgagc    25

<210> SEQ ID NO 85
<211> LENGTH: 448
<212> TYPE: DNA
<213> ORGANISM: Saccharomyces cerevisiae

<400> SEQUENCE: 85
cccattaccg acatttgggc gctatacgtg catatgttca tgtatgtatc tgtatttaaa    60
acacttttgt attattttc ctcatatatg tgtataggtt tatacggatg atttaattat    120
tacttcacca cccttattt caggctgata tcttagcctt gttactagtt agaaaaagac    180 attttgctg tcagtcactg tcaagagatt cttttgctgg catttcttct agaagcaaaa    240
agagcgatgc gtcttttccg ctgaaccgtt ccagcaaaaa agactaccaa cgcaatatgg    300
attgtcagaa tcatataaaa gagaagcaaa taactccttg tcttgtatca attgcattat    360
aatatcttct tgttagtgca atatcatata gaagtcatcg aaatagatat taagaaaaac    420
aaactgtaca atcaatcaat caatcatc    448

<210> SEQ ID NO 86

<211> LENGTH: 270
<212> TYPE: DNA
<213> ORGANISM: Saccharomyces cerevisiae

<400> SEQUENCE: 86

```
gacctcgagt catgtaatta gttatgtcac gcttacattc acgccctccc cccacatccg      60
ctctaaccga aaaggaagga gttagacaac ctgaagtcta ggtccctatt tattttttta     120
tagttatgtt agtattaaga acgttattta tatttcaaat ttttcttttt tttctgtaca     180
gacgcgtgta cgcatgtaac attatactga aaaccttgct tgagaaggtt ttgggacgct     240
cgaaggcttt aatttgcggc cggtacccaa                                      270
```

<210> SEQ ID NO 87
<211> LENGTH: 643
<212> TYPE: DNA
<213> ORGANISM: Saccharomyces cerevisiae

<400> SEQUENCE: 87

```
gaaatgaata acaatactga cagtactaaa taattgccta cttggcttca catacgttgc      60
atacgtcgat atagataata atgataatga cagcaggatt atcgtaatac gtaatagttg     120
aaaatctcaa aaatgtgtgg gtcattacgt aaataatgat aggaatggga ttcttctatt     180
tttcctttt ccattctagc agccgtcggg aaaacgtggc atcctctctt tcgggctcaa      240
ttggagtcac gctgccgtga gcatcctctc tttccatatc taacaactga gcacgtaacc     300
aatggaaaag catgagctta gcgttgctcc aaaaaagtat tggatggtta ataccatttg     360
tctgttctct tctgactttg actcctcaaa aaaaaaaat ctacaatcaa cagatcgctt      420
caattacgcc ctcacaaaaa cttttttcct tcttcttcgc ccacgttaaa ttttatccct     480
catgttgtct aacggatttc tgcacttgat ttattataaa aagacaaaga cataatactt     540
ctctatcaat ttcagttatt gttcttcctt gcgttattct tctgttcttc ttttctttt     600
gtcatatata accataacca agtaatacat attcaaatct aga                       643
```

<210> SEQ ID NO 88
<211> LENGTH: 316
<212> TYPE: DNA
<213> ORGANISM: Saccharomyces cerevisiae

<400> SEQUENCE: 88

```
gagtaagcga atttcttatg atttatgatt tttattatta aataagttat aaaaaaaata      60
agtgtataca aattttaaag tgactcttag gttttaaaac gaaaattctt attcttgagt     120
aactctttcc tgtaggtcag gttgctttct caggtatagc atgaggtcgc tcttattgac     180
cacacctcta ccggcatgcc gagcaaatgc ctgcaaatcg ctccccattt cacccaattg     240
tagatatgct aactccagca atgagttgat gaatctcggt gtgtatttta tgtcctcaga     300
ggacaacacc tgtggt                                                     316
```

<210> SEQ ID NO 89
<211> LENGTH: 753
<212> TYPE: DNA
<213> ORGANISM: Saccharomyces cerevisiae

<400> SEQUENCE: 89

```
gcatgcttgc atttagtcgt gcaatgtatg actttaagat ttgtgagcag gaagaaaagg      60
gagaatcttc taacgataaa cccttgaaaa actgggtaga ctacgctatg ttgagttgct     120
acgcaggctg cacaattaca cgagaatgct cccgcctagg atttaaggct aagggacgtg     180
```

```
caatgcagac gacagatcta aatgaccgtg tcggtgaagt gttcgccaaa cttttcggtt        240
aacacatgca gtgatgcacg cgcgatggtg ctaagttaca tatatatata tatagccata        300
gtgatgtcta agtaaccttt atggtatatt tcttaatgtg gaaagatact agcgcgcgca        360
cccacacaca agcttcgtct tttcttgaag aaaagaggaa gctcgctaaa tgggattcca        420
ctttccgttc cctgccagct gatggaaaaa ggttagtgga acgatgaaga ataaaaagag        480
agatccactg aggtgaaatt tcagctgaca gcgagtttca tgatcgtgat gaacaatggt        540
aacgagttgt ggctgttgcc agggagggtg gttctcaact tttaatgtat ggccaaatcg        600
ctacttgggt ttgttatata acaaagaaga aataatgaac tgattctctt cctccttctt        660
gtcctttctt aattctgttg taattacctt cctttgtaat tttttttgta attattcttc        720
ttaataatcc aaacaaacac acatattaca ata                                    753

<210> SEQ ID NO 90
<211> LENGTH: 33
<212> TYPE: DNA
<213> ORGANISM: artificial sequence
<220> FEATURE:
<223> OTHER INFORMATION: primer

<400> SEQUENCE: 90
ccatggtgga tccgtggtga aaatgaagga aat                                     33

<210> SEQ ID NO 91
<211> LENGTH: 32
<212> TYPE: DNA
<213> ORGANISM: artificial sequence
<220> FEATURE:
<223> OTHER INFORMATION: primer

<400> SEQUENCE: 91
ccatggggat ccatcttcat aaacgtttat ca                                      32
```

YEAST WITH INCREASED BUTANOL TOLERANCE INVOLVING CELL WALL INTEGRITY PATHWAY

CROSS-REFERENCE TO RELATED APPLICATIONS

This application is related to and claims the benefit of priority to U.S. Provisional Patent Application No. 61/141,009, filed Dec. 29, 2008, the entirety of which is herein incorporated by reference.

FIELD OF THE INVENTION

The invention relates to the field of microbiology and genetic engineering. More specifically, yeast genes that are involved in the cell response to butanol were identified. These genes may be engineered to improve growth yield in the presence of butanol.

BACKGROUND OF THE INVENTION

Butanol is an important industrial chemical, useful as a fuel additive, as a feedstock chemical in the plastics industry, and as a foodgrade extractant in the food and flavor industry. Each year 10 to 12 billion pounds of butanol are produced by petrochemical means and the need for this commodity chemical will likely increase.

Butanol may be made through chemical synthesis or by fermentation. Isobutanol is produced biologically as a by-product of yeast fermentation. It is a component of "fusel oil" that forms as a result of incomplete metabolism of amino acids by this group of fungi. Isobutanol is specifically produced from catabolism of L-valine and the yield is typically very low. Additionally, recombinant microbial production hosts, expressing a 1-butanol biosynthetic pathway (Donaldson et al., U.S. Patent Application Publication No. US20080182308A1), a 2-butanol biosynthetic pathway (Donaldson et al., U.S. Patent Publication Nos. US 20070259410A1 and US 20070292927), and an isobutanol biosynthetic pathway (Maggio-Hall et al., U.S. Patent Publication No. US 20070092957) have been described.

Biological production of butanols is believed to be limited by butanol toxicity to the host microorganism used in fermentation for butanol production. Yeast are typically sensitive to butanol in the medium. Using a screen for 1-butanol insensitive *Saccharomyces cerevisiae* mutants, Lorenz et al. (Molec. Biol. of the Cell (2000) 11:183-199) identified proteins that regulate polarized growth (BUD8, BEM1, BEM4, and FIG. 1), mitochondrial function (MSM1, MRP21, and HM11), and a transcriptional regulator (CHD1). They also found that 1-butanol stimulates filamentous growth in haploid cells and induces cell elongation and changes in budding pattern, leading to a pseudohyphal morphology. Ashe et al. (The EMBO Journal (2001) 20:6464-6474) found that butanol brings about a rapid inhibition of translation at the initiation step in *Saccharomyces cerevisiae*. The GCD1-P180 allele has a single amino acid change in Gcd1p, which is part of the eIF2B guanine nucleotide complex that is responsible for recycling eIF2-GDP to eIF2-GTP, that allows translational regulation upon butanol addition. Smirnova et al. (Molecular and Cellular Bioloty (2005) 25:9340-9340) found by using microarray analysis that with addition of fusel alcohol, there is widespread translational reprogramming in yeast. These studies all indicate the complexity of butanol sensitivity in yeast.

Van Voorst et al. (Yeast 23(5)351-359 (2006)) found that the MAP kinase of the cell wall integrity pathway, Slt2p, was phosphorylated when cells were treated with 6% ethanol. Isoamyl alcohol induces a phenotype that resembles pseudohyphae in *S. cerevisiae*, that requires the activity of SWE1 and SLT2 (Martinez-Anaya et al. (2003) Journal of Cell Science 116, 3423-3431, (2003); Levin, D. E. (2005) Microbiol. Mol. Biol. Rev.: 262-291). A complete set of *S. cerevisiae* homozygous deletions was screened for tolerance to the aliphatic alcohols ethanol, propanol and pentanol (Fuijta et al. (2006) FEMS Yeast Res 6:744-750). Mutant SLT2 deletion strains were hypersensitive to ethanol and propanol but not to pentanol, There remains a need for yeast cells with increased tolerance to butanol, as well as methods of producing butanols using yeast host strains that are more tolerant to these chemicals. To this end applicants have Identified genes in yeast that are involved in butanol tolerance, that can be engineered to increase the level of butanol tolerance in yeast cells used for butanol production.

SUMMARY OF THE INVENTION

Provided herein are recombinant yeast cells comprising: a) a butanol biosynthetic pathway; and b) at least one genetic modification which increases activity of the cell wall integrity pathway; wherein the butanol biosynthetic pathway comprises at least one gene that is heterologous to the yeast cell and wherein the yeast cell has an increase in tolerance to butanol as compared with a yeast cell that lacks the at least one genetic modification of (b).

In some embodiments, the cell has at least about a 25% improvement in growth yield in 1% (w/v) isobutanol as compared to a parental cell having no increase in activity of the cell wall integrity pathway. In some embodiments, the yeast is selected from the group consisting of *Saccharomyces, Schizosaccharomyces, Hansenula, Candida, Kluyveromyces, Yarrowia* and *Pichia*.

In some embodiments, the genetic modification increases activity of the mitogen-activated protein kinase module of the cell wall integrity pathway. In some embodiments, the genetic modification increases SLT2p serine/threonine MAP kinase activity. In some embodiments, the modification increasing SLT2 serine/threonine MAP kinase activity is overexpression of an SLT2 protein encoding gene.

In some embodiments, the SLT2 protein encoding gene encodes a protein having an amino acid sequence with at least about 90% sequence identity to a sequence selected from the group consisting of SEQ ID NOs:50, 52, 54, 56, 58, 60, 62, 64, 66, 68, 70, 72, and 74 based on Clustal W method of alignment using the default parameters of GAP PENALTY=10, GAP LENGTH PENALTY=0.1, and Gonnet 250 series of protein weight matrix. In some embodiments, the genetic modification increasing the activity of the mitogen-activated protein kinase module is the overexpression of a gene selected from the group consisting of WSC1, WSC2, WSC3, MID2, MTL1, HOR2, YPT7, ROM2, BEM2, ABC1, RHO1, EPT1, STB5, YDJ1, SSD1, CNA1, KRE11, EXG1, EXG2, DGK1, HCR1, LOC1, PDR2, PDR8 and RLM1.

Also provided herein is a recombinant yeast cell comprising a butanol biosynthetic pathway and at least one heterologous SLT2 protein encoding gene. In some embodiments, the butanol biosynthetic pathway comprises at least one gene that is heterologous to the yeast cell. In some embodiments, the yeast cell has an increased tolerance to butanol as compared to a yeast cell that does not comprise at least one heterologous SLT2 protein encoding gene.

In some embodiments, the butanol biosynthetic pathway is selected from the group consisting of: a) a 1-butanol biosynthetic pathway; b) a 2-butanol biosynthetic pathway; and c) an isobutanol biosynthetic pathway. In some embodiments, the 1-butanol biosynthetic pathway comprises at least one gene encoding a polypeptide that performs at least one of the following substrate to product conversions: a) acetyl-CoA to acetoacetyl-CoA, as catalyzed by acetyl-CoA acetyltransferase; b) acetoacetyl-CoA to 3-hydroxybutyryl-CoA, as catalyzed by 3-hydroxybutyryl-CoA dehydrogenase; c) 3-hydroxybutyryl-CoA to crotonyl-CoA, as catalyzed by crotonase; d) crotonyl-CoA to butyryl-CoA, as catalyzed by butyryl-CoA dehydrogenase; e) butyryl-CoA to butyraldehyde, as catalyzed by butyraldehyde dehydrogenase; and f) butyraldehyde to 1-butanol, as catalyzed by 1-butanol dehydrogenase. In some embodiments, the 2-butanol biosynthetic pathway comprises at least one gene encoding a polypeptide that performs at least one of the following substrate to product conversions: a) pyruvate to alpha-acetolactate, as catalyzed by acetolactate synthase; b) alpha-acetolactate to acetoin, as catalyzed by acetolactate decarboxylase; c) acetoin to 2,3-butanediol, as catalyzed by butanediol dehydrogenase; d) 2,3-butanediol to 2-butanone, as catalyzed by butanediol dehydratase; and e) 2-butanone to 2-butanol, as catalyzed by 2-butanol dehydrogenase. In some embodiments, the isobutanol biosynthetic pathway comprises at least one gene encoding a polypeptide that performs at least one of the following substrate to product conversions: a) pyruvate to acetolactate, as catalyzed by acetolactate synthase; b) acetolactate to 2,3-dihydroxyisovalerate, as catalyzed by acetohydroxy acid isomeroreductase; c) 2,3-dihydroxyisovalerate to α-ketoisovalerate, as catalyzed by acetohydroxy acid dehydratase or dihydroxyacid dehydratase; d) α-ketoisovalerate to isobutyraldehyde, as catalyzed by a branched-chain keto acid decarboxylase; and e) isobutyraldehyde to isobutanol, as catalyzed by a branched-chain alcohol dehydrogenase.

Also provided herein are methods for the production of 1-butanol comprising growing a recombinant yeast cell under conditions where 1-butanol is produced and optionally recovering the 1-butanol. Also provided are methods for the production of 2-butanol comprising growing a recombinant yeast cell under conditions where 2-butanol is produced and optionally recovering the 2-butanol. Also provided are methods for the production of isobutanol comprising growing a recombinant yeast cell of under conditions where isobutanol is produced and optionally recovering the isobutanol.

Also provided are methods for producing a recombinant yeast cell having increased tolerance to butanol comprising: a) providing a recombinant yeast cell comprising a butanol biosynthetic pathway selected from the group consisting of: i) a 1-butanol biosynthetic pathway; ii) a 2-butanol biosynthetic pathway; and iii) an isobutanol biosynthetic pathway; and b) engineering the yeast cell of (a) to comprise at least one genetic modification which increases activity of the cell wall integrity pathway wherein the genetic modification increases SLT2p serine/threonine MAP kinase activity.

Also provided herein is a method for improving fermentative production of butanol comprising:
a) providing a recombinant yeast cell comprising a butanol biosynthetic pathway selected from the group consisting of:
  i) a 1-butanol biosynthetic pathway
  ii) a 2-butanol biosynthetic pathway; and
  iii) an isobutanol biosynthetic pathway;
wherein said yeast cell also comprises at least one genetic modification that increases activity of the cell wall integrity pathway; and
b) contacting said yeast cell with fermentable sugar whereby said yeast cell produces butanol and wherein said yeast cell has improved tolerance to said butanol as compared to a yeast cell without at least one genetic modification that increases activity of the cell wall integrity pathway. Said method also provides for improved production of butanol as compared to a yeast cell without at least one genetic modification that increases activity of the cell wall integrity pathway.

BRIEF DESCRIPTION OF THE DRAWINGS AND SEQUENCE DESCRIPTIONS

The various embodiments of the invention can be more fully understood from the following detailed description and the accompanying sequence descriptions, which form a part of this application.

Figure 2:
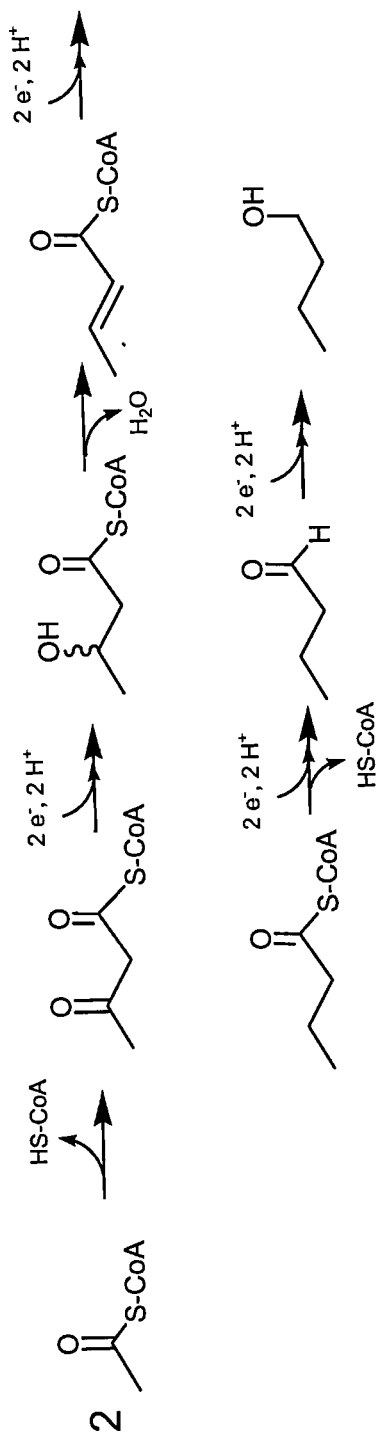
Figure 3:
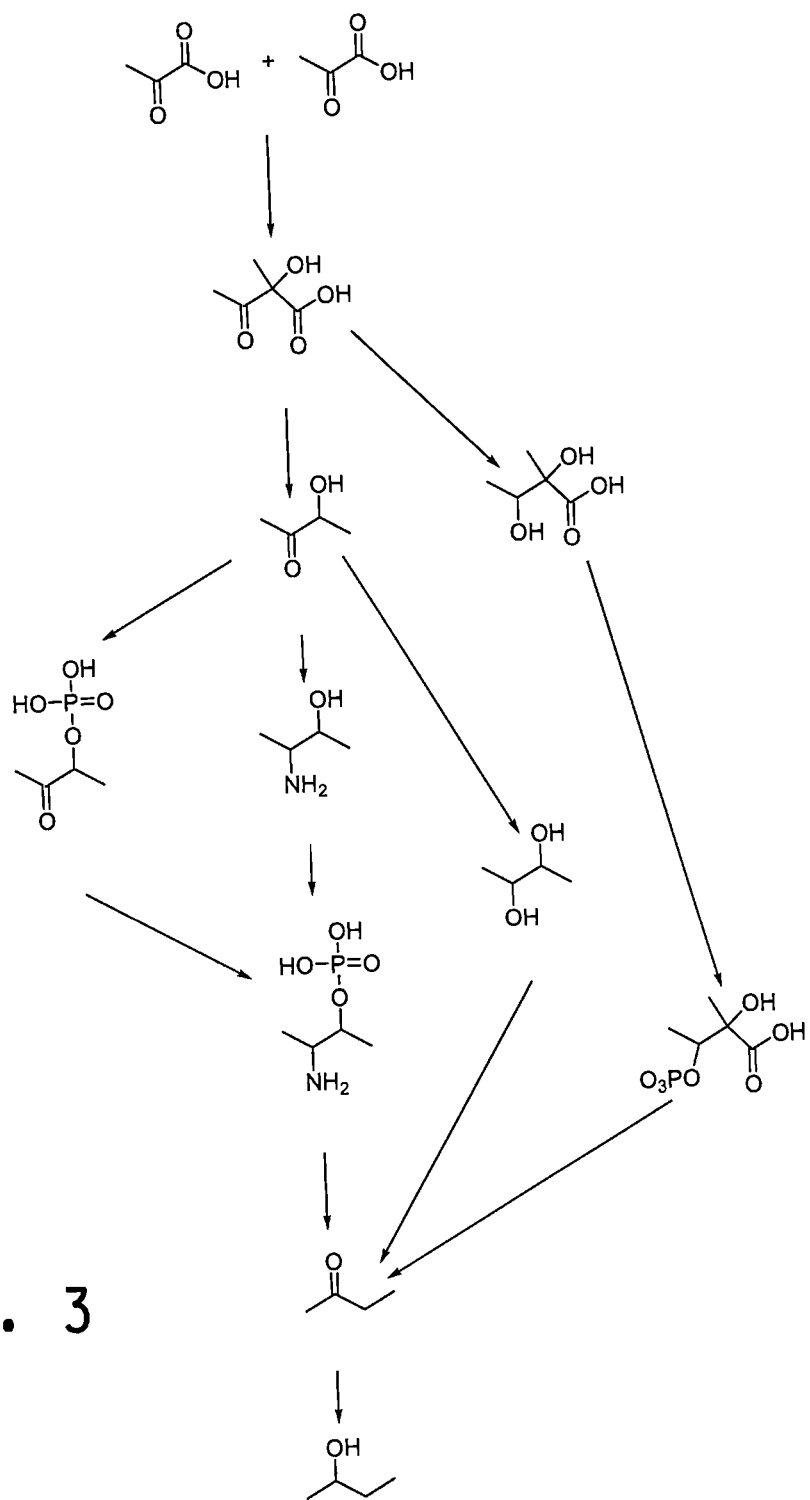
Figure 4:
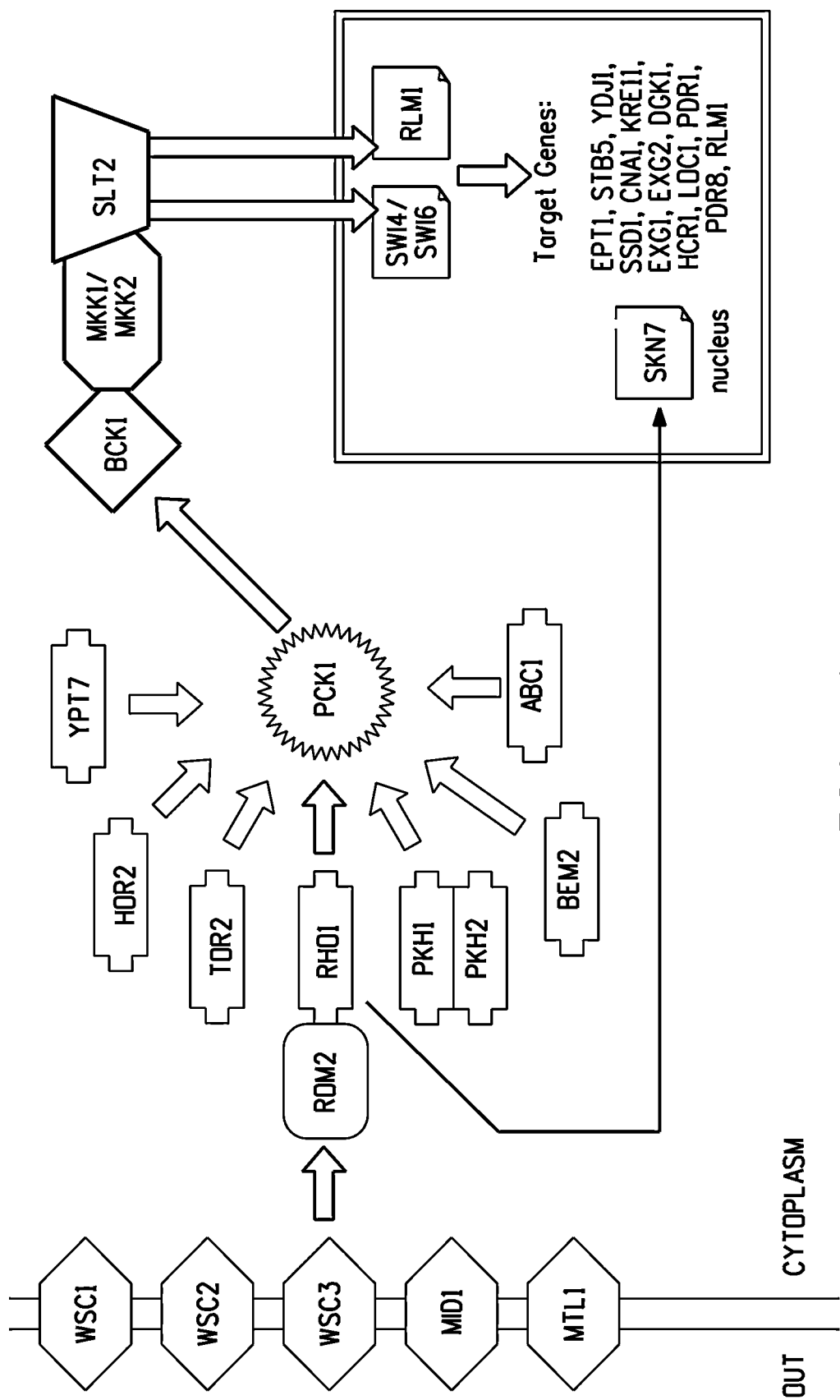

FIG. 1 depicts isobutanol biosynthetic pathways.
FIG. 2 depicts 1-butanol biosynthetic pathways.
FIG. 3 depicts 2-butanol biosynthetic pathways.
FIG. 4 is a cell wall integrity (CWI) pathway schematic.

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

TABLE 1

Summary of Coding Region and Protein SEQ ID Numbers for 1-Butanol Biosynthetic Pathway

| Description | SEQ ID NO: Nucleic acid | SEQ ID NO: Peptide |
|---|---|---|
| Acetyl-CoA acetyltransferase thlA from *Clostridium acetobutylicum* ATCC 824 | 1 | 2 |
| Acetyl-CoA acetyltransferase thlB from *Clostridium acetobutylicum* ATCC 824 | 3 | 4 |
| Acetyl-CoA acetyltransferase from *Saccharomyces cerevisiae* | 39 | 40 |
| 3-Hydroxybutyryl-CoA dehydrogenase from *Clostridium acetobutylicum* ATCC 824 | 5 | 6 |
| Crotonase from *Clostridium acetobutylicum* ATCC 824 | 7 | 8 |
| Putative trans-enoyl CoA reductase from *Clostridium acetobutylicum* ATCC 824 | 9 | 10 |
| Butyraldehyde dehydrogenase from *Clostridium beijerinckii* NRRL B594 | 11 | 12 |
| 1-Butanol dehydrogenase bdhB from *Clostridium acetobutylicum* ATCC 824 | 13 | 14 |
| 1-Butanol dehydrogenase bdhA from *Clostridium acetobutylicum* ATCC 824 | 15 | 16 |

TABLE 2

Summary of Coding Region and Protein SEQ ID Numbers for 2-Butanol Biosynthetic Pathway

| Description | SEQ ID NO: Nucleic acid | SEQ ID NO: Peptide |
|---|---|---|
| budA, acetolactate decarboxylase from *Klebsiella pneumoniae* ATCC 25955 | 17 | 18 |
| budB, acetolactate synthase from *Klebsiella pneumoniae* ATCC 25955 | 19 | 20 |
| budC, butanediol dehydrogenase from *Klebsiella pneumoniae* IAM1063 | 21 | 22 |

TABLE 2-continued

Summary of Coding Region and Protein SEQ ID Numbers for 2-Butanol Biosynthetic Pathway

| Description | SEQ ID NO: Nucleic acid | SEQ ID NO: Peptide |
|---|---|---|
| pddA, butanediol dehydratase alpha subunit from *Klebsiella oxytoca* ATCC 8724 | 23 | 24 |
| pddB, butanediol dehydratase beta subunit from *Klebsiella oxytoca* ATCC 8724 | 25 | 26 |
| pddC, butanediol dehydratase gamma subunit from *Klebsiella oxytoca* ATCC 8724 | 27 | 28 |
| sadH, 2-butanol dehydrogenase from *Rhodococcus ruber* 219 | 29 | 30 |

TABLE 3

Summary of Coding Region and Protein SEQ ID Numbers for Isobutanol Biosynthetic Pathway

| Description | SEQ ID NO: Nucleic acid | SEQ ID NO: Peptide |
|---|---|---|
| *Klebsiella pneumoniae* budB (acetolactate synthase) | 19 | 20 |
| *Bacillus subtilis* alsS (acetolactate synthase) | 41 | 42 |
| *E. coli* ilvC (acetohydroxy acid reductoisomerase) | 31 | 32 |
| *S. cerevisiae* ILV5 (acetohydroxy acid reductoisomerase) | 43 | 44 |
| *B. subtilis* ilvC (acetohydroxy acid reductoisomerase) | 45 | 46 |
| *E. coli* ilvD (acetohydroxy acid dehydratase) | 33 | 34 |
| *S. cerevisiae* ILV3 (Dihydroxyacid dehydratase) | 47 | 48 |
| *Lactococcus lactis* kivD (branched-chain α-keto acid decarboxylase), codon optimized | 35 | 36 |
| *E. coli* yqhD (branched-chain alcohol dehydrogenase) | 37 | 38 |

TABLE 4

Summary of SLT2 Coding Region and Protein SEQ ID Numbers

| Organism | SEQ ID NO: Nucleic acid | SEQ ID NO: Peptide |
|---|---|---|
| *Saccharomyces cerevisiae* | 49 | 50 |
| *Candida glabrata* | 51 | 52 |
| *Candida albicans* | 53 | 54 |
| *Yarrowia lipolytica* | 55 | 56 |
| *Pichia stipitis* | 57 | 58 |
| *Debaryomyces hansenii* | 59 | 60 |
| *Kluyveromyces lactis* | 61 | 62 |
| *Ashbya gossypii* | 63 | 64 |
| *Apergillus fumigatus* | 65 | 66 |
| *Apergillus terreus* | 67 | 68 |
| *Coprinopsis cinerea* | 69 | 70 |
| *Schizosaccharomyces pombe* | 71 | 72 |
| *Ustilago maydis* | 73 | 74 |

SEQ ID NOs:75 and 76 are primers used for sequencing the ends of the *S. cerevisiae* genomic DNA insert of the plasmid in the yBUT11 clone.

SEQ ID NOs:77 and 78 are primers for PCR of iYDR006C.

SEQ ID NOs:79 and 80 are primers for PCR of iYDR008C.

SEQ ID NOs:81 and 82 are primers for PCR of upTRP1 DR UR.

SEQ ID NOs:83 and 84 are primers for PCR of RA3* DR downTRP1.

SEQ ID NO:85 is the nucleotide sequence of the CUP1 promoter.

SEQ ID NO:86 is the nucleotide sequence of the CYC1 terminator.

SEQ ID NO:87 is the nucleotide sequence of the FBA promoter.

SEQ ID NO:88 is the nucleotide sequence of the ADH1 terminator.

SEQ ID NO:89 is the nucleotide sequence of the GPM promoter.

SEQ ID NOs:90 and 91 are primers for PCR of the SLT2 gene and flanking DNA.

DETAILED DESCRIPTION

The present invention relates to recombinant yeast cells that are engineered for production of butanol and that additionally are engineered to have increased activity of the cell wall integrity (CWI) pathway. The present yeast cells may have increased expression or activity of at least one protein involved in promoting activity of the CWI pathway including proteins that are CWI pathway receptors of external stimuli, proteins that are in the mitogen-activated protein kinase (MAPK) module of the CWI pathway, and proteins that are downstream targets of the MAPK module of the CWI pathway. These yeast cells have increased tolerance to butanol and may be used for production of butanol which is valuable as a fuel or fuel additive to reduce demand for fossil fuels.

The following abbreviations and definitions will be used for the interpretation of the specification and the claims.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the specification and the claims.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably within 5% of the reported numerical value The term "butanol" as used herein, refers to 1-butanol, 2-butanol, isobutanol, or mixtures thereof.

The terms "butanol tolerant yeast cell" and "tolerant" when used to describe a modified yeast cell of the invention, refers to a modified yeast that shows better growth in the presence of butanol than the parent strain from which it is derived.

The term "butanol biosynthetic pathway" refers to an enzyme pathway to produce 1-butanol, 2-butanol, or isobutanol.

The term "1-butanol biosynthetic pathway" refers to an enzyme pathway to produce 1-butanol from acetyl-coenzyme A (acetyl-CoA).

The term "2-butanol biosynthetic pathway" refers to an enzyme pathway to produce 2-butanol from pyruvate.

The term "isobutanol biosynthetic pathway" refers to an enzyme pathway to produce isobutanol from pyruvate.

The term "mitogen activated protein (MAP) kinase" refers to proteins with EC number EC 2.7.11.24, which are serine/threonine-specific protein kinases that respond to extracellular stimuli (mitogens) and regulate various cellular activities, such as gene expression, mitosis, differentiation, and cell survival/apoptosis.

The term "SLT2" refers to a gene encoding a type of MAP kinase that is a part of the mitogen-activated protein kinase module of the cell wall integrity pathway. SLT2p is the protein encoded by SLT2, which is an example of proteins classified as EC 2.7.11.24. Proteins with the same function as SLT2p encoded by SLT2 may be referred to in the art as being encoded by genes with other names including BYC2, MPK1, SLK2, MPKA, SPM1, MKC1, PMK1, and PIM1. The term SLT2p refers herein to any of these encoded proteins that function similarly to SLT2p in the mitogen-activated protein kinase module of the cell wall integrity pathway and that have sequence identity to an SLT2p amino acid sequence that is at least about 55%-60%, 60%-65%, 65%-70%, 70%-75%, 75%-80%, 80%-85%, 85%-90%, 90%-95%, or 95%-100%.

The term "acetyl-CoA acetyltransferase" refers to an enzyme that catalyzes the conversion of two molecules of acetyl-CoA to acetoacetyl-CoA and coenzyme A (CoA). Preferred acetyl-CoA acetyltransferases are acetyl-CoA acetyltransferases with substrate preferences (reaction in the forward direction) for a short chain acyl-CoA and acetyl-CoA and are classified as E.C. 2.3.1.9 [*Enzyme Nomenclature* 1992, Academic Press, San Diego]; although, enzymes with a broader substrate range (E.C. 2.3.1.16) will be functional as well. Acetyl-CoA acetyltransferases are available from a number of sources, for example, *Escherichia coli* (GenBank Nos: NP_416728, NC_000913; NCBI (National Center for Biotechnology Information) amino acid sequence, NCBI nucleotide sequence), *Clostridium acetobutylicum* (GenBank Nos: NP_349476.1 (SEQ ID NO:2), NC_003030; NP_149242 (SEQ ID NO:4), NC_001988), *Bacillus subtilis* (GenBank Nos: NP_390297, NC_000964), and *Saccharomyces cerevisiae* (GenBank Nos: NP_015297, NC_001148 (SEQ ID NO:39)).

The term "3-hydroxybutyryl-CoA dehydrogenase" refers to an enzyme that catalyzes the conversion of acetoacetyl-CoA to 3-hydroxybutyryl-CoA. 3-Hydroxybutyryl-CoA dehydrogenases may be reduced nicotinamide adenine dinucleotide (NADH)-dependent, with a substrate preference for (S)-3-hydroxybutyryl-CoA or (R)-3-hydroxybutyryl-CoA and are classified as E.C. 1.1.1.35 and E.C. 1.1.1.30, respectively. Additionally, 3-hydroxybutyryl-CoA dehydrogenases may be reduced nicotinamide adenine dinucleotide phosphate (NADPH)-dependent, with a substrate preference for (S)-3-hydroxybutyryl-CoA or (R)-3-hydroxybutyryl-CoA and are classified as E.C. 1.1.1.157 and E.C. 1.1.1.36, respectively. 3-Hydroxybutyryl-CoA dehydrogenases are available from a number of sources, for example, *C. acetobutylicum* (GenBank NOs: NP_349314 (SEQ ID NO:6), NC_003030), *B. subtilis* (GenBank NOs: AAB09614, U29084), *Ralstonia eutropha* (GenBank NOs: ZP_0017144, NZ_AADY01000001, *Alcaligenes eutrophus* (GenBank NOs: YP_294481, NC_007347), and *A. eutrophus* (GenBank NOs: P14697, J04987).

The term "crotonase" refers to an enzyme that catalyzes the conversion of 3-hydroxybutyryl-CoA to crotonyl-CoA and H₂O. Crotonases may have a substrate preference for (S)-3-hydroxybutyryl-CoA or (R)-3-hydroxybutyryl-CoA and are classified as E.C. 4.2.1.17 and E.C. 4.2.1.55, respectively. Crotonases are available from a number of sources, for example, *E. coli* (GenBank NOs: NP_415911 (SEQ ID NO:8), NC_000913), *C. acetobutylicum* (GenBank NOs: NP_349318, NC_003030), *B. subtilis* (GenBank NOs: CAB13705, Z99113), and *Aeromonas caviae* (GenBank NOs: BAA21816, D88825).

The term "butyryl-CoA dehydrogenase", also called trans-enoyl CoA reductase, refers to an enzyme that catalyzes the conversion of crotonyl-CoA to butyryl-CoA. Butyryl-CoA dehydrogenases may be NADH-dependent or NADPH-dependent and are classified as E.C. 1.3.1.44 and E.C. 1.3.1.38, respectively. Butyryl-CoA dehydrogenases are available from a number of sources, for example, *C. acetobutylicum* (GenBank NOs: NP_347102 (SEQ ID NO:10), NC_003030), *Euglena gracilis* (GenBank NOs: Q5EU90, AY741582), *Streptomyces collinus* (Gen Bank NOs: AAA92890, U37135), and *Streptomyces coelicolor* (GenBank NOs: CAA22721, AL939127).

The term "butyraldehyde dehydrogenase" refers to an enzyme that catalyzes the conversion of butyryl-CoA to butyraldehyde, using NADH or NADPH as cofactor. Butyraldehyde dehydrogenases with a preference for NADH are known as E.C. 1.2.1.57 and are available from, for example, *Clostridium beijerinckii* (GenBank NOs: AAD31841 (SEQ ID NO:12), AF157306) and *C. acetobutylicum* (GenBank NOs: NP_149325, NC_001988).

The term "1-butanol dehydrogenase" refers to an enzyme that catalyzes the conversion of butyraldehyde to 1-butanol. 1-butanol dehydrogenases are a subset of the broad family of alcohol dehydrogenases. 1-butanol dehydrogenase may be NADH- or NADPH-dependent. 1-butanol dehydrogenases are available from, for example, *C. acetobutylicum* (GenBank NOs: NP_149325, NC_001988; NP_349891 (SEQ ID NO:14), NC_003030; and NP_349892 (SEQ ID NO:16), NC_003030) and *E. coli* (GenBank NOs: NP_417484, NC_000913).

The term "acetolactate synthase", also known as "acetohydroxy acid synthase", refers to a polypeptide (or polypeptides) having an enzyme activity that catalyzes the conversion of two molecules of pyruvic acid to one molecule of alpha-acetolactate. Acetolactate synthase, known as EC 2.2.1.6 [formerly 4.1.3.18] (*Enzyme Nomenclature* 1992, Academic Press, San Diego) may be dependent on the cofactor thiamin pyrophosphate for its activity. Suitable acetolactate synthase enzymes are available from a number of sources, for example, *Bacillus subtilis* (GenBank Nos: AAA22222 NCBI (National Center for Biotechnology Information) amino acid sequence (SEQ ID NO:42), L04470 NCBI nucleotide sequence (SEQ ID NO:41)), *Klebsiella terrigena* (GenBank Nos: AAA25055, L04507), and *Klebsiella pneumoniae* (GenBank Nos: AAA25079 (SEQ ID NO:20), M73842 (SEQ ID NO:19).

The term "acetolactate decarboxylase" refers to a polypeptide (or polypeptides) having an enzyme activity that catalyzes the conversion of alpha-acetolactate to acetoin. Acetolactate decarboxylases are known as EC 4.1.1.5 and are available, for example, from *Bacillus subtilis* (GenBank Nos: AAA22223, L04470), *Klebsiella terrigena* (GenBank Nos: AAA25054, L04507) and *Klebsiella pneumoniae* (SEQ ID NO:18 (amino acid) SEQ ID NO:17 (nucleotide)).

The term "butanediol dehydrogenase" also known as "acetoin reductase" refers to a polypeptide (or polypeptides) having an enzyme activity that catalyzes the conversion of acetoin to 2,3-butanediol. Butanediol dehydrogenases are a subset of the broad family of alcohol dehydrogenases. Butanediol dehydrogenase enzymes may have specificity for production of R- or S-stereochemistry in the alcohol product. S-specific butanediol dehydrogenases are known as EC 1.1.1.76 and are available, for example, from *Klebsiella pneumoniae* (GenBank Nos: BBA13085 (SEQ ID NO:22), D86412. R-specific butanediol dehydrogenases are known as EC 1.1.1.4 and are available, for example, from *Bacillus cereus* (GenBank Nos. NP_830481, NC_004722; AAP07682, AE017000), and *Lactococcus lactis* (GenBank Nos. AAK04995, AE006323).

The term "butanediol dehydratase", also known as "diol dehydratase" or "propanediol dehydratase" refers to a polypeptide (or polypeptides) having an enzyme activity that catalyzes the conversion of 2,3-butanediol to 2-butanone, also known as methyl ethyl ketone (MEK). Butanediol dehydratase may utilize the cofactor adenosyl cobalamin. Adenosyl cobalamin-dependent enzymes are known as EC 4.2.1.28 and are available, for example, from Klebsiella oxytoca (GenBank Nos: BAA08099 (alpha subunit) (SEQ ID NO:24), BAA08100 (beta subunit) (SEQ ID NO:26), and BBA08101 (gamma subunit) (SEQ ID NO:28), (Note all three subunits are required for activity), D45071).

The term "2-butanol dehydrogenase" refers to a polypeptide (or polypeptides) having an enzyme activity that catalyzes the conversion of 2-butanone to 2-butanol. 2-butanol dehydrogenases are a subset of the broad family of alcohol dehydrogenases. 2-butanol dehydrogenase may be NADH- or NADPH-dependent. The NADH-dependent enzymes are known as EC 1.1.1.1 and are available, for example, from *Rhodococcus ruber* (GenBank Nos: CAD36475 (SEQ ID NO:30), AJ491307 (SEQ ID NO:29)). The NADPH-dependent enzymes are known as EC 1.1.1.2 and are available, for example, from *Pyrococcus furiosus* (GenBank Nos: AAC25556, AF013169).

The term "acetohydroxy acid isomeroreductase" or "acetohydroxy acid reductoisomerase" refers to an enzyme that catalyzes the conversion of acetolactate to 2,3-dihydroxyisovalerate using NADPH (reduced nicotinamide adenine dinucleotide phosphate) as an electron donor. Preferred acetohydroxy acid isomeroreductases are known by the EC number 1.1.1.86 and sequences are available from a vast array of microorganisms, including, but not limited to, *Escherichia coli* (GenBank Nos: NP_418222 (SEQ ID NO:32), NC_000913 (SEQ ID NO:31)), *Saccharomyces cerevisiae* (GenBank Nos: NP_013459 (SEQ ID NO:44), NC_001144 (SEQ ID NO:43)), *Methanococcus maripaludis* (GenBank Nos: CAF30210, BX957220), and *Bacillus subtilis* (GenBank Nos: CAB14789 (SEQ ID NO:46), Z99118 (SEQ ID NO:45)).

The term "acetohydroxy acid dehydratase" or "dihydroxy acid dehydratase" refers to an enzyme that catalyzes the conversion of 2,3-dihydroxyisovalerate to α-ketoisovalerate. Preferred acetohydroxy acid dehydratases are known by the EC number 4.2.1.9. These enzymes are available from a vast array of microorganisms, including, but not limited to, *E. coli* (GenBank Nos: YP_026248 (SEQ ID NO:34), NC_000913 (SEQ ID NO:33)), *S. cerevisiae* (GenBank Nos: NP_012550 (SEQ ID NO:48), NC_001142 (SEQ ID NO:47)), *M. maripaludis* (GenBank Nos: CAF29874, BX957219), and *B. subtilis* (GenBank Nos: CAB14105, Z99115).

The term "branched-chain α-keto acid decarboxylase" refers to an enzyme that catalyzes the conversion of α-ketoisovalerate to isobutyraldehyde and $CO_2$. Preferred branched-chain α-keto acid decarboxylases are known by the EC number 4.1.1.72 and are available from a number of sources, including, but not limited to, *Lactococcus lactis* (GenBank Nos: AAS49166, AY548760; CAG34226 (SEQ ID NO:36), AJ746364, *Salmonella typhimurium* (GenBank Nos: NP_461346, NC_003197), and *Clostridium acetobutylicum* (GenBank Nos: NP_149189, NC_001988).

The term "branched-chain alcohol dehydrogenase" refers to an enzyme that catalyzes the conversion of isobutyraldehyde to isobutanol. Preferred branched-chain alcohol dehydrogenases are known by the EC number 1.1.1.265, but may also be classified under other alcohol dehydrogenases (specifically, EC 1.1.1.1 or 1.1.1.2). These enzymes utilize NADH (reduced nicotinamide adenine dinucleotide) and/or NADPH as electron donor and are available from a number of sources, including, but not limited to, *S. cerevisiae* (GenBank Nos: NP_010656, NC_001136; NP_014051, NC_001145), *E. coli* (GenBank Nos: NP_417484 (SEQ ID NO:38), NC_000913 (SEQ ID NO:37)), and *C. acetobutylicum* (GenBank Nos: NP_349892, NC_003030).

The term "gene" refers to a nucleic acid fragment that is capable of being expressed as a specific protein, optionally including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "heterologous" or "foreign" gene refers to a gene not normally found in the host organism, but that is introduced into the host organism by gene transfer. Foreign or heterologous genes can comprise native genes inserted into a non-native organism, or chimeric genes. "Heterologous gene" includes a native coding region, or portion thereof, that is reintroduced into the source organism in a form that is different from the corresponding native gene. For example, a heterologous gene may include a native coding region that is a portion of a chimeric gene including non-native regulatory regions that is reintroduced into the native host. A "transgene" is a gene that has been introduced into the genome by a transformation procedure.

As used herein the term "coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

The term "promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of effecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

As used herein the term "transformation" refers to the transfer of a nucleic acid fragment into a host organism, resulting in genetically stable inheritance. Host organisms containing the transformed nucleic acid fragments are referred to as "transgenic" or "recombinant" or "transformed" organisms.

The terms "plasmid" and "vector" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation vector" refers to a specific vector containing a foreign gene and having elements in addition to the foreign gene that facilitates transformation of a particular host cell.

As used herein the term "codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.,* 215: 403-410 (1993)). In general, a sequence of ten or more contiguous amino acids or thirty or more nucleotides is necessary in order to identify putatively a polypeptide or nucleic acid sequence as homologous to a known protein or gene. Moreover, with respect to nucleotide sequences, gene-specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence.

As used herein, "substantially similar" enzymes will refer to enzymes belonging to a family of proteins in the art known to share similar structures and function. It is well within the skill of one in the art to identify substantially similar proteins given a known structure. Typical methods to identify substantially similar structures will rely upon known sequence information (nucleotide sequence and/or amino acid sequences) and may include PCR amplification, nucleic acid hybridization, and/or sequence identity/similarity analysis (e.g., sequence alignments between partial and/or complete sequences and/or known functional motifs associated with the desired activity).

A nucleic acid molecule is "hybridizable" to another nucleic acid molecule, such as a cDNA, genomic DNA, or RNA molecule, when a single-stranded form of the nucleic acid molecule can anneal to the other nucleic acid molecule under the appropriate conditions of temperature and solution ionic strength. Given the nucleic acid sequences described herein, one of skill in the art can identify substantially similar nucleic acid fragments that may encode proteins having similar activity. Hybridization and washing conditions are well known and exemplified in Sambrook, J., Fritsch, E. F. and Maniatis, T. *Molecular Cloning: A Laboratory Manual,* 3rd ed., Cold Spring Harbor Laboratory: Cold Spring Harbor, N.Y. (2001), particularly Chapter 11 and Table 11.1 therein. The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washes with 2×SSC, 0.1% SDS at 65° C. followed by 0.1×SSC, 0.1% SDS at 65° C., for example.

In one aspect, suitable nucleic acid fragments encode polypeptides that are at least about 70% identical to the amino acid sequences reported herein. In another aspect, the nucleic acid fragments encode amino acid sequences that are about 85-90% identical to the amino acid sequences reported herein. In a further aspect, the nucleic acid fragments encode amino acid sequences that are at least about 90-100% identical to the amino acid sequences reported herein. Suitable nucleic acid fragments not only have the above homologies but typically encode a polypeptide having at least about 50 amino acids, preferably at least about 100 amino acids, more preferably at least about 150 amino acids, still more preferably at least about 200 amino acids, and most preferably at least about 250 amino acids.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences is performed using the Clustal method of alignment (Higgins and Sharp, *CABIOS.* 5:151-153 (1989)) with default parameters (GAP PENALTY=10, GAP LENGTH PENALTY=10), unless otherwise specified. Default parameters for pairwise alignments using the Clustal method are: KTUPLE 1, GAP PENALTY=3, WINDOW=5 and DIAGONALS SAVED=5.

Suitable nucleic acid fragments (isolated polynucleotides of the present invention) encode polypeptides that are at least about 70% identical, preferably at least about 75% identical, and more preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

The term "homology" refers to the relationship among sequences whereby there is some extent of likeness, typically due to descent from a common ancestral sequence. Homologous sequences can share homology based on genic, structural, functional and/or behavioral properties. The term "ortholog" or "orthologous sequences" refers herein to a relationship where sequence divergence follows speciation (i.e., homologous sequences in different species arose from a common ancestral gene during speciation). In contrast, the term "paralogous" refers to homologous sequences within a single species that arose by gene duplication. One skilled in the art will be familiar with techniques required to identify homologous, orthologous and paralogous sequences.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.,* 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, *Comput. Methods Genome Res.,* [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein, "default values" will mean any set of values or parameters (as set by the software manufacturer) which originally load with the software when first initialized Standard recombinant DNA and molecular cloning techniques used here are well known in the art and are described by Sambrook, J., Fritsch, E. F. and Maniatis, T. *Molecular Cloning: A Laboratory Manual,* $2^{nd}$ ed.; Cold Spring Harbor Laboratory: Cold Spring Harbor, N.Y., 1989 (hereinafter "Maniatis"); and by Silhavy, T. J., Bennan, M. L. and Enquist, L. W. *Experiments with Gene Fusions*; Cold Spring Harbor Laboratory: Cold Spring Harbor, N.Y., 1984; and by Ausubel, F. M. et al., In *Current Protocols in Molecular Biology*, published by Greene Publishing and Wiley-Interscience, 1987.

"Fermentable sugars" refers to a sugar content primarily comprising monosaccharides and some disaccharides that can be used as the carbon source by microorganisms in a fermentation process to produce a target product. Sugars may from from any source, including cellulosic, hemicellulosic or ligcellulosic biomass.

Screening for Butanol Tolerance: Involvement of CWI Pathway

The invention relates to the discovery that increasing activity of the CWI pathway has the effect of increasing tolerance of yeast cells to butanol. The discovery came from screening studies to identify yeast cells containing random fragments of yeast genomic DNA that had increased tolerance to butanol. In these studies, yeast containing a library of random genomic DNA fragments were grown in the presence of isobutanol to identify clones with improved growth relative to controls. In one clone with increased tolerance to butanol the random genomic DNA fragment was found to include the STL2 gene. In further experiments herein, deletion of the SLT2 gene was found to increase sensitivity of yeast to butanol while overexpression of the SLT2 coding region was found to increase tolerance of yeast to butanol, A yeast strain which overexpressed the SLT2p product of the SLT2 coding region had a 29% improvement in growth yield over the parental strain in 1% (w/v) isobutanol (Example 3 herein). In some embodiments, yeast cells provided herein have at least about a 20% or at least about a 25% improvement in growth yield.

The SLT2p product of the SLT2 gene plays an important role in the CWI pathway. SLT2 encodes a protein kinase that phosphorylates serine and threonine residues of its target proteins. SLT2 is a mitogen activated protein kinase (MAPK) that responds to environmental signals and is involved in regulating the maintenance of cell wall integrity. Specifically, SLT2p is the MAPK of the MAPK module of the CWI pathway. Thus increase in SLT2p expression increases activity of the CWI pathway.

Increase in CWI Pathway Activity by Directly Engineering SLT2p Expression

In the present engineered yeast cell any SLT2p may be expressed in increased amount above the amount found in the cell without SLT2p engineering to provide increased butanol tolerance. In the present yeast cell the endogenous SLT2p of the target yeast cell may be overexpressed, or a heterologous SLT2p may be expressed in the cell to provide increased activity. Examples of SLT2p that may be expressed include those from *Saccharomyces cerevisiae* (coding region SEQ ID NO:49; protein SEQ ID NO:50), *Candida glabrata* (coding region SEQ ID NO:51; protein SEQ ID NO:52), *Candida albicans* (coding region SEQ ID NO:53; protein SEQ ID NO:54), *Yarrowia lipolytica* (coding region SEQ ID NO:55; protein SEQ ID NO:56), *Pichia stipitis* (coding region SEQ ID NO:57; protein SEQ ID NO:58), *Debaryomyces hansenii* (coding region SEQ ID NO:59; protein SEQ ID NO:60), *Kluyveromyces lactis* (coding region SEQ ID NO:61; protein SEQ ID NO:62), *Ashbya gossypii* (coding region SEQ ID NO:63; protein SEQ ID NO:64), *Aspegillus fumigatus* (coding region SEQ ID NO:65; protein SEQ ID NO:66), *Aspergillus terreus* (coding region SEQ ID NO:67; protein SEQ ID NO:68), *Coprinopsis cinerea* (coding region SEQ ID NO:69; protein SEQ ID NO:70), *Schizosaccharomyces pombe* (coding region SEQ ID NO:71; protein SEQ ID NO:72), and *Ustilago maydis* (coding region SEQ ID NO:73; protein SEQ ID NO:74).

Some proteins that can be recognized as performing the same function as SLT2p, that have high sequence identity to SLT2p, may have a different name in the art. Other names for the SLT2 gene include BYC2, MPK1, SLK2, MPKA, SPM1, MKC1, PMK1, and PIM1. Although there is this variation in naming, a protein may be readily recognized as an SLT2p homolog by its sequence and by its activity as a MAP kinase in the MAP kinase module of the cell wall integrity pathway.

Because the sequences of SLT2 coding regions and the encoded proteins are known, as exemplified in the SEQ ID NOs listed above and given in Table 4, suitable SLT2ps may be readily identified by one skilled in the art on the basis of sequence similarity using bioinformatics approaches. Typically BLAST (described above) searching of publicly available databases with known SLT2p amino acid sequences, such as those provided herein, is used to identify SLT2ps, and their encoding sequences, that may be used in the present strains. These proteins may have at least about 55%-60%, 60%-65%, 65%-70%, 70%-75%, 75%-80%, 80-85%, 85%-90%, 90%-95% or 95%-99% sequence identity to any of the SLT2ps of SEQ ID NOS:50, 52, 54, 56, 58, 60, 62, 64, 66, 68, 70, 72, or 74 while having SLT2p activity. Identities are based on the Clustal W method of alignment using the default parameters of GAP PENALTY=10, GAP LENGTH PENALTY=0.1, and Gonnet 250 series of protein weight matrix.

In addition to using protein or coding region sequence and bioinformatics methods to identify additional SLT2ps, the sequences described herein or those recited in the art may be used to experimentally identify other homologs in nature. For example each of the of SLT2 encoding nucleic acid fragments described herein may be used to isolate genes encoding homologous proteins. Isolation of homologous genes using sequence-dependent protocols is well known in the art. Examples of sequence-dependent protocols include, but are not limited to: 1.) methods of nucleic acid hybridization; 2.) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., *Proc. Acad. Sci. USA* 82:1074 (1985); or strand displacement amplification (SDA), Walker, et al., *Proc. Natl. Acad. Sci. U.S.A.*, 89:392 (1992)]; and 3.) methods of library construction and screening by complementation.

For example, genes encoding similar proteins or polypeptides to the SLT2p encoding genes described herein could be isolated directly by using all or a portion of the instant nucleic acid fragments as DNA hybridization probes to screen libraries from any desired organism using methodology well known to those skilled in the art. Specific oligonucleotide probes based upon the disclosed nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments by hybridization under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotides as specific hybridization probes in the Diagnosis of Genetic Disorders", in *Human Genetic Diseases: A Practical Approach*, K. E. Davis Ed., (1986) pp 33-50, IRL: Herndon, Va.; and Rychlik, W., In *Methods in Molecular Biology*, White, B. A. Ed., (1993) Vol. 15, pp 31-39, PCR Protocols: Current Methods and Applications. Humania: Totowa, N.J.).

Generally two short segments of the described sequences may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the described nucleic acid fragments, and the sequence of the other primer takes advantage of the presence of the polyadenylic acid tracts to the 3' end of the mRNA precursor encoding microbial genes.

Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (e.g., BRL, Gaithersburg, Md.), specific 3' or 5' cDNA fragments can be isolated (Ohara et al., *PNAS USA* 86:5673 (1989); Loh et al., *Science* 243:217 (1989)).

Alternatively, the described SLT2p encoding sequences may be employed as hybridization reagents for the identification of homologs. The basic components of a nucleic acid hybridization test include a probe, a sample suspected of containing the gene or gene fragment of interest, and a specific hybridization method. Probes are typically single-stranded nucleic acid sequences that are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res.* 19:5143-5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide and cesium trifluoroacetate, among others. Typically, the chaotropic agent will be present at a final concentration of about 3 M. If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal) and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Expression of SLT2p is achieved by transforming with a gene comprising a sequence encoding an SLT2p. When using a heterologous coding region, the sequence may be codon-optimized for maximal expression in the target yeast host cell, as well known to one skilled in the art. Methods for gene expression in yeasts are known in the art (see for example *Methods in Enzymology*, Volume 194, *Guide to Yeast Genetics and Molecular and Cell Biology* (Part A, 2004, Christine Guthrie and Gerald R. Fink (Eds.), Elsevier Academic Press, San Diego, Calif.). Expression of genes in yeast typically requires a promoter, operably linked to a coding region of interest, and a transcriptional terminator. A number of yeast promoters can be used in constructing expression cassettes for genes encoding an SLT2p, including, but not limited to constitutive promoters FBA, GPD, ADH1, TEF, and GPM, and the inducible promoters GAL1, GAL10, and CUP1. Suitable transcriptional terminators include, but are not limited to FBAt, GPDt, GPMt, ERG10t, GAL1t, CYC1, and ADH1.

Suitable promoters, transcriptional terminators, and SLT2 coding regions may be cloned into *E. coli*-yeast shuttle vectors, and transformed into yeast cells. These vectors allow propagation in both *E. coli* and yeast strains. Typically the vector contains a selectable marker and sequences allowing autonomous replication or chromosomal integration in the desired host. Typically used plasmids in yeast are shuttle vectors pRS423, pRS424, pRS425, and pRS426 (American Type Culture Collection, Rockville, Md.), which contain an *E. coli* replication origin (e.g., pMB1), a yeast 2μ origin of replication, and a marker for nutritional selection. The selection markers for these four vectors are His3 (vector pRS423), Trp1 (vector pRS424), Leu2 (vector pRS425) and Ura3 (vector pRS426). Construction of expression vectors with a chimeric gene encoding an SLT2p may be performed by either standard molecular cloning techniques in *E. coli* or by the gap repair recombination method in yeast.

The gap repair cloning approach takes advantage of the highly efficient homologous recombination in yeast. Typically, a yeast vector DNA is digested (e.g., in its multiple cloning site) to create a "gap" in its sequence. A number of insert DNAs of interest are generated that contain a ≥21 bp sequence at both the 5' and the 3' ends that sequentially overlap with each other, and with the 5' and 3' terminus of the vector DNA. For example, to construct a yeast expression vector for "Gene X", a yeast promoter and a yeast terminator are selected for the expression cassette. The promoter and terminator are amplified from the yeast genomic DNA, and Gene X is either PCR amplified from its source organism or obtained from a cloning vector comprising Gene X sequence. There is at least a 21 bp overlapping sequence between the 5' end of the linearized vector and the promoter sequence, between the promoter and Gene X, between Gene X and the terminator sequence, and between the terminator and the 3' end of the linearized vector. The "gapped" vector and the insert DNAs are then co-transformed into a yeast strain and plated on the medium containing the appropriate compound mixtures that allow complementation of the nutritional selection markers on the plasmids. The presence of correct insert combinations can be confirmed by PCR mapping using plasmid DNA prepared from the selected cells. The plasmid DNA isolated from yeast (usually low in concentration) can then be transformed into an *E. coli* strain, e.g. TOP10, followed by mini preps and restriction mapping to further verify the plasmid construct. Finally the construct can be verified by sequence analysis.

Like the gap repair technique, integration into the yeast genome also takes advantage of the homologous recombination system in yeast. Typically, a cassette containing a coding region plus control elements (promoter and terminator) and auxotrophic marker is PCR-amplified with a high-fidelity DNA polymerase using primers that hybridize to the cassette and contain 40-70 base pairs of sequence homology to the regions 5' and 3' of the genomic area where insertion is desired. The PCR product is then transformed into yeast and plated on medium containing the appropriate compound mixtures that allow selection for the integrated auxotrophic marker. For example, to integrate "Gene X" into chromosomal location "Y", the promoter-coding regionX-terminator construct is PCR amplified from a plasmid DNA construct and joined to an autotrophic marker (such as URA3) by either SOE PCR or by common restriction digests and cloning. The full cassette, containing the promoter-coding regionX-terminator-URA3 region, is PCR amplified with primer sequences that contain 40-70 by of homology to the regions 5' and 3' of location "Y" on the yeast chromosome. The PCR product is transformed into yeast and selected on growth media lacking uracil. Transformants can be verified either by colony PCR or by direct sequencing of chromosomal DNA. In addition the endogenous promoter of a gene may be replaced with a stronger promoter to increase expression by homologous recombination.

Additional Engineering to Increase CWI Pathway Activity

Increased expression of other genes of the CWI pathway may be engineered to provide yeast cells of the present invention that have increased tolerance to butanol. Target genes and their encoded proteins for increased expression in the present yeast cells include any gene whose increased expression causes increased activity of the CWI pathway. Target genes may include those that increase activity of SLT2p as well as any gene whose activity is increased by increased SLT2p activity. Genes of the CWI pathway are known in the art. For example, genes of the CWI pathway are disclosed in Kim et al. (Mol. Cell. Biol. (2008) 281:2579-89), Kim et al. (Yeast (2007) 241: 335-42), Jimenez-Sanchez and Molina (J. Biol. Chem. (2007) 282: 31174-85), Levin, D. E. (Microbiol. Mol. Biol. Rev. (2005): 262-291), Chen and Thorner (Biochimica et Biophysica Acta (2007) 1773: 1311-1340), all herein incorporated by reference. For example, genes that may be targets are in the MAPK module of the CWI pathway which includes SLT2. These genes include the MAPK kinases (MAPKK) MKK1 and MKK2, and the MAPKK kinase (MAPKKK) BCK1. Another target gene is PKC1, whose product PKC1p activates the MAPK module of the CWI pathway by phosphorylating BCK1p. Other target proteins activate PKC1p and are the products of the genes WSC1, WSC2, WSC3, MID2, MTL1, HOR2, YPT7, ROM2, BEM2, ABC1 and RHO1. In addition proteins in TOR2 and PKH1/PKH2 branches of the CWI pathway network activate PKC1p and may be targets in the present cells. Target genes for increased CWI pathway activity that are downstream of the MAPK module include EPT1, STB5, YDJ1, SSD1, CNA1, KRE11, EXG1, EXG2, DGK1, HCR1, LOC1, PDR2, PDR8, SWI4, SWI6, and RLM1. The SKN7 product is downstream of the RHO1 product and is also a target gene for increased CWI pathway activity.

The activity of any of the proteins encoded by these target genes may be increased by overexpressing the endogenous encoding sequence in a yeast cell or by expressing a heterologous sequence encoding the protein. Expression of any of these proteins may be accomplished as described above for SLT2p. The coding sequences and encoded proteins that may be used in the present cells may be readily identified in publicly available databases by one skilled in the art using the gene names and functions listed above. Any coding region to be expressed may be codon optimized for the host cell to be engineered, as well known to one skilled in the art.

Host Yeast Cells

The target genes and proteins that are engineered to provide an increase in CWI pathway activity to confer butanol tolerance may be engineered in any yeast cell that is additionally engineered for production of butanol. Suitable yeasts include, but are not limited to, *Saccharomyces, Schizosaccharomyces, Hansenula, Candida, Kluyveromyces, Yarrowia, Issatchenkia,* and *Pichia*. Suitable strains include, but are not limited to, *Saccharomyces cerevisiae Schizosaccharomyces pombe, Kluyveromyces lactis, Kluyveromyces thermotolerans, Candida glabrata, Candida albicans, Pichia stipitis* and *Yarrowia lipolytica.*

Butanol Biosynthetic Pathway

In the present invention, a genetic modification conferring increased butanol tolerance, as described above, is engineered in a yeast cell that is engineered to express a butanol biosynthetic pathway. Either genetic modification may take place prior to the other. The butanol biosynthetic pathway may be a 1-butanol, 2-butanol, or isobutanol biosynthetic pathway.

Suitable biosynthetic pathways are known in the art, and certain suitable pathways are described herein. In some embodiments, the butanol biosynthetic pathway comprises at least one gene that is heterologous to the yeast cell. In some embodiments, genes encoding proteins which catalyze each substrate to product conversion of the butanol biosynthetic pathway are heterologous to the yeast cell. In some embodiments, the butanol biosynthetic pathway comprises more than one gene that is heterologous to the yeast cell. In some embodiments, genes encoding proteins which catalyze each substrate to product conversion of the butanol biosynthetic pathway are heterologous to the yeast cell. In some embodiments, the yeast cell comprises heterologous genes encoding the proteins for each substrate to product conversion of a butanol biosynthetic pathway.

Likewise, certain suitable proteins having the ability to catalyze the indicated substrate to product conversions are described herein and other suitable proteins are described in the art. For example, US Published Patent Application Nos. US20080261230 and US20090163376, incorporated herein by reference, describe acetohydroxy acid isomeroreductases; US Patent Application No. 12/569,636, incorporated by reference, describes suitable dihydroxyacid dehydratases; a suitable alcohol dehydrogenase is described in US Published Patent Application US20090269823, incorporated herein by reference.

1-Butanol Biosynthetic Pathway

A suitable biosynthetic pathway for the production of 1-butanol that may be used is described by Donaldson et al. in U.S. Patent Application Publication No. US20080182308A1, incorporated herein by reference. This biosynthetic pathway comprises the following substrate to product conversions:

a) acetyl-CoA to acetoacetyl-CoA, as catalyzed for example by acetyl-CoA acetyltransferase with protein sequence such as SEQ ID NO:2, 4 or 40 (which may be encoded, for example, by the genes given as SEQ ID NO:1, 3 or 39);
b) acetoacetyl-CoA to 3-hydroxybutyryl-CoA, as catalyzed for example by 3-hydroxybutyryl-CoA dehydrogenase with protein sequence such as SEQ ID NO:6 (which may be encoded, for example, by the gene given as SEQ ID NO:5);
c) 3-hydroxybutyryl-CoA to crotonyl-CoA, as catalyzed for example by crotonase with protein sequence such as SEQ ID NO:8 (which may be encoded, for example, by the gene given as SEQ ID NO:7);
d) crotonyl-CoA to butyryl-CoA, as catalyzed for example by butyryl-CoA dehydrogenase with protein sequence such as SEQ ID NO:10 (which may be encoded, for example, by the gene given as SEQ ID NO:9);
e) butyryl-CoA to butyraldehyde, as catalyzed for example by butyraldehyde dehydrogenase with protein sequence such as SEQ ID NO:12 (which may be encoded, for example, by the gene given as SEQ ID NO:11); and
f) butyraldehyde to 1-butanol, as catalyzed for example by 1-butanol dehydrogenase with protein sequence such as SEQ ID NO:14 or 16 (which may be encoded, for example, by the genes given as SEQ ID NO:13 or 15).

The pathway requires no ATP and generates $NAD^+$ and/or $NADP^+$, thus, it balances with the central, metabolic routes that generate acetyl-CoA.

Other suitable biosynthetic pathways for the production of 1-butanol will be apparent to those of skill in the art. It will be appreciated that yeast cells may be engineered to express proteins that retain the ability to catalyze the indicated substrate to product conversion but have less than 100% sequence identity to the protein sequences provided herein. In one embodiment, yeast cells may be engineered to express a 1-butanol biosynthetic pathway comprising a sequence that has at least about 70%-75%, 75%-80%, 80-85%, 85%-90%, 90%-95% or 95%-99% sequence identity to a 1-butanol pathway protein provided herein.

2-Butanol Biosynthetic Pathway

Suitable biosynthetic pathways for the production of 2-butanol that may be used are described by Donaldson et al. in U.S. Patent Application Publication Nos. US20070259410A1 and US 20070292927A1, each incorporated herein by reference. One 2-butanol biosynthetic pathway comprises the following substrate to product conversions:
a) pyruvate to alpha-acetolactate, as catalyzed for example by acetolactate synthase with protein sequence such as SEQ ID NO:20 (which may be encoded, for example, by the gene given as SEQ ID NO:19);
b) alpha-acetolactate to acetoin, as catalyzed for example by acetolactate decarboxylase with protein sequence such as SEQ ID NO:18 (which may be encoded, for example, by the gene given as SEQ ID NO:17);
c) acetoin to 2,3-butanediol, as catalyzed for example by butanediol dehydrogenase with protein sequence such as SEQ ID NO:22 (which may be encoded, for example, by the gene given as SEQ ID NO:21);
d) 2,3-butanediol to 2-butanone, catalyzed for example by butanediol dehydratase with protein sequence such as SEQ ID NO:24, 26, or 28 (which may be encoded, for example, by genes given as SEQ ID NO:23, 25, or 27); and
e) 2-butanone to 2-butanol, as catalyzed for example by 2-butanol dehydrogenase with protein sequence such as SEQ ID NO:30 (which may be encoded, for example, by the gene given as SEQ ID NO:29).

Other suitable biosynthetic pathways for the production of 2-butanol will be apparent to those of skill in the art. It will be appreciated that yeast cells may be engineered to express proteins that retain the ability to catalyze the indicated substrate to product conversion but have less than 100% sequence identity to the protein sequences provided herein. In one embodiment, yeast cells may be engineered to express a 2-butanol biosynthetic pathway comprising a sequence that has at least about 70%-75%, 75%-80%, 80-85%, 85%-90%, 90%-95% or 95%-99% sequence identity to a 2-butanol pathway protein provided herein.

Isobutanol Biosynthetic Pathway

Suitable biosynthetic pathways for the production of isobutanol that may be used are described by Maggio-Hall et al. in U.S. Patent Application Publication No. US20070092957 A1, incorporated herein by reference. One isobutanol biosynthetic pathway comprises the following substrate to product conversions:
a) pyruvate to acetolactate, as catalyzed for example by acetolactate synthase with protein sequence such as SEQ ID NO:20 or 42 (which may be encoded, for example, by genes given as SEQ ID NO:19 or 41);
b) acetolactate to 2,3-dihydroxyisovalerate, as catalyzed for example by acetohydroxy acid isomeroreductase with protein sequence such as SEQ ID NO:32, 44 or 46 (which may be encoded, for example, by genes given as SEQ ID NO:31, 43 or 45);
c) 2,3-dihydroxyisovalerate to α-ketoisovalerate, as catalyzed for example by acetohydroxy acid dehydratase with protein sequence such as SEQ ID NO:34 (which may be encoded, for example, by the gene given as SEQ ID NO:33); or dihydroxyacid dehydratase with protein sequence such as SEQ ID NO:48 (which may be encoded, for example, by the gene given as SEQ ID NO:47);
d) α-ketoisovalerate to isobutyraldehyde, as catalyzed for example by a branched-chain keto acid decarboxylase with protein sequence such as SEQ ID NO:36 (which may be encoded, for example, by the gene given as SEQ ID NO:35); and
e) isobutyraldehyde to isobutanol, as catalyzed for example by a branched-chain alcohol dehydrogenase with protein sequence such as SEQ ID NO:38 (which may be encoded, for example, by the gene given as SEQ ID NO:37).

Other suitable biosynthetic pathways for the production of isobutanol will be apparent to those of skill in the art. It will be appreciated that yeast cells may be engineered to express proteins that retain the ability to catalyze the indicated substrate to product conversion but have less than 100% sequence identity to the protein sequences provided herein. In one embodiment, yeast cells may be engineered to express an isobutanol biosynthetic pathway comprising a sequence that has at least about 70%-75%, 75%-80%, 80-85%, 85%-90%, 90%-95% or 95%-99% sequence identity to an isobutanol pathway protein provided herein.

Construction of Yeast Strains for Butanol Production

Any yeast strain that is genetically modified for butanol tolerance as described herein is additionally genetically modified (before or after modification to tolerance) to incorporate a butanol biosynthetic pathway by methods well known to one skilled in the art. Genes encoding the enzyme activities described above, or homologs that may be identified and obtained by commonly used methods, such as those described above, that are well known to one skilled in the art, are introduced into a yeast host. Representative coding and amino acid sequences for pathway enzymes that may be used are given in Tables 1, 2, and 3, with SEQ ID NOs:1-48.

Methods for gene expression in yeasts that may be used for butanol pathway genes are described above for expression of SLT2.

Fermentation Media

Fermentation media in the present invention must contain suitable carbon substrates. Suitable substrates may include but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally the carbon substrate may also be one-carbon substrates such as carbon dioxide, or methanol for which metabolic conversion into key biochemical intermediates has been demonstrated. In addition to one and two carbon substrates methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth C1 Compd.*, [Int. Symp.], 7th (1993), 415-32. Editor(s): Murrell, J. Collin; Kelly, Don P. Publisher: Intercept, Andover, UK). Similarly, various species of *Candida* will metabolize alanine or oleic acid (Sulter et al., *Arch. Microbiol.* 153:485-489 (1990)). Hence it is contemplated that the source of carbon utilized in the present invention may encompass a wide variety of carbon containing substrates and will only be limited by the choice of organism.

Although it is contemplated that all of the above mentioned carbon substrates and mixtures thereof are suitable in the present invention, preferred carbon substrates are glucose, fructose, and sucrose.

In addition to an appropriate carbon source, fermentation media must contain suitable minerals, salts, cofactors, buffers and other components, known to those skilled in the art, suitable for the growth of the cultures and promotion of the enzymatic pathway necessary for butanol production.

Culture Conditions

Typically cells are grown at a temperature in the range of about 20° C. to about 37° C. in an appropriate medium. Suitable growth media in the present invention are common commercially prepared media such as broth that includes yeast nitrogen base, ammonium sulfate, and dextrose as the carbon/energy source) or YPD Medium, a blend of peptone, yeast extract, and dextrose in optimal proportions for growing most *Saccharomyces cerevisiae* strains. Other defined or synthetic growth media may also be used and the appropriate medium for growth of the particular microorganism will be known by one skilled in the art of microbiology or fermentation science.

Suitable pH ranges for the fermentation are between pH 3.0 to pH 7.5, where pH 4.5.0 to pH 6.5 is preferred as the initial condition.

Fermentations may be performed under aerobic or anaerobic conditions, where anaerobic or microaerobic conditions are preferred.

The amount of butanol produced in the fermentation medium can be determined using a number of methods known in the art, for example, high performance liquid chromatography (HPLC) or gas chromatography (GC).

Industrial Batch and Continuous Fermentations

The present process may employ a batch method of fermentation. A classical batch fermentation is a closed system where the composition of the medium is set at the beginning of the fermentation and not subject to artificial alterations during the fermentation. Thus, at the beginning of the fermentation the medium is inoculated with the desired organism or organisms, and fermentation is permitted to occur without adding anything to the system. Typically, however, a "batch" fermentation is batch with respect to the addition of carbon source and attempts are often made at controlling factors such as pH and oxygen concentration. In batch systems the metabolite and biomass compositions of the system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch system. Fed-Batch fermentation processes are also suitable in the present invention and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as CO2. Batch and Fed-Batch fermentations are common and well known in the art and examples may be found in Thomas D. Brock in *Biotechnology: A Textbook of Industrial Microbiology*, Second Edition (1989) Sinauer Associates, Inc., Sunderland, Mass., or Deshpande, Mukund V., *Appl. Biochem. Biotechnol.*, 36:227, (1992), herein incorporated by reference.

Although the present invention is performed in batch mode it is contemplated that the method would be adaptable to continuous fermentation methods. Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to the medium being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

It is contemplated that the present invention may be practiced using either batch, fed-batch or continuous processes and that any known mode of fermentation would be suitable. Additionally, it is contemplated that cells may be immobilized on a substrate as whole cell catalysts and subjected to fermentation conditions for 1-butanol production.

Methods for Butanol Isolation from the Fermentation Medium

The bioproduced butanol may be isolated from the fermentation medium using methods known in the art. For example, solids may be removed from the fermentation medium by centrifugation, filtration, decantation, or the like. Then, the butanol may be isolated from the fermentation medium, which has been treated to remove solids as described above, using methods such as distillation, liquid-liquid extraction, or membrane-based separation. Because butanol forms a low boiling point, azeotropic mixture with water, distillation can only be used to separate the mixture up to its azeotropic composition. Distillation may be used in combination with another separation method to obtain separation around the azeotrope. Methods that may be used in combination with distillation to isolate and purify butanol include, but are not limited to, decantation, liquid-liquid extraction, adsorption, and membrane-based techniques. Additionally, butanol may be isolated using azeotropic distillation using an entrainer (see for example Doherty and Malone, *Conceptual Design of Distillation Systems*, McGraw Hill, New York, 2001).

The butanol-water mixture forms a heterogeneous azeotrope so that distillation may be used in combination with decantation to isolate and purify the butanol. In this method, the butanol containing fermentation broth is distilled to near the azeotropic composition. Then, the azeotropic mixture is condensed, and the butanol is separated from the fermentation medium by decantation. The decanted aqueous phase may be returned to the first distillation column as reflux. The butanol-rich decanted organic phase may be further purified by distillation in a second distillation column.

The butanol may also be isolated from the fermentation medium using liquid-liquid extraction in combination with distillation. In this method, the butanol is extracted from the fermentation broth using liquid-liquid extraction with a suitable solvent. The butanol-containing organic phase is then distilled to separate the butanol from the solvent. Distillation in combination with adsorption may also be used to isolate butanol from the fermentation medium. In this method, the fermentation broth containing the butanol is distilled to near the azeotropic composition and then the remaining water is removed by use of an adsorbent, such as molecular sieves (Aden et al. *Lignocellulosic Biomass to Ethanol Process Design and Economics Utilizing Co-Current Dilute Acid Prehydrolysis and Enzymatic Hydrolysis for Corn Stover*, Report NREL/TP-510-32438, National Renewable Energy Laboratory, June 2002).

Additionally, distillation in combination with pervaporation may be used to isolate and purify the butanol from the fermentation medium. In this method, the fermentation broth containing the butanol is distilled to near the azeotropic composition, and then the remaining water is removed by pervaporation through a hydrophilic membrane (Guo et al., *J. Membr. Sci.* 245, 199-210 (2004)).

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, N.Y. (1989) (Maniatis) and by T. J. Silhavy, M. L. Bennan, and L. W. Enquist, *Experiments with Gene Fusions*, Cold Spring Harbor Laboratory Press, Cold Spring Harbor, N.Y. (1984) and by Ausubel, F. M. et al., *Current Protocols in Molecular Biology*, pub. by Greene Publishing Assoc. and Wiley-Interscience (1987).

Materials and methods suitable for the maintenance and growth of bacterial and yeast cultures are well known in the art. Techniques suitable for use in the following Examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989) or in *Yeast Protocols, Second Edition* (Wei Xiao, ed; Humana Press, Totowa, N.J. (2006))). All reagents, restriction enzymes and materials used for the growth and maintenance of bacterial cells were obtained from Aldrich Chemicals (Milwaukee, Wis.), BD Diagnostic Systems (Sparks, Md.), Life Technologies (Rockville, Md.), or Sigma Chemical Company (St. Louis, Mo.) unless otherwise specified.

Methods for Determining Isobutanol Concentration in Culture Media

The concentration of isobutanol in the culture media can be determined by a number of methods known in the art. For example, a specific high performance liquid chromatography (HPLC) method utilizes a Shodex SH-1011 column with a Shodex SH-G guard column, both purchased from Waters Corporation (Milford, Mass.), with refractive index (RI) detection. Chromatographic separation is achieved using 0.01 M $H_2SO_4$ as the mobile phase with a flow rate of 0.5 mL/min and a column temperature of 50° C. Isobutanol has a retention time of 46.6 min under the conditions described. Alternatively, gas chromatography (GC) methods are available. For example, a specific GC method utilizes an HP-INNOWax column (30 m×0.53 mm id, 1 µm film thickness, Agilent Technologies, Wilmington, Del.), with a flame ionization detector (FID). The carrier gas is helium at a flow rate of 4.5 mL/min, measured at 150° C. with constant head pressure; injector split is 1:25 at 200° C.; oven temperature ias 45° C. for 1 min, 45 to 220° C. at 10° C/min, and 22° C. for 5 min; and FID detection is employed at 240° C. with 26 mL/min helium makeup gas. The retention time of isobutanol is 4.5 min.

The meaning of abbreviations is as follows: "s" means second(s), "min" means minute(s), "h" means hour(s), "psi" means pounds per square inch, "nm" means nanometers, "d" means day(s), "µL" means microliter(s), "mL" means milliliter(s), "L" means liter(s), "mm" means millimeter(s), "nm" means nanometers, "mM" means millimolar, "µM" means micromolar, "M" means molar, "mmol" means millimole(s), "µmol" means micromole(s)", "g" means gram(s), "µg" means microgram(s) and "ng" means nanogram(s), "PCR" means polymerase chain reaction, "OD" means optical density, "$OD_{600}$" means the optical density measured at a wavelength of 600 nm, "kDa" means kilodaltons, "g" means the gravitation constant, "bp" means base pair(s), "kbp" means kilobase pair(s), "% w/v" means weight/volume percent, % v/v" means volume/volume percent, "HPLC" means high performance liquid chromatography, and "GC" means gas chromatography.

CM refers to synthetic complete medium which is described in Amberg, Burke and Strathern, 2005, Methods in Yeast Genetics, Cold Spring Harbor Laboratory Press, Cold Spring Harbor, N.Y.

Example 1

Identification of SLT2 from an Isobutanol Tolerance Screen

A yeast genomic library in the *E. coli*/yeast shuttle vector YEp13 was obtained from the American Type Culture Collection (ATCC 37323; Reed et al. (1989) J. Cell Sci. Suppl. 12:29-37). The library was provided in an *E. coli* host and supplies complete coverage of the *Saccharomyces cerevisiae* genome with 10,000 clones containing random and/or overlapping fragments of genomic DNA. The YEp13 vector includes a leu marker. The library was amplified by growth of the *E. coli* mixed culture in LB with ampicillin (50 µg/ml) for 16 hours at 37° C. with shaking, isolated from *E. coli* using a Qiaprep Spin Miniprep Kit (Cat. No. 27104) and transformed into *S. cerevisiae* BY4741 cells (ATCC 201388) using a lithium acetate transformation procedure (Gietz et al. (1995) *Yeast* 11:355-360). Transformants were washed from selection plates (SD Agar minus leucine, called CSM-Leu; Cat #YPL-1540 of KD Medical; Columbia, Md.) and combined to form a pool of at least 10,000 *S. cerevisiae* BY4741 transformants. The pool was mixed with 25% glycerol and stored at −70° C.

Isolation of Isobutanol Tolerance Clones by Screening

The pool was plated on selective media (CM-Leu) and colonies grown at 30° C. were picked to liquid selective medium in microtiter wells and then grown for 2 days at 30° C. with shaking. Glycerol was added to a final concentration of 12% (v/v) and mixed by repeated pipetting prior to freezing at −80° C. Microtiter contents were thawed prior to printing to control and isobutanol containing agar plates (CM-Leu). Leu+ transformants of BY4741 (haploid) were obtained and picked to microtiter wells. Growth of more than 10,000 clones was compared on control plates (complete synthetic medium lacking leucine) and on the same plates containing 1.8% (w/v) isobutanol after 2 days at 30° C. This primary screen identified 638 putative isobutanol tolerant colonies. Positive-scoring colonies were consolidated by inoculating new microtiter plates containing CM-Leu liquid media that were incubated at 30° C. overnight. A secondary screen for isobutanol tolerant clones was accomplished by printing from the consolidated microtiter plates on 1.6%, 1.8% and 2% (w/v) isobutanol containing agar plates and observing growth. This secondary screen identified 14 tolerant clones with improved growth relative to controls, termed BUT (isoBUtanol Tolerant) clones.

Molecular Identity of the BUT Clones

The fragment of genomic DNA present in one of the 14 isobutanol tolerant strains named yBUT11 was characterized as follows. DNA was prepared from 2 µl of well mixed frozen cell glycerol stock (20% final) that was mixed with 9 µl of Genomiphi Sample Buffer prior to the addition of 1 µl zymolase [5 units] (ZymoResearch, Cat#E1004). Samples were incubated for 15 minutes at 37° C. The reaction was terminated by heating for 3 minutes at 95° C. (no longer). The heated sample was cooled at 4° C. for 5 minutes.

To amplify DNA we used the GE/Amersham Biosciences Illustra™ GenomiPhi V2 DNA Amplification Kit (Product number: 25-6600-31) which was stored at −70° C. The kit was not allowed to warm above 4° C. prior to initiation of DNA amplification. Next amplification reactions were set up. A reaction mix was prepared by combining 19.5 µl Reaction Buffer+0.5 µl Enzyme Mix (Genomiphi Version 2). 10 µl of the Reaction Mix was added to the heated and cooled template sample described in the prior paragraph. Amplification reactions were incubated at 30° C. overnight. Amplification reactions were terminated by heating at 65° C. for 10 minutes prior to cooling on ice. This amplified, derivative genomic DNA sample, including the YEp13 clone, was suitable for sequencing without any further manipulation.

DNA sequencing was performed as follows. For each 20 µl Genomiphi amplified sample, 8 µl was removed and added to 8 µl of Big Dye v3.1 Sequencing reagent (PN #4337457 Applied Biosystems, Foster City, Calif., 94404 USA), 4 µl of 10 µM primer (ype13-fwd: 5'-CTATGCGCACCCGT-TCTCGGAGC SEQ ID NO:75, or ype13-rev: 5'-CGCTCAT-GAGCCCGAAGTGGCG SEQ ID NO:76; Sigma Genosys, Woodlands, Tex.), 4 µl 5× Sequencing buffer (PN #4336699 Applied Biosystems, Foster City, Calif.) and 16 µl Molecular Biology Grade water (Mediatech, Inc., Herndon, Va.). The sequencing reactions were then thermal cycled as follows; 3 minutes at 96° C. followed by 200 cycles of (95° C. 30 sec+55° C. 20 sec+60° C. 2 min) then stored at 4° C. The unincorporated ddNTPs were removed prior to sequencing using Edge Biosystems (Gaithersburg, Md.) clean-up plates. For each sequencing reaction the total 40 µl was pipetted into one well of a pre-spun 96 well clean up plate. The plate was then spun for 5 min at 5,000×g in a Sorvall RT-7 refrigerated centrifuge. The cleaned up reactions were then placed directly onto an Applied Biosystems 3730 DNA sequencer and sequenced with automatic base-calling.

The sequences of the two DNA vector-insert junction fragments from each clone were aligned to the yeast genome (Saccharomyces Genome Database) via the BLAST method (Altschul et al. (1997) Nucleic Acids Research 25:3389-3402). Both insert ends were homologous to segments of chromosome VIII. One sequence read matched 813 of 954 nucleotides between nucleotide positions 165109 and 165960 on chromosome VIII while the other junction matched 471 of 477 nucleotides between nucleotide positions 171100 and 170625. These data demonstrated that a 5991 by fragment resides on the plasmid of yBUT11 that contains nucleotides 165109 to 171100 of chromosome VIII of the *S. cerevisiae* genome. This region contains the following ORFs and genetic elements:

DAP2' YHR028W-A YHI9 ARS809 SLT2 'RRM3 where DAP2' indicates a 3' truncation and 'RRM3_indicates a 5'truncation.

ARS809 is a DNA replication element, YHR028W-A is annotated as a dubious open reading frame, and YHI9 encodes a protein of unknown function. The other ORF was SLT2 which encodes a cell wall integrity specific MAP Kinase. This MAP Kinase is part of a regulatory cascade that controls cell wall integrity in yeast (Chen and Thorner (2007) Biochimica et Biophysica Acta 1773: 1311-1340).

Example 2

Isobutanol Sensitivity of SLT2 Deletion Strain

A strain of diploid BY4743 having homozygous deletion of the SLT2 gene from the collection described by Brachmann et al. (Yeast (1998) 14:115-132) was assayed for sensitivity to isobutanol. The Δslt2 strain was plated on YPD medium and incubated for 3 days at 30° C. Colonies were picked and used to inoculate complete synthetic medium with glucose (2%) as the carbon source. They were diluted in the same medium to an OD600 of 0.01. 2 ml aliquots of this suspension were appended with pure isobutanol to the concentrations indicated in Table 5. Cultures were agitated on a roller drum at 30° C. for 2 days. Cultures were tested for growth yield after 1 and 2 days, assayed in triplicate. 1 day (20 hr) data is provided in Table 5.

TABLE 5

Growth of Δslt2 strain in isobutanol.

| [ISO] | OD (A600) | |
|---|---|---|
| (wt %) | BY4743 | Δslt2/Δslt2 |
| 0.00 | >1 | >1 |
| 0.25 | >1 | 0.07 |
| 0.50 | >1 | 0.03 |
| 0.75 | 0.07 | 0.03 |
| 0.87 | 0.07 | 0.01 |
| 1.00 | 0.04 | 0.01 |
| 1.25 | 0.02 | 0.02 |
| 1.50 | 0.04 | 0.02 |

Both data sets indicated that the homozygous SLT2 deletion strain was isobutanol-hypersensitive at 0.25 and 0.5 wt % isobutanol Example 3

Overexpression of SLT2 Coding Region

The effect of overexpression of the SLT2 coding region was assessed as follows. A Yeast ORF collection (Gelperin, White et al. (2005) *Genes Dev.* 19(23):2816-2826)_is available from Open Biosystems (Huntsville, Ala.). In this collection yeast ORFs are expressed from the GAL1 promoter in the vector BG1805. This vector can be introduced into ura3 yeast mutants and transformants selected for uracil prototrophy. In the presence of galactose and the absence of glucose, expression from the GAL1 promoter is elevated about 1000 fold relative to the barely detectable level observed with glucose grown cells (Johnston and Davis (1984) Mol. Cell. Biol. 4(8):1440-1448). Note that each ORF encodes a fusion protein of the form:

N terminal yeast ORF-C terminal epitope tag

A plasmid containing the SLT2 ORF was obtained from this collection (YSC3867-9522814) and transformed into yeast strain BY4741 selecting for uracil prototrophy. To measure the effects of isobutanol we compare the growth observed in an isobutanol-treated culture in galactose medium to an untreated culture grown in the same medium lacking isobutanol. Growth yield was measured by the following method. A fresh colony of a transformant was used to inoculate a tube in which CM galactose minus uracil medium had been placed. This medium provides selection for plasmid maintenance. The resultant culture was incubated at 30° C. on a roller drum to provide aeration. The parent BY4741 was cultured in this medium modified by the inclusion of uracil to satisfy its uracil requirement. The culture was diluted into fresh medium (10 ml) to OD600 of approximately 0.4. Absorbance was recorded. Cultures were grown for 2-3 hours to allow one doubling. Absorbance was recorded at this time and was called T=0. The culture was divided into two equal parts; each was diluted with an equal volume of pre-warmed fresh media. In one sample the fresh media was supplemented with 1 wt % isobutanol; in the other (control) the fresh media was unadulterated. OD600 was measured after incubation on a roller drum for 1 day. Absorbencies presented were averages of triplicate control and triplicate treated cultures. Percent growth was calculated as 100×[average A600 of the triplicate isobutanol challenged cultures/average A600 of the triplicate control cultures.

Results for a 22 hr experiment indicated that the parental strain (BY4741) grown in galactose displayed a 27% growth yield in the presence of 1 wt % isobutanol relative to the uninhibited culture (measures are averages of triplicate cultures with standard deviations of less than 6% under each of the conditions tested for both strains). In contrast, the SLT2p over-producing strain grown in galactose displayed a growth yield of 56% yield in the presence of 1 wt % isobutanol, a 29% improvement.

Example 4 (Prophetic)

Production of Isobutanol in Recombinant *S. cerevisiae* with Engineered Isobutanol Pathway and SLT2 Overexpression The purpose of this prophetic example is to describe how to enhance isobutanol production in a yeast strain by combining an isobutanol biosynthetic pathway with SLT2 overexpression. To this end we need to disrupt TRP1, the gene encoding phosphoribosylanthranilate isomerase that catalyzes the third step in tryptophan biosynthesis, to provide a third selectable marker. BY4741 is the starting strain. A cassette containing DNA sequences that are located upstream and downstream just outside of TRP1 (up TRP1 and downTRP1) is created containing the following elements: upTRP1 DR URA3* DR downTRP1, where DR are direct repeat sequences and URA3* is a heterologous URA3 gene. The upTRP1 DR URA3* DR downTRP1 fragment is constructed by the method of Reid et al. ((2002) Yeast 19(4):319-328). Following this method the 5' and 3' flanking regions of the TRP1 gene, which contain the up TRP1 and downTRP1 sequences, are prepared. These are called intergenic DNAs iYHR029C and iYHR030C, respectively.

Intergenic DNA iYDR006C is amplified from *S. cerevisiae* genomic DNA using PCR with the following primers where the small letters are the adaptamers described in Reid et al. (ibid) and the capital letters are yeast genomic DNA:

Forward:
(SEQ ID NO: 77)
ccgctgctaggcgcgccgtgTCTGAAAACGGAAGAGGAGTAGG

Reverse:
(SEQ ID NO: 78)
gcagggatgcggccgctgacATAACAGACATACTCCAAGCTGCC

Intergenic DNA iYDR008C is amplified from *S. cerevisiae* genomic DNA using PCR with the following primers where the small letters are the adaptamers described in Reid et al. (ibid.) and the capital letters are yeast genomic DNA:

Forward:
(SEQ ID NO: 79)
ccgctgctaggcgcgccgtgCATTTGGCTTTTTGATTGATTGTAC

Reverse:
(SEQ ID NO: 80)
gcagggatgcggccgctgacACTTTTATTTTCTCTTTTTGCACTCCT

The two intergenic DNA PCR fragments are each used together with the plasmid pWJ1077, containing DR URA3*DR (Reid et al. ibid.), as template for PCR to produce DNA fragments containing each intergenic DNA sequence and a portion of the URA3* sequence, with overlap of the URA3* sequence between the two resulting fragments: upTRP1 DR UR and RA3* DR downTRP1. This is because there is complementarity between the right end of iYDR006C and a sequence on the plasmid pWJ1077 left of the DR upstream relative to URA3. Similarly, there is complementarity between the left end of iYDR006C and a sequence on the plasmid pWJ1077 right of the DR downstream relative to URA3. Primers for iYDR006C and pWJ1077 templates are C and kli3' (SEQ ID NOS:81 and 82). Primers for iYDR008C and pWJ1077 templates are D and kli5" (SEQ ID NOs:83 and 84).

Co-transformation of these two fragments into yeast allows recombination between the two fragments to create a cassette containing an intact URA3* gene flanked by upTRP1 and downTRP1 sequences. Recombination of this cassette into the yeast chromosome results in the replacement of TRP1 by DR URA3* DR. Transformants with this recombination event are selected by demanding growth in the absence of pyrimidines but in the presence of tryptophan. The recombinant requires tryptophan to grow. Excision of URA3* is accomplished by homologous recombination between the DR's and its loss is selected for with 5-FOA to create BY4741ΔTRP1.

Construction of vectors pRS423::CUP1p-alsS+FBAp-ILV3 and pHR81::FBAp-ILV5-GPMp-kivD is described in US Patent Publication # US20070092957 A1, Example 17, which is herein incorporated by reference. pRS423::CUP1p-alsS+FBAp-ILV3 has a chimeric gene containing the CUP1 promoter (SEQ ID NO:85), the alsS coding region from *Bacillus subtilis* (SEQ ID NO:41), and CYC1 terminator (SEQ ID NO:86) as well as a chimeric gene containing the FBA promoter (SEQ ID NO:87), the coding region of the ILV3 gene of *S. cerevisiae* (SEQ ID NO:47), and the ADH1 terminator (SEQ ID NO:88). pHR81::FBAp-ILV5+GPMp-kivD is the pHR81 vector (ATCC #87541) with a chimeric gene containing the FBA promoter, the coding region of the ILV5 gene of *S. cerevisiae* (SEQ ID NO:43), and the CYC1 terminator as well as a chimeric gene containing the GPM promoter (SEQ ID NO:89), the coding region from kivD gene of *Lactococcus lactis* (SEQ ID NO:35), and the ADH1 terminator. pHR81 has URA3 and leu2-d selection markers.

Plasmid vectors pRS423::CUP1p-alsS+FBAp-ILV3 and pHR81::FBAp-ILV5+GPMp-kivD are transformed into BY4741ΔTRP1 using standard genetic techniques to yield the doubly transformed strain BY4741ΔTRP1-iso (*Methods in Yeast Genetics,* 2005, Cold Spring Harbor Laboratory Press, Cold Spring Harbor, N.Y.). BY4741ΔTRP1-iso is maintained on synthetic complete media lacking histidine and uracil.

Next the YRp7 plasmid (Botstein et al. (1979) Gene 8(1): 17-240), which is available from ATCC (catalog number 37060), and has unique restriction sites within the Tet gene (BamHI, SalI, EagI, NruI), is digested with BamHI to yield a linear fragment which is then dephosphorylated. To it is ligated the SLT2 gene fragment that is amplified, including 1 kbp of flanking sequence on both ends, from yeast chromosomal DNA using the primers:

ccatggt*ggatcc*GTGGTGAAAATGAAGGAAAT   (SEQ ID NO: 90)
and ccatgg*ggatcc*ATCTTCATAAACGTTTATCA.   (SEQ ID NO: 91)

Prior to ligation the PCR product is digested with BamHI (restriction sites underlined and italicized) to yield compatible sticky ends. The resultant plasmid (YRp7-SLT2) is selected based upon ampicillin resistance in *E. coli* and is confirmed molecularly (liberation of an approximately 3.5 kbp fragment upon BamHI digestion) and phenotypically by being tetracycline sensitive. The plasmid is then isolated from *E. coli* and transformed into yeast strains, selecting for the ability to grow in the absence of tryptophan (TRP1 function).

BY4741ΔTRP1-iso is next transformed with yRP7-SLT2, selecting for the ability to grow without tryptophan supplementation, yielding BY4741ΔTRP1-iso-SLT2. BY4741ΔTRP1-iso is also transformed with yRP7 selecting for the ability to grow without tryptophan supplementation yielding BY4741ΔTRP1-iso-c. Aerobic cultures are grown in 250 ml flasks containing 50 ml synthetic complete media lacking histidine, tryptophan and uracil, and supplemented with 2% glucose in an Innova4000 incubator (New Brunswick Scientific, Edison, N.J.) at 30° C. and 225 rpm. Low oxygen cultures are prepared by adding 45 mL of medium to 60 mL serum vials that are sealed with crimped caps after inoculation and kept at 30° C. Approximately 24 h and 48 h after induction with 0.03 mM $CuSO_4$ (final concentration), an aliquot of the broth is analyzed by HPLC (Shodex Sugar SH1011 column (Showa Denko America, Inc. NY) with refractive index (RI) detection and GC (HP-Innowax, 0.32 mm×0.25 µm×30 m (Agilent Technologies, Inc., Santa Clara, Calif.) with flame ionization detection (FID) for isobutanol content. Isobutanol is detected. More isobutanol is produced by BY4741ΔTRP1-iso-SLT than by BY4741ΔTRP1-iso-c.

What is claimed is:

1. A recombinant yeast cell comprising:
   a) an isobutanol biosynthetic pathway, wherein the isobutanol biosynthetic pathway comprises at least one gene encoding a polypeptide that performs at least one of the following substrate to product conversions:
      i) pyruvate to acetolactate, as catalyzed by acetolactate synthase;
      ii) acetolactate to 2,3-dihydroxyisovalerate, as catalyzed by acetohydroxy acid isomeroreductase;
      iii) 2,3-dihydroxyisovalerate to α-ketoisovalerate, as catalyzed by dihydroxyacid dehydratase;
      iv) α-ketoisovalerate to isobutyraldehyde, as catalyzed by branched-chain keto acid decarboxylase; and
      v) isobutyraldehyde to isobutanol, as catalyzed by a branched-chain alcohol dehydrogenase; and
   b) at least one genetic modification which increases cell wall integrity pathway activity, wherein the genetic modification increases activity of a mitogen-activated protein kinase module of the cell wall integrity pathway, and wherein the genetic modification is overexpression of a STL2 protein encoding gene;
wherein the isobutanol biosynthetic pathway comprises at least one gene that is heterologous to the yeast cell and wherein the yeast cell has an increase in tolerance to isobutanol and at least a 20% improvement in growth yield as compared with a yeast cell that lacks the at least one genetic modification of (b).

2. The recombinant yeast cell of claim 1 wherein the cell has at least a 29% improvement in growth yield in 1% (weight/volume) isobutanol as compared to a parental cell having no increase in activity of the cell wall integrity pathway.

3. The recombinant yeast cell of claim 1 selected from the group consisting of *Saccharomyces, Schizosaccharomyces, Hansenula, Candida, Kluyveromyces, Yarrowia* and *Pichia*.

4. The yeast cell of claim 1 wherein the genetic modification increases STL2p serine/threonine MAP kinase activity.

5. The yeast cell of claim 1 wherein the STL2 protein encoding gene is heterologous to the yeast cell.

6. The yeast cell of claim 1 wherein the at least one gene encoding the acetolactate synthase, acetohydroxy acid isomeroreductase, acetohydroxy acid dehydratase, dihydroxyacid dehydratase, branched-chain keto acid decarboxylase, or branched-chain alcohol dehydrogenase is heterologous to the yeast cell.

7. method for the production of isobutanol comprising growing the recombinant yeast cell of claim 1 under conditions where isobutanol is produced and optionally recovering the isobutanol.

8. A method for improving fermentative production of isobutanol comprising:
   a) providing the recombinant yeast cell of claim 1; and
   b) contacting said yeast cell with fermentable sugar whereby said yeast cell produces isobutanol and wherein said yeast cell has improved tolerance to said isobutanol and improved growth yield as compared to a yeast cell without the at least one genetic modification that increases activity of the mitogen-activated protein kinase module of the cell wall integrity pathway.

* * * * *